US007176026B2

(12) United States Patent
Van Thielen et al.

(10) Patent No.: US 7,176,026 B2
(45) Date of Patent: *Feb. 13, 2007

(54) PROTEIN KINASE STRESS-RELATED POLYPEPTIDES AND METHODS OF USE IN PLANTS

(75) Inventors: Nocha Van Thielen, Chapel Hill, NC (US); Oswaldo da Costa e Silva, Rheinland-Pfalz (DE); Ruoying Chen, Apex, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 634 days.

This patent is subject to a terminal disclaimer.

(21) Appl. No.: 10/292,408

(22) Filed: Nov. 12, 2002

(65) Prior Publication Data

US 2003/0182692 A1 Sep. 25, 2003

Related U.S. Application Data

(60) Provisional application No. 60/346,096, filed on Nov. 9, 2001.

(51) Int. Cl.
*A01H 5/00* (2006.01)
*C12N 15/82* (2006.01)
*C12N 15/87* (2006.01)
*C12N 5/14* (2006.01)
*C07H 21/00* (2006.01)

(52) U.S. Cl. .................. 435/468; 435/320.1; 435/419; 800/287; 800/289; 536/23.6

(58) Field of Classification Search ........ 800/278–287, 800/289; 435/320.1, 419, 468; 536/23.6
See application file for complete search history.

(56) References Cited

U.S. PATENT DOCUMENTS

| 6,867,351 B2 * | 3/2005 | da Costa e Silva et al. | 800/289 |
| 2005/0066396 A1 * | 3/2005 | Shirley et al. ............... | 800/289 |

FOREIGN PATENT DOCUMENTS

| EP | 1 078 985 A2 | 2/2001 |
| WO | WO 98/26045 | 6/1998 |
| WO | WO 99/54489 | 10/1999 |
| WO | WO 00/06706 | 2/2000 |
| WO | WO 00/09724 | 2/2000 |
| WO | WO 01/02541 A2 | 1/2001 |
| WO | WO 01/45492 | 6/2001 |
| WO | WO 01/77355 | 10/2001 |
| WO | WO 01/77356 | 10/2001 |
| WO | WO 01/77356 A2 * | 10/2001 |

OTHER PUBLICATIONS

Urao et al. (Plant Cell, 11:1743-1754, 1999).*
Hardle (Annu. Rev. Plant Physiol., 50:97-131, 1999).*
Keskin et al (Protein Science, 13:1043-1055, 2004).*
Kilby et al. (The Plant Journal, 8:637-652, 1995).*
Becraft, P.W., "Receptor kinases in plant development", Trends Plant Sci., 3(10):384-388, 1998.
Bush, D.S., "Calcium Regulation in Plant Cells and its Role in Signaling", Annu. Rev. Plant Physiol. Plant Mol. Biol., 46:95-122, 1995.
Jonak, C. et al., "Stress signaling in plants: A mitogen-activated protein kinase pathway is activated by cold and drought", Proc. Natl. Acad. Sci., 93:11274-11279, 1996.
Knight et al., "Transgenic plant aequorin reports the effects of touch and cold-shock and elicitors on cytoplasmic calcium", Nature, 352:524-526, 1991.
Kovtun, Y. et al., "Functional analysis of oxidative stress-activated mitogen-activated protein kinase cascade in plants", Proc. Natl. Acad. Sci., vol. 97, No. 6, pp. 2940-2945, 2000.
Lee, J.H. et al., "A highly conserved kinase is an essential component for stress tolerance in yeast and plant cells", Proc. Natl. Acad. Sci., 96:5873-5877, 1999.
Database EMBL online, "ga71e12.y1 Moss EST library PPU *Physcomitrella patens* cDNA clone PEP_SOURCE_ID:PPU121123 5' similar to TR:O65461 ..." Mar. 7, 2000, Acc. No. AW510033.
Database EMBL online, "*Physcomitrella patens* subsp. patens cDNA clone:pphn9a09, 5' end, single read" Jan. 23, 2002, Acc. #BJ205855.
Saijo et al., "A Ca2+-Dependent Protein Kinase that Endows Rice Plants with Cold- and Salt-Stress Tolerance Functions in Vascular Bundles", Plant Cell Physiol., 2001, 42(11):1228-1233.
Urao et al., "A Transmembrane Hybrid-Type Histidine Kinase in *Arabidopsis* Functions as an Osmosensor", Plant Cell, 1999, 11:1743-1754.

* cited by examiner

*Primary Examiner*—Ashwin Mehta
*Assistant Examiner*—Vinod Kumar
(74) *Attorney, Agent, or Firm*—Elaine Sale; Ruoying Chen; Mark Westhafer

(57) ABSTRACT

A transgenic plant transformed by a Protein Kinase Stress-Related Polypeptide (PKSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated PKSRPs, and isolated nucleic acid coding PKSRPs, and vectors and host cells containing the latter.

26 Claims, 2 Drawing Sheets

LB  g7T  aacCI  nosP          Super promoter  "Gene of Interest"  NOSpA  RB pBPS-JH001

LB  g7T  aacCI  nosP         Super promoter  "Gene of Interest"  NOSpA  RB pBPS-SC022

SEQUENCE LISTING

```
<160> NUMBER OF SEQ ID NOS: 51

<210> SEQ ID NO 1
<211> LENGTH: 1100
<212> TYPE: DNA
<213> ORGANISM: Physcomitrella patens

<400> SEQUENCE: 1
cggcaccagc atcttcgcga ggcatgtgat gtgtggtcgg tggagttagc ttctacgggc      60
aactggaaat ccagggaatt ctgccagaat tatacgtact aaagtagaaa tttacgtttc     120
ggggacttcg agtcttctat ggcatctgcg actgcgggta ttatcaacag cacaaacatg     180
atcggaggag gaatagctcc aactaaagct ggctcaagcg gagtagaatt gttaccgaaa     240
gaaatgcacg acatgaagct cagggatgac aaggttgacc acagcgacga caaggaaatt     300
gaggcttcaa tagtagatgg aaacggtacc gaaactggcc acatcatagc tactactatt     360
ggagggcgaa atggacaacc taagcagacg atcagctatt cggcagaacg tgttgttggc     420
actggatcat tcgggattgt cttccaggca aaatgcatcg aaactgggga gacggtggct     480
ataaagaaag tgttgcagga caaagatac aagaatcgag agctgcagat catgcgactg     540
ttggaccacc cgaatattgt agctttgaag cattgcttct tctcgacgac ggataaagac     600
gaattgtact taaacctggt gctggagtat gtacccgaga cggtgtatcg tattgcaaag     660
cactacaatc gcatgaatca gcgaatgccc cttgtttacg tgaaactgta cacgtatcag     720
atatgccgat cactggcata tatccacaat ggcatcggtg tctgccaccg cgacatcaag     780
ccccagaacc tgctggtgga atcctcatac gcaccagctg aaactgtgtg attttgggaa     840
gtgcgaaagt gctggtgaaa ggggagccca atatctcgta catttgttcg cggtactacc     900
```

-continued

| | |
|---|---:|
| gtgctccggg agcttatttt tggagcgacg gagtacacga ctgccataga tatatggtcg | 960 |
| atgggttgcg tgatggcaga gcttctacta ggacagcctt tgtttcctgg agagagtgga | 1020 |
| gtggatcaat tggtgaaat catcaaggtt ttggggacac cgactcgtga ggagatcaag | 1080 |
| tgcatgaatc cgaactacac | 1100 |

<210> SEQ ID NO 2
<211> LENGTH: 1849
<212> TYPE: DNA
<213> ORGANISM: Physcomitrella patens

<400> SEQUENCE: 2

| | |
|---|---:|
| ggcaccagca tcttcgcgag gcatgtgatg tgtggtcggt ggagttagct tctacgggca | 60 |
| actggaaatc cagggaattc tgccagaatt atacgtacta agtagaaat ttacgtttcg | 120 |
| gggacttcga gtcttctatg catctgcga ctgcgggtat tatcaacagc acaaacatga | 180 |
| tcggaggagg aatagctcca actaaagctg gctcaagcgg agtagaattg ttaccgaaag | 240 |
| aaatgcacga catgaagctc agggatgaca aggttgacca cagcgacgac aaggaaattg | 300 |
| aggcttcaat agtagatgga aacgtaccg aaactggcca catcatagct actactattg | 360 |
| gagggcgaaa tggacaacct aagcagacga tcagctattc ggcagaacgt gttgttggca | 420 |
| ctggatcatt cggattgtc ttccaggcaa atgcatcga aactggggag acggtggcta | 480 |
| taaagaaagt gttgcaggac aaaagataca agaatcgaga gctgcagatc atgcgactgt | 540 |
| tggaccaccc gaatattgta gctttgaagc attgcttctt ctcgacgacg ataaagacg | 600 |
| aattgtactt aaacctggtg ctggagtatg tacccgagac ggtgtatcgt attgcaaagc | 660 |
| actacaatcg catgaatcag cgaatgcccc ttgtttacgt gaaactgtac acgtatcaga | 720 |
| tatgccgatc actggcatat atccacaatg gcatcggtgt ctgccaccgc gacatcaagc | 780 |
| cccagaacct gctggtgaat cctcatacgc accagctgaa actgtgtgat tttggaagtg | 840 |
| cgaaagtgct ggtgaaaggg gagcccaata tctcgtacat ttgttcgcgg tactaccgtg | 900 |
| ctccggagct tatttttgga gcgacggagt acacgactgc catagatata tggtcgatgg | 960 |
| gttgcgtgat ggcagagctt ctactaggac agcctttgtt tcctggagag agtggagtgg | 1020 |
| atcaattggt ggaaatcatc aaggttttgg gacaccgac tcgtgaggag atcaagtgca | 1080 |
| tgaatccgaa ctacacagag ttcaagtttc cacaaatcaa ggcgcacccg tggcacaaag | 1140 |
| ttttccacaa acgcatgcca cctgaagcag ttgacttggt gtcaaggctc cttcagtact | 1200 |
| ctccaaatct gcggtgcaac gctctggaag cgtgtgtgca cccgttcttt gatgagctaa | 1260 |
| gggatcctaa ctgccggctt ccgaatgggc ggccactgcc ctctctgttc aacttcaaaa | 1320 |
| cccaagagtt gaagggtgca actcctgata ttctgcagcg tttgataccc gagcacgcga | 1380 |
| ggaagcagaa tccgatgctg gcgctgtgag gggtgcctgg aaagagatcg gaagagtcta | 1440 |
| ctgcgtgaaa ggttttcctc tgtttggagg agtggtccgc tttgtggagg gcttcatagg | 1500 |
| cactctgtat cattgcttaa acacgtaaag tcaaccaatt tgctatggat ccctgctttc | 1560 |
| gctgtgattg gaggaagact tagtagacga ttagcatgcc acttttagga acggcaattc | 1620 |
| tcctgtagtg aaggttacga ttctattgta cttcagaacg gtaaaggtat ttagggggttc | 1680 |
| tcagtgcttc ctgatttggg tacgtgatgt accattggaa aggcttcaaa cgcatgtata | 1740 |
| tctatgagac tttgacgtta ctttttatcg tcagtactca ggaagctcct ctctggatgg | 1800 |
| gattatccat tcgtgccgtt cgaatcgcaa taaaaaaaaa aaaaaaaa | 1849 |

-continued

<210> SEQ ID NO 3
<211> LENGTH: 423
<212> TYPE: PRT
<213> ORGANISM: Physcomitrella patens

<400> SEQUENCE: 3

```
Met Ala Ser Ala Thr Ala Gly Ile Ile Asn Ser Thr Asn Met Ile Gly
 1               5                  10                  15

Gly Gly Ile Ala Pro Thr Lys Ala Gly Ser Ser Gly Val Glu Leu Leu
             20                  25                  30

Pro Lys Glu Met His Asp Met Lys Leu Arg Asp Asp Lys Val Asp His
         35                  40                  45

Ser Asp Asp Lys Glu Ile Glu Ala Ser Ile Val Asp Gly Asn Gly Thr
     50                  55                  60

Glu Thr Gly His Ile Ile Ala Thr Thr Ile Gly Gly Arg Asn Gly Gln
 65                  70                  75                  80

Pro Lys Gln Thr Ile Ser Tyr Ser Ala Glu Arg Val Val Gly Thr Gly
                 85                  90                  95

Ser Phe Gly Ile Val Phe Gln Ala Lys Cys Ile Glu Thr Gly Glu Thr
            100                 105                 110

Val Ala Ile Lys Lys Val Leu Gln Asp Lys Arg Tyr Lys Asn Arg Glu
        115                 120                 125

Leu Gln Ile Met Arg Leu Leu Asp His Pro Asn Ile Val Ala Leu Lys
    130                 135                 140

His Cys Phe Phe Ser Thr Thr Asp Lys Asp Glu Leu Tyr Leu Asn Leu
145                 150                 155                 160

Val Leu Glu Tyr Val Pro Glu Thr Val Tyr Arg Ile Ala Lys His Tyr
                165                 170                 175

Asn Arg Met Asn Gln Arg Met Pro Leu Val Tyr Val Lys Leu Tyr Thr
            180                 185                 190

Tyr Gln Ile Cys Arg Ser Leu Ala Tyr Ile His Asn Gly Ile Gly Val
        195                 200                 205

Cys His Arg Asp Ile Lys Pro Gln Asn Leu Leu Val Asn Pro His Thr
    210                 215                 220

His Gln Leu Lys Leu Cys Asp Phe Gly Ser Ala Lys Val Leu Val Lys
225                 230                 235                 240

Gly Glu Pro Asn Ile Ser Tyr Ile Cys Ser Arg Tyr Tyr Arg Ala Pro
                245                 250                 255

Glu Leu Ile Phe Gly Ala Thr Glu Tyr Thr Thr Ala Ile Asp Ile Trp
            260                 265                 270

Ser Met Gly Cys Val Met Ala Glu Leu Leu Leu Gly Gln Pro Leu Phe
        275                 280                 285

Pro Gly Glu Ser Gly Val Asp Gln Leu Val Glu Ile Ile Lys Val Leu
    290                 295                 300

Gly Thr Pro Thr Arg Glu Glu Ile Lys Cys Met Asn Pro Asn Tyr Thr
305                 310                 315                 320

Glu Phe Lys Phe Pro Gln Ile Lys Ala His Pro Trp His Lys Val Phe
                325                 330                 335

His Lys Arg Met Pro Pro Glu Ala Val Asp Leu Val Ser Arg Leu Leu
            340                 345                 350

Gln Tyr Ser Pro Asn Leu Arg Cys Asn Ala Leu Glu Ala Cys Val His
        355                 360                 365

Pro Phe Phe Asp Glu Leu Arg Asp Pro Asn Cys Arg Leu Pro Asn Gly
    370                 375                 380
```

```
Arg Pro Leu Pro Ser Leu Phe Asn Phe Lys Thr Gln Glu Leu Lys Gly
385                 390                 395                 400

Ala Thr Pro Asp Ile Leu Gln Arg Leu Ile Pro Glu His Ala Arg Lys
                405                 410                 415

Gln Asn Pro Met Leu Ala Leu
            420

<210> SEQ ID NO 4
<211> LENGTH: 420
<212> TYPE: DNA
<213> ORGANISM: Physcomitrella patens
<220> FEATURE:
<221> NAME/KEY: modified_base
<222> LOCATION: (223)
<223> OTHER INFORMATION: a, t, c , g, unknown or other
<220> FEATURE:
<221> NAME/KEY: modified_base
<222> LOCATION: (228)
<223> OTHER INFORMATION: a, t, c , g, unknown or other
<220> FEATURE:
<221> NAME/KEY: modified_base
<222> LOCATION: (261)
<223> OTHER INFORMATION: a, t, c , g, unknown or other
<220> FEATURE:
<221> NAME/KEY: modified_base
<222> LOCATION: (266)
<223> OTHER INFORMATION: a, t, c , g, unknown or other
<220> FEATURE:
<221> NAME/KEY: modified_base
<222> LOCATION: (364)
<223> OTHER INFORMATION: a, t, c , g, unknown or other
<220> FEATURE:
<221> NAME/KEY: modified_base
<222> LOCATION: (388)
<223> OTHER INFORMATION: a, t, c , g, unknown or other
<220> FEATURE:
<221> NAME/KEY: modified_base
<222> LOCATION: (393)
<223> OTHER INFORMATION: a, t, c , g, unknown or other

<400> SEQUENCE: 4
gcacgaggat cgaccgggtg gagtacgtgc actcgcgagg tctaattcat cgtgacttga    60
aaccagataa tttcctcatg ggctgcggcc ggcaagggaa ccaagtgttc attattgact   120
ttggcttggc aaaagagtac atcgaccccg cgacacgtag acacattcct taccgagata   180
gaaagagctt tacaggaaca cgcgggtatg ctagtaggaa tcnccacnaa ggaatcgaac   240
acagcaggag agatgacata naatcncttg gttacattct tatgtacttt cttagggga   300 atttaccatg gcaaggtcaa gggggcaac gtttcaccga tcagaagcaa catgagtaca   360
tgcncaacaa aattaagatg gagactanca tcnaggatct ctgcgatggg tacccagaca   420

<210> SEQ ID NO 5
<211> LENGTH: 1795
<212> TYPE: DNA
<213> ORGANISM: Physcomitrella patens

<400> SEQUENCE: 5
gcccttatcc cgggaggcat tgaactacct ggagtgagat tttttttggga atttgaaaga    60 gaattacata tatacaaggt tgaggctcac cgagaacaag tctgctgata gcttcttcac   120
tcttgaaata gatagttcat catggattca ggaggtgacc gcgtgcgagc tcctcagaag   180
cagtctcgcg aggaggatca gtaccgttca ttgaacattg ctacagagca tcgtcagcat   240
atacagaagc accaacaaca ccaacagcag ccggggactg gattggttgt tgaaacgctt   300
caaaaaacac tatgtaacgt gactgtgacc tcacctacaa gcagtccgga ggggggtaga   360
```

-continued

```
ttacgtactg ttgcgaacaa gtatgcagtg gaaggaatgg tcggcagtgg cgcatttttgc    420 aaggtgtacc agggttctga cttaaccaac catgaggttg tgggcatcaa gctcgaggat    480
acaagaacag agcacgcaca attgatgcac gagtcgcgat tatacaacat tttgcggggt    540
ggaaagggag tgcccaacat gagatggttt gggaaagagc aagactacaa tgtgatggtg    600
ctagatttgc tggggcctaa cctactgcac cttttcaagg tgtgtgggca agattttcg     660 ttgaagacgg tgatcatgtt ggggtaccaa atgatcgacc gggtggagta cgtgcactcg    720
cgaggtctag ttcatcgtga cttgaaacca gataatttcc tcatgggctg cggccggcaa    780
gggaaccaag tgttcattat tgactttggc ttggcaaaag agtacatcga ccccgcgaca    840
cgtagacaca ttccttaccg agatagaaag agctttacag gaacagcgcg gtatgctagt    900
aggaatcagc acaaaggaat cgaacacagc aggagagatg acatagaatc acttggttac    960
attcttatgt actttcttag ggggaattta ccatggcaag gtcaagggggg gcaacgtttc   1020 accgatcaga agcaacatga gtacatgcac aacaaaatta agatggagac taccatcgag   1080
gatctctgcg atgggtaccc cagacaattt gccgactttt tacaccacgc gcgcgagttg   1140
ggattctatg agcagcctga ctactcgtac cttcgcagcc tgttccgtga tcttttcatt   1200
cagaagaaat ccagcttgaa ccatgtctac gactggacag tgtacactca acctcctcag   1260
aatggctctg cacaaacagt tcgaagcccg gctgccggtc cacagactca cttacaaagt   1320 cgccccttcca atgtatcata ttgtccacct ctgactaaac cagagttccg gcgtgaggta   1380
gttgcggcga attagggttt acacaggaag agatgtggta aagcatctca tcttcttcgt   1440
tctggtgcca aaatggtaca aggtcgtctg ctgtctcttt ctcgcaagcc ctcacatata   1500
gatgaaggtt tgtgaagtta gagatgcaac taccaagcaa aggctaggaa aagagctgta   1560
gactttctag tgtgtagtgt gtaaatcaag gcttctggca tggtatcggc agtcaggtgc   1620
atggagcaga atagaaatta cttcgtgcat gacaagattt tttttcttgc agagctctcg   1680
acggttctgc gatctcactt tctctacacaa ccagcgctcc tttaattgaa aagaggatct   1740
ggtacgagta tgataaagtt aacacagatt actagttcaa cgatatcgca agggc         1795
```

<210> SEQ ID NO 6
<211> LENGTH: 417
<212> TYPE: PRT
<213> ORGANISM: Physcomitrella patens

<400> SEQUENCE: 6

```
Met Asp Ser Gly Gly Asp Arg Val Arg Ala Pro Gln Lys Gln Ser Arg
 1               5                  10                  15

Glu Glu Asp Gln Tyr Arg Ser Leu Asn Ile Ala Thr Glu His Arg Gln
             20                  25                  30

His Ile Gln Lys His Gln Gln His Gln Gln Gln Pro Gly Thr Gly Leu
         35                  40                  45

Val Val Glu Thr Leu Gln Lys Thr Leu Cys Asn Val Thr Val Thr Ser
     50                  55                  60

Pro Thr Ser Ser Pro Glu Gly Gly Arg Leu Arg Thr Val Ala Asn Lys
 65                  70                  75                  80

Tyr Ala Val Glu Gly Met Val Gly Ser Gly Ala Phe Cys Lys Val Tyr
                 85                  90                  95

Gln Gly Ser Asp Leu Thr Asn His Glu Val Val Gly Ile Lys Leu Glu
            100                 105                 110

Asp Thr Arg Thr Glu His Ala Gln Leu Met His Glu Ser Arg Leu Tyr
        115                 120                 125
```

```
Asn Ile Leu Arg Gly Gly Lys Gly Val Pro Asn Met Arg Trp Phe Gly
        130                 135                 140
Lys Glu Gln Asp Tyr Asn Val Met Val Leu Asp Leu Gly Pro Asn
145                 150                 155                 160
Leu Leu His Leu Phe Lys Val Cys Gly Gln Arg Phe Ser Leu Lys Thr
                165                 170                 175
Val Ile Met Leu Gly Tyr Gln Met Ile Asp Arg Val Glu Tyr Val His
            180                 185                 190
Ser Arg Gly Leu Val His Arg Asp Leu Lys Pro Asp Asn Phe Leu Met
        195                 200                 205
Gly Cys Gly Arg Gln Gly Asn Gln Val Phe Ile Ile Asp Phe Gly Leu
    210                 215                 220
Ala Lys Glu Tyr Ile Asp Pro Ala Thr Arg His Ile Pro Tyr Arg
225                 230                 235                 240
Asp Arg Lys Ser Phe Thr Gly Thr Ala Arg Tyr Ala Ser Arg Asn Gln
                245                 250                 255
His Lys Gly Ile Glu His Ser Arg Arg Asp Asp Ile Glu Ser Leu Gly
            260                 265                 270
Tyr Ile Leu Met Tyr Phe Leu Arg Gly Asn Leu Pro Trp Gln Gly Gln
        275                 280                 285
Gly Gly Gln Arg Phe Thr Asp Gln Lys Gln His Glu Tyr Met His Asn
    290                 295                 300
Lys Ile Lys Met Glu Thr Thr Ile Glu Asp Leu Cys Asp Gly Tyr Pro
305                 310                 315                 320
Arg Gln Phe Ala Asp Phe Leu His His Ala Arg Glu Leu Gly Phe Tyr
                325                 330                 335
Glu Gln Pro Asp Tyr Ser Tyr Leu Arg Ser Leu Phe Arg Asp Leu Phe
            340                 345                 350
Ile Gln Lys Lys Phe Gln Leu Asp His Val Tyr Asp Trp Thr Val Tyr
        355                 360                 365
Thr Gln Pro Pro Gln Asn Gly Ser Ala Gln Thr Val Arg Ser Pro Ala
    370                 375                 380
Ala Gly Pro Gln Thr His Leu Gln Ser Arg Pro Ser Asn Val Ser Tyr
385                 390                 395                 400
Cys Pro Pro Leu Thr Lys Pro Glu Phe Arg Arg Glu Val Val Ala Ala
                405                 410                 415
Asn

<210> SEQ ID NO 7
<211> LENGTH: 539
<212> TYPE: DNA
<213> ORGANISM: Physcomitrella patens

<400> SEQUENCE: 7
gcacgagcgc acttggtttc tgccacttat tccagctggt aaagaaaaac cacctaaaat    60
gaaagtgttt gaagcagata catttgagaa ggaagtggaa gaaccgaaga tcaaggcctt   120
acctccattg aagtcactta agtacctcc agctttgaag gttgaggaag ctacctacaa   180
ggttgaaagt gaagggaagg tgaacaagag caacattaca gcaagagagt tttccgtcgc   240
agaacttcag gcggctacgg acagtttctc agaggataat ttacttggcg aaggttcgct   300
tggttgtgtt taccgcgcgg agttccccga cggtgaggtt ctagctgtca gaaacttgat   360
acaacagcct ccatggttcg gaatgaagat gatttcttga gcgttgtcga tggcttggcc   420
```

-continued

```
cggctacaat accaattcta atgaactcgt aggctactgt gccgagcatg ggcaacgact      480
tctggtctac aagttcatca gtcgagggac actccatgaa ctgcttcatg gctcagccg      539
```

<210> SEQ ID NO 8
<211> LENGTH: 1468
<212> TYPE: DNA
<213> ORGANISM: Physcomitrella patens

<400> SEQUENCE: 8

```
tttctggaat agctcagaag cgttgcaaaa tttatcagga ggtttgcaga catggtgatg       60
aggaaagtgg gcaagtatga agtggggcga actattggtg agggaacctt cgccaaggtg      120
aaatttgccc agaacaccga gacagggag agcgtggcca tgaaggtgct agatcgtcag       180
acggtgctca agcacaagat ggtagagcag atcaggcgag aaatatccat aatgaagctg      240
gttaggcatc ctaatgttgt ccgattgcac gaggttctgg caagtcgttg caagatttac      300
atcattttgg agtttgtaac gggcggggag cttttttgaca aaattgtgca tcaaggaagg      360
cttaatgaga acgactctcg caaatatttt cagcagctca tggatggagt tgattattgc      420
cacagcaagg gcgtctcaca tcgagatttg aagcctgaaa atctccttct tgattcactg      480
gacaatctca aaatatcaga ttttggtctg agtgctcttc ctcagcaagt gagggaagat      540
ggacttttgc acaccacttg tggtactccc aattatgttg cacctgaggt tcttaatgat      600
aagggctacg atggtgcagt ggctgatatc tggtcttgcg gtgtcatctt gtttgtatta      660
atggctggat ttctcccatt tgatgaggct gacttgaata ctctttacag caagatacga      720
gaggcagatt ttacttgtcc accttggttt tcctccggcg ccaaaacact gattactaat      780
attctggatc ccaatcccct aacacgtatc aggatgagag gaattcggga tgacgaatgg      840
ttcaaaaaga actatgttcc tgttcgtatg tatgacgatg aagatattaa tcttgatgat      900
gtggagactg cttttgatga ttctaaggaa caatttgtga agagcagag ggaggtgaaa       960 gacgtgggtc cgtcgttgat gaatgccttt gaactcataa gcctatctca aggactaaac     1020
ctctctgcgt tgtttgatag acgtcaggac catgtaaagc gccaaactcg tttcacttca     1080
aagaaaccag ctcgagatat aattaataga atggaaaccg ctgcgaagtc gatgggcttt     1140
ggtgttggaa cgcgtaacta caagatgaga ctcgaggcag ctagtgagtg cagaatatca     1200
cagcacttgg ctgtggctat cgaagtgtac gaggtggctc cttctttatt catgattgaa     1260
gtgcggaagg ctgcgggtga tactttggaa tatcacaagt tctataaaag cttttgtacc     1320
cggttgaaag atatcatatg gacaacggca gttgataagg acgaagttaa gacattgacg     1380
ccatctgtag ttaagaataa ataattctgc tccagcatta acttggatga ggagcaagga     1440
tataccgctg catcgagctc cgaagggc                                        1468
```

<210> SEQ ID NO 9
<211> LENGTH: 450
<212> TYPE: PRT
<213> ORGANISM: Physcomitrella patens

<400> SEQUENCE: 9

```
Met Val Met Arg Lys Val Gly Lys Tyr Glu Val Gly Arg Thr Ile Gly
  1               5                  10                  15

Glu Gly Thr Phe Ala Lys Val Lys Phe Ala Gln Asn Thr Glu Thr Gly
             20                  25                  30

Glu Ser Val Ala Met Lys Val Leu Asp Arg Gln Thr Val Leu Lys His
         35                  40                  45
```

-continued

```
Lys Met Val Glu Gln Ile Arg Arg Glu Ile Ser Ile Met Lys Leu Val
    50                  55                  60

Arg His Pro Asn Val Val Arg Leu His Glu Val Leu Ala Ser Arg Cys
65                  70                  75                  80

Lys Ile Tyr Ile Ile Leu Glu Phe Val Thr Gly Gly Glu Leu Phe Asp
                85                  90                  95

Lys Ile Val His Gln Gly Arg Leu Asn Glu Asn Asp Ser Arg Lys Tyr
                100                 105                 110

Phe Gln Gln Leu Met Asp Gly Val Asp Tyr Cys His Ser Lys Gly Val
                115                 120                 125

Ser His Arg Asp Leu Lys Pro Glu Asn Leu Leu Asp Ser Leu Asp
    130                 135                 140

Asn Leu Lys Ile Ser Asp Phe Gly Leu Ser Ala Leu Pro Gln Gln Val
145                 150                 155                 160

Arg Glu Asp Gly Leu Leu His Thr Thr Cys Gly Thr Pro Asn Tyr Val
                165                 170                 175

Ala Pro Glu Val Leu Asn Asp Lys Gly Tyr Asp Gly Ala Val Ala Asp
                180                 185                 190

Ile Trp Ser Cys Gly Val Ile Leu Phe Val Leu Met Ala Gly Phe Leu
        195                 200                 205

Pro Phe Asp Glu Ala Asp Leu Asn Thr Leu Tyr Ser Lys Ile Arg Glu
    210                 215                 220

Ala Asp Phe Thr Cys Pro Pro Trp Phe Ser Ser Gly Ala Lys Thr Leu
225                 230                 235                 240

Ile Thr Asn Ile Leu Asp Pro Asn Pro Leu Thr Arg Ile Arg Met Arg
                245                 250                 255

Gly Ile Arg Asp Asp Glu Trp Phe Lys Lys Asn Tyr Val Pro Val Arg
            260                 265                 270

Met Tyr Asp Asp Glu Asp Ile Asn Leu Asp Asp Val Glu Thr Ala Phe
    275                 280                 285

Asp Asp Ser Lys Glu Gln Phe Val Lys Glu Gln Arg Glu Val Lys Asp
    290                 295                 300

Val Gly Pro Ser Leu Met Asn Ala Phe Glu Leu Ile Ser Leu Ser Gln
305                 310                 315                 320

Gly Leu Asn Leu Ser Ala Leu Phe Asp Arg Arg Gln Asp His Val Lys
                325                 330                 335

Arg Gln Thr Arg Phe Thr Ser Lys Lys Pro Ala Arg Asp Ile Ile Asn
                340                 345                 350

Arg Met Glu Thr Ala Ala Lys Ser Met Gly Phe Gly Val Gly Thr Arg
    355                 360                 365

Asn Tyr Lys Met Arg Leu Glu Ala Ala Ser Glu Cys Arg Ile Ser Gln
    370                 375                 380

His Leu Ala Val Ala Ile Glu Val Tyr Glu Val Ala Pro Ser Leu Phe
385                 390                 395                 400

Met Ile Glu Val Arg Lys Ala Ala Gly Asp Thr Leu Glu Tyr His Lys
                405                 410                 415

Phe Tyr Lys Ser Phe Cys Thr Arg Leu Lys Asp Ile Ile Trp Thr Thr
                420                 425                 430

Ala Val Asp Lys Asp Glu Val Lys Thr Leu Thr Pro Ser Val Val Lys
            435                 440                 445

Asn Lys
450
```

<210> SEQ ID NO 10
<211> LENGTH: 606
<212> TYPE: DNA
<213> ORGANISM: Physcomitrella patens

<400> SEQUENCE: 10

| | | | | | |
|---|---|---|---|---|---|
| ggcacgagat | ttggttgcaa | aataggtaac | tacaacttaa | gaagaaaaac | aatctctctc | 60 |
| tttccccaca | caagatacaa | cttcgctttt | tccatcactt | acaccagaaa | gcccaaagta | 120 |
| gggtagattg | tcacacatcg | ctatgatccc | aattaagcat | ctactacttt | tcatcagatc | 180 |
| agcaaactac | caatcataga | aactaggtga | tgaatattac | gatactttca | ggttcaatgc | 240 |
| gaaatccaag | gttaacagta | atgaatgtat | tcaagctctg | tacatgcatt | aattttatgc | 300 |
| taccagtaga | aaacttcatt | tgacgatgca | gcggtatatc | cttgctcctc | atccaagtta | 360 |
| atgctggagc | agaattattt | attcttaact | acagatggcg | tcaatgtctt | aacttcgtcc | 420 |
| ttatcaactg | ccgttgtcca | tatgatatct | ttcaaccggg | tacaaaagct | tttatagaac | 480 |
| ttgtgatatt | ccaaagtatc | acccgcagcc | ttccgcactt | caatcatgaa | taaagaagga | 540 |
| gccacctcgt | acacttcgat | agcccagcca | agtgctgtga | tattctgcct | cactactgcc | 600 |
| tcgagc | | | | | 606 |

<210> SEQ ID NO 11
<211> LENGTH: 3025
<212> TYPE: DNA
<213> ORGANISM: Physcomitrella patens

<400> SEQUENCE: 11

| | | | | | |
|---|---|---|---|---|---|
| atcccgggtg | tcggaattcg | gtcacaatga | gctagtgtgt | tgtttgattg | tggcctcagc | 60 |
| tggagaggct | ttggtatcgt | tagcagcgag | tgacgctgtt | gaaggattgt | atccatccac | 120 |
| aagcgagaag | ccttgcctaa | tttttgggag | ggaaaggtgg | ttctcacatg | agaggagcag | 180 |
| ttgtcgatgc | cccaatgaag | ggtgacagga | gagcatgcat | tttgggagga | atgggaagac | 240 |
| ctaatggtgg | aaccatcttg | tacgtgttgg | tgatttcatt | cattgctttg | gtgaatggag | 300 |
| ccaccgatcc | gaacgatgtg | tctgctttga | atactatgtt | cactggcttc | aacagcgatc | 360 |
| ctaagctcac | gaactgggtg | caaaacgcgg | gtgatccctg | cggaaccaac | tggctgggcg | 420 |
| ttacttgtga | tgggaccttc | gtcacctcaa | tcaagctatc | caacatggga | ctgaatggga | 480 |
| aggtggaggg | atgggtgttg | cagaagtttc | aacacctctc | tgtgcttgac | cttagccata | 540 |
| ataatcttgc | tagcggaatt | cctgagatgt | ttcctcccaa | gttgactgaa | ctagatttgt | 600 |
| cttacaacca | gctcacgggt | agttttcctt | atttgataat | caacatccct | actttgacaa | 660 |
| gcataaaact | gaataacaac | aagctgagtg | gaacgctcga | tgggcaggtt | ttcagtaaac | 720 |
| tcacaaactt | aatcaccctc | gatatttcca | acaacgcaat | tacagggccg | attcccgagg | 780 |
| gcatgggtga | catggtcagc | ctaagatttt | tgaacatgca | aaataataag | ctgactggac | 840 |
| caatcccaga | cacattggct | aatattccat | ctctagaaac | attggacgta | tctaacaacg | 900 |
| cgcttactgg | ctttctccca | ccaaacctga | acccaaagaa | tttcagatat | ggaggcaatc | 960 |
| cactcaacac | ccaagcccct | cctccaccac | cgtttacacc | accgccacct | tcaaagaatc | 1020 |
| caaagcctat | tcctcctcca | ccccacccct | gtagccgaac | accagatact | gctcctaagg | 1080 |
| ctgaaggcgg | catcgtatca | ggcgcagcaa | ttgctgggat | tgtcgtggga | gcaattttgg | 1140 |
| tgcttgcagc | aattttcata | gctgtatggt | tctttgtcgt | ccgtaaaaga | tctgagctta | 1200 |
| ccaaaccttt | ggatttagag | gctaatcaca | gcagccgacg | cacttggttt | ctgccactta | 1260 |

-continued

```
ttccagctgg taaagaaaaa ccacctaaaa tgaaagtgtt tgaagcagat acatttgaga      1320
aggaagtgga agagccgaag atcaaggcct tacctccatt gaagtcactt aaagtacctc      1380
cagcattgaa ggttgaggaa gctacctaca aggttgaaag tgaagggaag gtgaacaaga      1440
gcaacattac agcaagagag ttttccgtcg cagaacttca ggcggctacg acagtttct       1500 cagaggataa tttacttggc gaaggttcgc ttggttgtgt ttaccgcgcg gagttccccg      1560
acggtgaggt tctagctgtc aagaaacttg atacaacagc ctccatggtt cggaatgaag      1620
atgatttctt gagcgttgtc gatggcttgg cccggctaca acataccaat tctaatgaac      1680
tcgtaggcta ctgtgccgag catgggcaac gacttctggt ctacaagttc atcagtcgag      1740
ggacactcca tgaactgctt catggctcag ccgatagccc caaggagttg tcatggaatg      1800
tccgtgtgaa gattgcactt ggttgtgcgc gggctcttga gtatttccat gaaatcgttt      1860
cgcagccggt tgtgcaccgc aactttagat cctcaaacat tcttttggat gatgagctga      1920
acccacatgt gtcggattgt ggtttggctg cttttacccc atccagtgct gaacggcagg      1980
tctctgccca gtgttgggga tcttttggac acagtccccc tgaattcagc acatctggaa      2040
tgtatgatgt gaaaagcgac gtttatagct ttggtgttgt gatgcttgag cttatgacag      2100
gacgcaagcc tttagacagc tcaagaccaa gatccgagca aaacctggtg cgatgggcaa      2160
caccacaact gcatgatatt gatgcactcg caagaatggt ggatccagcg ttagagggtg      2220
cttaccctgc caagtccctc tcccggttcg ccgacatcgt tgccttgtgt gtccagcccg      2280
aacccgaatt ccgacctcct atatctgaag tagtgcagtc cctggtaagg cttatgcagc      2340
gtgcagcttt aagtaaacgc cggcatgagt acaacgcagg cgttcctcag actgatatgg      2400
aggaccctag tgattacttg tgacagaagt aagtatcctg gtcgatactt cccaatttca      2460
agcatagaga acctcccgcg cgtctactcc cacttgattt tcaaagctgg cgaaaagtgg      2520
ccaaatttgt ggatttgtga caccttgcaa ctaaatcggg gagatattca gcttctttgc      2580
aattccagac catgatggca cagactttgg cttgcatcct cctcattatt actgaagctt      2640
ttgcttctaa tggcggatta ctgattatgg atgactatcc cgtttccagg cagacgtgaa      2700
gagaagtgtt ggcttccgaa gttgttaaat tgtatcgacg gctgaaagct ttttaagag      2760 cttacttctg gtcctagtt agtgatatta aggtccctgt gccttaagag taatgtgcaa      2820
ttcctgttgt gttgcaaact cgggtaacgc tttgtcttgt agttttggca cattacaagg      2880
ttagttcgac agtgaactca caatttgaac agattagtta gggagtgtaa ctctagcaaa      2940
agttgattcc ttgtggttac ccaatttttt gaatgtgaac tcccactcat tggtgtgatg      3000
gagtacatga ttcgcacgag ctcgc                                           3025
```

<210> SEQ ID NO 12  
<211> LENGTH: 751  
<212> TYPE: PRT  
<213> ORGANISM: Physcomitrella patens

<400> SEQUENCE: 12

```
Met Arg Gly Ala Val Val Asp Ala Pro Met Lys Gly Asp Arg Arg Ala
 1               5                  10                  15

Cys Ile Leu Gly Gly Met Gly Arg Pro Asn Gly Gly Thr Ile Leu Tyr
            20                  25                  30

Val Leu Val Ile Ser Phe Ile Ala Leu Val Asn Gly Ala Thr Asp Pro
        35                  40                  45

Asn Asp Val Ser Ala Leu Asn Thr Met Phe Thr Gly Phe Asn Ser Asp
    50                  55                  60
```

-continued

```
Pro Lys Leu Thr Asn Trp Val Gln Asn Ala Gly Asp Pro Cys Gly Thr
 65                  70                  75                  80

Asn Trp Leu Gly Val Thr Cys Asp Gly Thr Phe Val Thr Ser Ile Lys
                 85                  90                  95

Leu Ser Asn Met Gly Leu Asn Gly Lys Val Glu Gly Trp Val Leu Gln
            100                 105                 110

Lys Phe Gln His Leu Ser Val Leu Asp Leu Ser His Asn Asn Leu Ala
        115                 120                 125

Ser Gly Ile Pro Glu Met Phe Pro Pro Lys Leu Thr Glu Leu Asp Leu
    130                 135                 140

Ser Tyr Asn Gln Leu Thr Gly Ser Phe Pro Tyr Leu Ile Ile Asn Ile
145                 150                 155                 160

Pro Thr Leu Thr Ser Ile Lys Leu Asn Asn Asn Lys Leu Ser Gly Thr
                165                 170                 175

Leu Asp Gly Gln Val Phe Ser Lys Leu Thr Asn Leu Ile Thr Leu Asp
            180                 185                 190

Ile Ser Asn Asn Ala Ile Thr Gly Pro Ile Pro Glu Gly Met Gly Asp
        195                 200                 205

Met Val Ser Leu Arg Phe Leu Asn Met Gln Asn Asn Lys Leu Thr Gly
    210                 215                 220

Pro Ile Pro Asp Thr Leu Ala Asn Ile Pro Ser Leu Glu Thr Leu Asp
225                 230                 235                 240

Val Ser Asn Asn Ala Leu Thr Gly Phe Leu Pro Pro Asn Leu Asn Pro
                245                 250                 255

Lys Asn Phe Arg Tyr Gly Gly Asn Pro Leu Asn Thr Gln Ala Pro Pro
            260                 265                 270

Pro Pro Pro Phe Thr Pro Pro Pro Ser Lys Asn Pro Lys Pro Ile
        275                 280                 285

Pro Pro Pro Pro His Pro Gly Ser Arg Thr Pro Asp Thr Ala Pro Lys
    290                 295                 300

Ala Glu Gly Gly Ile Val Ser Gly Ala Ala Ile Ala Gly Ile Val Val
305                 310                 315                 320

Gly Ala Ile Leu Val Leu Ala Ala Ile Phe Ile Ala Val Trp Phe Phe
                325                 330                 335

Val Val Arg Lys Arg Ser Glu Leu Thr Lys Pro Leu Asp Leu Glu Ala
            340                 345                 350

Asn His Ser Ser Arg Arg Thr Trp Phe Leu Pro Leu Ile Pro Ala Gly
        355                 360                 365

Lys Glu Lys Pro Pro Lys Met Lys Val Phe Glu Ala Asp Thr Phe Glu
    370                 375                 380

Lys Glu Val Glu Glu Pro Lys Ile Lys Ala Leu Pro Pro Leu Lys Ser
385                 390                 395                 400

Leu Lys Val Pro Pro Ala Leu Lys Val Glu Glu Ala Thr Tyr Lys Val
                405                 410                 415

Glu Ser Glu Gly Lys Val Asn Lys Ser Asn Ile Thr Ala Arg Glu Phe
            420                 425                 430

Ser Val Ala Glu Leu Gln Ala Ala Thr Asp Ser Phe Ser Glu Asp Asn
        435                 440                 445

Leu Leu Gly Glu Gly Ser Leu Gly Cys Val Tyr Arg Ala Glu Phe Pro
    450                 455                 460

Asp Gly Glu Val Leu Ala Val Lys Lys Leu Asp Thr Thr Ala Ser Met
465                 470                 475                 480
```

```
Val Arg Asn Glu Asp Asp Phe Leu Ser Val Asp Gly Leu Ala Arg
            485                 490                 495

Leu Gln His Thr Asn Ser Asn Glu Leu Val Gly Tyr Cys Ala Glu His
            500                 505                 510

Gly Gln Arg Leu Leu Val Tyr Lys Phe Ile Ser Arg Gly Thr Leu His
            515                 520                 525

Glu Leu Leu His Gly Ser Ala Asp Ser Pro Lys Glu Leu Ser Trp Asn
            530                 535                 540

Val Arg Val Lys Ile Ala Leu Gly Cys Ala Arg Ala Leu Glu Tyr Phe
545                 550                 555                 560

His Glu Ile Val Ser Gln Pro Val Val His Arg Asn Phe Arg Ser Ser
                565                 570                 575

Asn Ile Leu Leu Asp Asp Glu Leu Asn Pro His Val Ser Asp Cys Gly
            580                 585                 590

Leu Ala Ala Phe Thr Pro Ser Ser Ala Glu Arg Gln Val Ser Ala Gln
            595                 600                 605

Val Leu Gly Ser Phe Gly His Ser Pro Pro Glu Phe Ser Thr Ser Gly
            610                 615                 620

Met Tyr Asp Val Lys Ser Asp Val Tyr Ser Phe Gly Val Val Met Leu
625                 630                 635                 640

Glu Leu Met Thr Gly Arg Lys Pro Leu Asp Ser Ser Arg Pro Arg Ser
                645                 650                 655

Glu Gln Asn Leu Val Arg Trp Ala Thr Pro Gln Leu His Asp Ile Asp
            660                 665                 670

Ala Leu Ala Arg Met Val Asp Pro Ala Leu Glu Gly Ala Tyr Pro Ala
            675                 680                 685

Lys Ser Leu Ser Arg Phe Ala Asp Ile Val Ala Leu Cys Val Gln Pro
            690                 695                 700

Glu Pro Glu Phe Arg Pro Pro Ile Ser Glu Val Val Gln Ser Leu Val
705                 710                 715                 720

Arg Leu Met Gln Arg Ala Ala Leu Ser Lys Arg Arg His Glu Tyr Asn
                725                 730                 735

Ala Gly Val Pro Gln Thr Asp Met Glu Asp Pro Ser Asp Tyr Leu
            740                 745                 750

<210> SEQ ID NO 13
<211> LENGTH: 1757
<212> TYPE: DNA
<213> ORGANISM: Brassica napus

<400> SEQUENCE: 13
aacaaaaaaa aatctaaggt ttatcttttt cttcttctat ctgatcatca atcatcgaga      60
gagaaaaaag tatactttt tagatgtgaa gaagctcatc aatcgaagaa gacaatcatc      120
aaatgcttca ctttggttcc ctttcttcat cagaaaactc gaggtagatc agttctttga      180
tgggatggga caccaaatcg ctaagtgtta tgataccagc aactactagt tacgtgctat      240
ctccagagca ataccatgg cttcaaacgg agtaggcagt tcgagatctt ccaaaggtgt       300
gaaggcctct tctagctcag tcgattggtt gaccagagat ttggttgaga tgaggataag      360
ggacaaggtc gagactgatg atgagaggga tagtgaacca gatattattg atggcgctgg      420
cactgaacct ggccatgtga ttagaaccac agtccgtgga cgcaatggtc aatcaagaca      480
gacagtcagt tacatatcag agcatgtagt tggtactggt tcctttggca tggttttttca     540 agccaagtgt agggaaactg gggagattgt tgcaatcaag aaggttctac aagacaagcg      600
```

-continued

```
ttacaagaac agggagctac aaattatgca gatgctagac cacccaatg tcgttgctct    660
aaagcatagc ttctacacga gagctgataa cgaagaggtt tatttgaatc ttgtccttga   720
gtttgtgcct gagaccgtca ataggctgc aagaagttac actaggacga accagctaat    780
gcctttaata tacgttaaac tctacaccta tcagatttgc agggcgcttg cttacatcca   840
taattgcttt ggtctttgtc accgtgatat taagcctcaa aacttgctag tgaacccaca   900
tacgcatcag ctgaaaatct gtgacttcgg gagtgcaaaa gtgttggtga aaggagaacc   960
caatgtttct tacatctgtt ctagatacta tcgtgctcca gaactcattt ttggcgccag  1020
cgaatacaca cctgcaattg atatatggtc aactggttgt gtgatggctg aattgcttct  1080
tggacagcct ctgttccctg gtgaaagcgg agtcgatcag cttgttgaaa tcattaaggt  1140
tttaggtaca ccaacgaggg aggaaatcaa gtgcatgaat ccaaactata cagaatttaa  1200
attcccccag ataaaacctc acccatggca aggtcttc caaaaacgtt taccgccaga    1260
agcggttgat cttctatgta ggttcttcca atattcccct aatctgagat gcacagcttt  1320
ggaagcgtgt attcatccgt tatttgatga gctaagggac ccgaacactc gtcttcccaa  1380
tggccggcca cttcctccgc ttttcaactt caaacctcaa gagctatctg gcatcccttc  1440
tgaaatcgtg aacaggcttg taccagaaca tgcccgtaag cagaacttct tcatggcgtt  1500
ggatgcctaa gcgcttatcc tgtttctttt cttttcttg cttatgtata aactctctag   1560
atatcgggta tttggagcag ccagaaggca ttacacgccc tctttggctt ttttttatca  1620
gtgagttgtt tggttatcgg gacacgatga tgcatgaata caaacagtac ttgaggtcgc  1680
tgctggctta taagaccact tgtttgtttc acaaccagtt cttatatata ttattataca  1740
aaaaaaaaaa aaaaaaa                                                 1757
```

<210> SEQ ID NO 14
<211> LENGTH: 417
<212> TYPE: PRT
<213> ORGANISM: Brassica napus

<400> SEQUENCE: 14

```
Met Ala Ser Asn Gly Val Gly Ser Ser Arg Ser Lys Gly Val Lys
  1               5                  10                  15

Ala Ser Ser Ser Val Asp Trp Leu Thr Arg Asp Leu Val Glu Met
                 20                  25                  30

Arg Ile Arg Asp Lys Val Glu Thr Asp Asp Glu Arg Asp Ser Glu Pro
                 35                  40                  45

Asp Ile Ile Asp Gly Ala Gly Thr Glu Pro Gly His Val Ile Arg Thr
 50                  55                  60

Thr Val Arg Gly Arg Asn Gly Gln Ser Arg Gln Thr Val Ser Tyr Ile
 65                  70                  75                  80

Ser Glu His Val Val Gly Thr Gly Ser Phe Gly Met Val Phe Gln Ala
                 85                  90                  95

Lys Cys Arg Glu Thr Gly Glu Ile Val Ala Ile Lys Lys Val Leu Gln
                100                 105                 110

Asp Lys Arg Tyr Lys Asn Arg Glu Leu Gln Ile Met Gln Met Leu Asp
                115                 120                 125

His Pro Asn Val Val Ala Leu Lys His Ser Phe Tyr Thr Arg Ala Asp
            130                 135                 140

Asn Glu Glu Val Tyr Leu Asn Leu Val Leu Glu Phe Val Pro Glu Thr
145                 150                 155                 160

Val Asn Arg Ala Ala Arg Ser Tyr Thr Arg Thr Asn Gln Leu Met Pro
```

```
                165                 170                 175
Leu Ile Tyr Val Lys Leu Tyr Thr Tyr Gln Ile Cys Arg Ala Leu Ala
            180                 185                 190
Tyr Ile His Asn Cys Phe Gly Leu Cys His Arg Asp Ile Lys Pro Gln
        195                 200                 205
Asn Leu Leu Val Asn Pro His Thr His Gln Leu Lys Ile Cys Asp Phe
    210                 215                 220
Gly Ser Ala Lys Val Leu Val Lys Gly Glu Pro Asn Val Ser Tyr Ile
225                 230                 235                 240
Cys Ser Arg Tyr Tyr Arg Ala Pro Glu Leu Ile Phe Gly Ala Ser Glu
                245                 250                 255
Tyr Thr Pro Ala Ile Asp Ile Trp Ser Thr Gly Cys Val Met Ala Glu
            260                 265                 270
Leu Leu Leu Gly Gln Pro Leu Phe Pro Gly Glu Ser Gly Val Asp Gln
        275                 280                 285
Leu Val Glu Ile Ile Lys Val Leu Gly Thr Pro Thr Arg Glu Glu Ile
    290                 295                 300
Lys Cys Met Asn Pro Asn Tyr Thr Glu Phe Lys Phe Pro Gln Ile Lys
305                 310                 315                 320
Pro His Pro Trp His Lys Val Phe Gln Lys Arg Leu Pro Pro Glu Ala
                325                 330                 335
Val Asp Leu Leu Cys Arg Phe Phe Gln Tyr Ser Pro Asn Leu Arg Cys
            340                 345                 350
Thr Ala Leu Glu Ala Cys Ile His Pro Leu Phe Asp Glu Leu Arg Asp
        355                 360                 365
Pro Asn Thr Arg Leu Pro Asn Gly Arg Pro Leu Pro Pro Leu Phe Asn
    370                 375                 380
Phe Lys Pro Gln Glu Leu Ser Gly Ile Pro Ser Glu Ile Val Asn Arg
385                 390                 395                 400
Leu Val Pro Glu His Ala Arg Lys Gln Asn Phe Phe Met Ala Leu Asp
                405                 410                 415
Ala

<210> SEQ ID NO 15
<211> LENGTH: 1621
<212> TYPE: DNA
<213> ORGANISM: Brassica napus

<400> SEQUENCE: 15
ttttctctct ctctctctct ctccacattt gatgatcatt accaaccaaa ctaattgaaa     60
tccatttgtt ctctctctct ctctctctct ctcacactct cttctctgct cttctctgcg    120
cctctaacgt catggctgac gatagggaga tgccgccggc tgctgtagtt gatggacatg    180
accaagtcac tggccacata atctccacca ccatcggtgg taaaaacgga gaaccaaaac    240
agacaataag ttacatggcg gagcgagttg tcggtacagg ctccttcggg atagtgttcc    300
aggcgaagtg tctggagact ggagaaaccg tggcgataaa gaaggttttg caagacagga    360
ggtacaagaa ccgagagctt cagctgatgc gtgtgatgga ccatccgaat gttgtttgtt    420
tgaagcattg cttcttctcg accacgagca agacgagct gtttctgaac ttggttatgg    480
agtatgtccc tgagagcttg taccgagttc tgaaacatta cagcactgct aaccagagga    540
tgccgcttgt ttatgttaaa ctctatatgt accagatctt cagaggactt gcttacattc    600
acaatgttgc tggagtttgt cacagagatc taaagcctca aaatcttctg gttgatcctc    660
```

```
tgactcatca agtgaagatc tgtgattttg gcagtgcgaa acagcttgtt aaaggtgaag    720
ccaacatctc ttacatatgt tcaagattct accgtgcacc tgaacttata ttcggtgcca    780
ctgagtacac aacttccatt gatatttggt ctgctggttg tgttctcgct gagcttcttc    840
ttggtcagcc actattccct ggagaaaatg ctgtgggtca gctcgttgaa atcatcaaag    900
ttcttggtac accaactcga aagagatcc gttgtatgaa tccacactac acagacttta    960
ggttcccgca gataaaggca catccttggc acaagatttt ccacaaaagg atgcctccag    1020
aagccattga ttttgcatca aggctgcttc agtactctcc aagtcttaga tgcacagcgc    1080
ttgaagcttg tgcacatccg ttctttgatg agcttagaga accaaatgct cgtttaccaa    1140
acggacggcc tttcccgccg ctcttcaact tcaaacaaga ggtagctgga gcttcacctg    1200
agctggtcaa caagttgatt ccagaccata tcaagacgca gttgggtcta agcttcttga    1260
atcagtctgg aacttaaaca aacgatcaaa aagacaagaa cttttttata tataattgta    1320
ccattactca gaaccagaag aaggttagtt gaaggcacgt ggaggacaca gttagaggtt    1380
ttgcctcctc aaaactcgtt ccaggaatga aggtcaaaaa agacaagctt ctctacaacc    1440
tgacttcccc caagcctgca agaaaagcta ctcagttgta tcttcttctt cttcttttgt    1500
cctttttttaa aaatgtttgg ttaaagcaaa gaacaaaatc ttctcttttt gctttattct    1560
tactgcatct gtaaatgagt ttagtcagag attttatat agtaaaaaaa aaaaaaaaa       1620
a                                                                    1621

<210> SEQ ID NO 16
<211> LENGTH: 381
<212> TYPE: PRT
<213> ORGANISM: Brassica napus

<400> SEQUENCE: 16

Met Ala Asp Asp Arg Glu Met Pro Ala Ala Val Val Asp Gly His
 1               5                  10                  15

Asp Gln Val Thr Gly His Ile Ile Ser Thr Thr Ile Gly Gly Lys Asn
                 20                  25                  30

Gly Glu Pro Lys Gln Thr Ile Ser Tyr Met Ala Glu Arg Val Val Gly
         35                  40                  45

Thr Gly Ser Phe Gly Ile Val Phe Gln Ala Lys Cys Leu Glu Thr Gly
     50                  55                  60

Glu Thr Val Ala Ile Lys Lys Val Leu Gln Asp Arg Arg Tyr Lys Asn
 65                  70                  75                  80

Arg Glu Leu Gln Leu Met Arg Val Met Asp His Pro Asn Val Cys
                 85                  90                  95

Leu Lys His Cys Phe Phe Ser Thr Thr Ser Lys Asp Glu Leu Phe Leu
                100                 105                 110

Asn Leu Val Met Glu Tyr Val Pro Glu Ser Leu Tyr Arg Val Leu Lys
            115                 120                 125

His Tyr Ser Thr Ala Asn Gln Arg Met Pro Leu Val Tyr Val Lys Leu
        130                 135                 140

Tyr Met Tyr Gln Ile Phe Arg Gly Leu Ala Tyr Ile His Asn Val Ala
145                 150                 155                 160

Gly Val Cys His Arg Asp Leu Lys Pro Gln Asn Leu Leu Val Asp Pro
                165                 170                 175

Leu Thr His Gln Val Lys Ile Cys Asp Phe Gly Ser Ala Lys Gln Leu
            180                 185                 190

Val Lys Gly Glu Ala Asn Ile Ser Tyr Ile Cys Ser Arg Phe Tyr Arg
```

```
                   195                 200                 205
Ala Pro Glu Leu Ile Phe Gly Ala Thr Glu Tyr Thr Thr Ser Ile Asp
    210                 215                 220

Ile Trp Ser Ala Gly Cys Val Leu Ala Glu Leu Leu Gly Gln Pro
225                 230                 235                 240

Leu Phe Pro Gly Glu Asn Ala Val Gly Gln Leu Val Glu Ile Ile Lys
                245                 250                 255

Val Leu Gly Thr Pro Thr Arg Glu Glu Ile Arg Cys Met Asn Pro His
            260                 265                 270

Tyr Thr Asp Phe Arg Phe Pro Gln Ile Lys Ala His Pro Trp His Lys
        275                 280                 285

Ile Phe His Lys Arg Met Pro Pro Glu Ala Ile Asp Phe Ala Ser Arg
290                 295                 300

Leu Leu Gln Tyr Ser Pro Ser Leu Arg Cys Thr Ala Leu Glu Ala Cys
305                 310                 315                 320

Ala His Pro Phe Phe Asp Glu Leu Arg Glu Pro Asn Ala Arg Leu Pro
                325                 330                 335

Asn Gly Arg Pro Phe Pro Pro Leu Phe Asn Phe Lys Gln Glu Val Ala
            340                 345                 350

Gly Ala Ser Pro Glu Leu Val Asn Lys Leu Ile Pro Asp His Ile Lys
        355                 360                 365

Thr Gln Leu Gly Leu Ser Phe Leu Asn Gln Ser Gly Thr
    370                 375                 380

<210> SEQ ID NO 17
<211> LENGTH: 1654
<212> TYPE: DNA
<213> ORGANISM: Brassica napus

<400> SEQUENCE: 17
cgtcgtcgtc tctctctctt tctttctctt ctccgtgaat catcatcatc atcatcatct     60
tcgtgttttc tcgttaagcc cattttgttt tttttttttc tctggggaaa aactcggctc    120
aaaacgatga atgtgatgcg tagattgacg agtatcgctt ctggacgcgg tttcgtctct    180
tctgataacg taggagagac cgagacgccg agatcgaagc ctaaccaaat tgtgaagag     240 atagaagaga ctacacgaga agactctgtt tctaaaacag aggattctga ttcattacca    300
aaagagatgg gaatcggtga tgacgacaag gataaggacg gtgggattat caagggtaat    360
gggacagagt ctggtcggat cattaccacc acaaagaagg gtctgaacga tcaaagagac    420
aagacaatct cgtacagagc tgaacatgtg attggcactg gctcattcgg tgttgtcttt    480
caggctaagt gcttagagac agaagaaaaa gtagctatca agaaagtgtt gcaagacaag    540
agatacaaga acagagagct tcagatcatg cggatgcttg atcatcctaa tgttgttgac    600
ctcaagcatt ctttcttctc caccactgag aaagatgagc tttatcttaa ccttgttctt    660
gagtatgtac ctgagactat ataccgttct tcaagatctt acaccaagat gaatcaacac    720
atgcccttga tctatattca gctctataca tatcagattt gccgcgcaat gaactatcta    780
catagagttg ttggagtgtg tcaccgtgac attaaacctc agaatctatt ggtcaataat    840
gttacacatg aggtgaaggt atgcgatttt gggagcgcca agatgctgat tccgggagaa    900
cccaatatat cttacatatg ctcaaggtat tacagagctc tgaactcat atttggggta     960 actgagtaca caaccgccat cgatatgtgg tctgttggct gtgtcatggc tgaacttttt   1020
cttggacatc tctgttccc tggagagact agtgttgatc aattggttga gatcattaag   1080
```

-continued

```
attttgggaa caccagcaag agaagagatc agaaacatga atcctcgtta caatgatttt    1140
aagttccctc agatcaaagc tcagccatgg cacaagattt tccggagaca ggtatctcca    1200
gaagcaatgg atcttgcctc tagactcctc cagtactcac caaacctgag atgttcagcg    1260
cttgaagcat gtgcacaccc cttcttcgat gatctgagag acccgagagc atccttgcct    1320
aatggaagag cacttcctcc actgtttgat tcacagctc aagaactggc tggtgcatct     1380
gttgaattgc gtcatcgctt aatccctgaa catgcaagga ataacttac tttgtctaac     1440 gagaccgctt cttctctaca cagatgttga tatctaaatt ccttttttt tggcattgtt     1500 ctggttatga acaccctcat tgacctctgc aaccaccttg cactagcagt tccaaaagtg    1560
tatgatttgt taagtttgta actttgtaga ctccattgtt gcagacagaa aatgcagaat    1620
tttccgagtt tgtctcaaaa aaaaaaaaaa aaaa                                1654
```

<210> SEQ ID NO 18
<211> LENGTH: 432
<212> TYPE: PRT
<213> ORGANISM: Brassica napus

<400> SEQUENCE: 18

```
Met Asn Val Met Arg Arg Leu Thr Ser Ile Ala Ser Gly Arg Gly Phe
 1               5                  10                  15

Val Ser Ser Asp Asn Val Gly Glu Thr Glu Thr Pro Arg Ser Lys Pro
            20                  25                  30

Asn Gln Ile Cys Glu Glu Ile Glu Glu Thr Thr Arg Glu Asp Ser Val
        35                  40                  45

Ser Lys Thr Glu Asp Ser Asp Ser Leu Pro Lys Glu Met Gly Ile Gly
    50                  55                  60

Asp Asp Lys Asp Lys Asp Gly Gly Ile Ile Lys Gly Asn Gly Thr
 65                 70                  75                  80

Glu Ser Gly Arg Ile Ile Thr Thr Lys Lys Gly Leu Asn Asp Gln
                85                  90                  95

Arg Asp Lys Thr Ile Ser Tyr Arg Ala Glu His Val Ile Gly Thr Gly
            100                 105                 110

Ser Phe Gly Val Val Phe Gln Ala Lys Cys Leu Glu Thr Glu Glu Lys
        115                 120                 125

Val Ala Ile Lys Lys Val Leu Gln Asp Lys Arg Tyr Lys Asn Arg Glu
    130                 135                 140

Leu Gln Ile Met Arg Met Leu Asp His Pro Asn Val Val Asp Leu Lys
145                 150                 155                 160

His Ser Phe Phe Ser Thr Thr Glu Lys Asp Glu Leu Tyr Leu Asn Leu
                165                 170                 175

Val Leu Glu Tyr Val Pro Glu Thr Ile Tyr Arg Ser Ser Arg Ser Tyr
            180                 185                 190

Thr Lys Met Asn Gln His Met Pro Leu Ile Tyr Ile Gln Leu Tyr Thr
        195                 200                 205

Tyr Gln Ile Cys Arg Ala Met Asn Tyr Leu His Arg Val Val Gly Val
    210                 215                 220

Cys His Arg Asp Ile Lys Pro Gln Asn Leu Leu Val Asn Val Thr
225                 230                 235                 240

His Glu Val Lys Val Cys Asp Phe Gly Ser Ala Lys Met Leu Ile Pro
                245                 250                 255

Gly Glu Pro Asn Ile Ser Tyr Ile Cys Ser Arg Tyr Tyr Arg Ala Pro
            260                 265                 270
```

```
Glu Leu Ile Phe Gly Val Thr Glu Tyr Thr Thr Ala Ile Asp Met Trp
            275                 280                 285

Ser Val Gly Cys Val Met Ala Glu Leu Phe Leu Gly His Pro Leu Phe
290                 295                 300

Pro Gly Glu Thr Ser Val Asp Gln Leu Val Glu Ile Ile Lys Ile Leu
305                 310                 315                 320

Gly Thr Pro Ala Arg Glu Glu Ile Arg Asn Met Asn Pro Arg Tyr Asn
                325                 330                 335

Asp Phe Lys Phe Pro Gln Ile Lys Ala Gln Pro Trp His Lys Ile Phe
            340                 345                 350

Arg Arg Gln Val Ser Pro Glu Ala Met Asp Leu Ala Ser Arg Leu Leu
        355                 360                 365

Gln Tyr Ser Pro Asn Leu Arg Cys Ser Ala Leu Glu Ala Cys Ala His
    370                 375                 380

Pro Phe Phe Asp Asp Leu Arg Asp Pro Arg Ala Ser Leu Pro Asn Gly
385                 390                 395                 400

Arg Ala Leu Pro Pro Leu Phe Asp Phe Thr Ala Gln Glu Leu Ala Gly
                405                 410                 415

Ala Ser Val Glu Leu Arg His Arg Leu Ile Pro Glu His Ala Arg Lys
            420                 425                 430

<210> SEQ ID NO 19
<211> LENGTH: 2400
<212> TYPE: DNA
<213> ORGANISM: Brassica napus

<400> SEQUENCE: 19
gttttggcat ctggagaggg agagagagag agagaaaggg gaataagatg atggagaatc      60
gagtggtggt ggtggctgct ctgtttgcgg tctgcattgt aggatttgag tttagcttca     120
tccatggagc cactgatgca tcagacactt cagcattgaa catgttgttc accagtatgc     180
attcaccagg acagttaaca caatggactg catcaggtgg ggatccttgt gttcagaact     240
ggagaggcgt tacttgctcc aaatcacgaa ttactcaatt aaagttatca ggtcttgagc     300
tctctggaac acttgggtac atgcttgata aattgacttc tcttacagag cttgatctaa     360
gcagcaataa tcttggaggt gatttaccat atcagcttcc tccaaatctg caacggttga     420
atcttgcaaa caaccaattc actggagctg ctcaatactc catttctaat atggcatcac     480
ttaagtatct taatcttggt cacaaccagt ttaaggggca agtagctgtg gacttctcca     540
agctcacctc tcttacaacc ttggacttct ctttcaactc tttcacatcg tctctaccgg     600 gaactttttac ttctcttaca agtttaaagt ccctataccct tcagaacaat cagttctcag     660
gaacactcaa tgtattagcc ggtcttcctc ttgagaccct gaacattgca acaatgact      720 tcaccggctg gatccccagt accttaaagg gtactaattt aataaaagat ggtaactcgt     780
tcaataatgg acctgcacca ccaccaccac ctggtacacc tccaatccac cgctcaccga     840
gccataaatc cggaggaggt tcaaaccgtg attctaccag caatggagat tccaagaaat     900
caggaattgg agctggtgct atagcaggta taatcatttc attactagta gttacagctc     960
ttgtggcttt cttcttagtc aaaagaagaa gaagatcaaa gagatcatca tctatggaca    1020
ttgagaaaac tgacaaccag cctttcactc ttcctccaag cgactttcac gaaacaatt     1080 ctattcagag ttcttcatca attgagacaa agaaacttga tcttccttg tctattaatc    1140 tccgtcctcc accagctgat cgatcatttg atgatgatga ggattctacg agaaagccta    1200
tagttgtcaa gaaatccacc gtggctgttc cctcgaatgt gagagtttac tcagttgctg    1260
```

-continued

```
atcttcagat tgccactgcc agtttcagtg ttgataatct tcttggagaa ggcacttttg    1320
gaagagtata cagagctgag tttaacaatg gaaaggttct tgctgtgaag aagattgatt    1380
catctgctct tccacatagc atgactgatg atttcaccga aatagtatcg aaaatagccg    1440
ttttggatca tccaaatgtg acaaagcttg ttggctactg tgctgaacac ggacaacatc    1500
tcctggtcta tgagttccac agcaaaggat cgttacatga cttcctacac ttatcagaag    1560
aagaaagcaa agcattggtg tggaactcgc gagtcaaggt cgcacttggg actgcacggg    1620
caatagagta cttgcatgaa gtttgttcac cgtctatagt tgacaagaac atcaaatcag    1680
ccaatatttt gcttgattcg gagatgaatc ctcacttatc agacacaggt ctcgcaagct    1740
tcctccccac agcaaatgag ttactaaacc aaaccgatga aggttatagc gcaccggaag    1800
tatcaatgtc aggtcaatac tctttgaaga gtgatgttta cagttttgga gtagtgatgc    1860
ttgaactttt aaccgggagg aaaccattcg acagcacaag gtcaagatct gagcagtcat    1920
tggttagatg ggcgacacca cagcttcatg acattgatgc tttaggcaaa atggttgatc    1980
cagctcttga aggactttat ccggttaaat ctctttctcg gtttgcagat gttattgctc    2040
tctgcgtcca gccagagcca gagtttagac caccaatgtc tgaagttgtg cagtcactgg    2100
ttgtgttagt gcagagagct aacatgagca agagaactgt tggagttgat ccatcacagc    2160
gttctggtag tgctgagcca agcaacgatt acatgtaaac ccattaccac agagagagaa    2220
aaaaagaaca ctttgctccc tatgggatga agtcattgtt tttattgtaa tatgtttgat    2280
aaaccttcac acagtatatt atccccattg tattttgttg taatgtgttt ccaaatttgt    2340
agcttttaga tcattgaaat gaacaaatat tctttcttgt gtaaaaaaaa aaaaaaaaa     2400
```

<210> SEQ ID NO 20
<211> LENGTH: 716
<212> TYPE: PRT
<213> ORGANISM: Brassica napus

<400> SEQUENCE: 20

```
Met Met Glu Asn Arg Val Val Val Ala Ala Leu Phe Ala Val Cys
  1               5                  10                  15

Ile Val Gly Phe Glu Phe Ser Phe Ile His Gly Ala Thr Asp Ala Ser
                 20                  25                  30

Asp Thr Ser Ala Leu Asn Met Leu Phe Thr Ser Met His Ser Pro Gly
             35                  40                  45

Gln Leu Thr Gln Trp Thr Ala Ser Gly Gly Asp Pro Cys Val Gln Asn
         50                  55                  60

Trp Arg Gly Val Thr Cys Ser Lys Ser Arg Ile Thr Gln Leu Lys Leu
 65                  70                  75                  80

Ser Gly Leu Glu Leu Ser Gly Thr Leu Gly Tyr Met Leu Asp Lys Leu
                 85                  90                  95

Thr Ser Leu Thr Glu Leu Asp Leu Ser Ser Asn Asn Leu Gly Gly Asp
                100                 105                 110

Leu Pro Tyr Gln Leu Pro Pro Asn Leu Gln Arg Leu Asn Leu Ala Asn
            115                 120                 125

Asn Gln Phe Thr Gly Ala Ala Gln Tyr Ser Ile Ser Asn Met Ala Ser
        130                 135                 140

Leu Lys Tyr Leu Asn Leu Gly His Asn Gln Phe Lys Gly Gln Val Ala
145                 150                 155                 160

Val Asp Phe Ser Lys Leu Thr Ser Leu Thr Thr Leu Asp Phe Ser Phe
                165                 170                 175
```

```
Asn Ser Phe Thr Ser Ser Leu Pro Gly Thr Phe Thr Ser Leu Thr Ser
            180                 185                 190

Leu Lys Ser Leu Tyr Leu Gln Asn Asn Gln Phe Ser Gly Thr Leu Asn
        195                 200                 205

Val Leu Ala Gly Leu Pro Leu Glu Thr Leu Asn Ile Ala Asn Asn Asp
    210                 215                 220

Phe Thr Gly Trp Ile Pro Ser Thr Leu Lys Gly Thr Asn Leu Ile Lys
225                 230                 235                 240

Asp Gly Asn Ser Phe Asn Asn Gly Pro Ala Pro Pro Pro Pro Pro Gly
                245                 250                 255

Thr Pro Pro Ile His Arg Ser Pro Ser His Lys Ser Gly Gly Gly Ser
                260                 265                 270

Asn Arg Asp Ser Thr Ser Asn Gly Asp Ser Lys Lys Ser Gly Ile Gly
                275                 280                 285

Ala Gly Ala Ile Ala Gly Ile Ile Ile Ser Leu Leu Val Val Thr Ala
            290                 295                 300

Leu Val Ala Phe Phe Leu Val Lys Arg Arg Arg Ser Lys Arg Ser
305                 310                 315                 320

Ser Ser Met Asp Ile Glu Lys Thr Asp Asn Gln Pro Phe Thr Leu Pro
                325                 330                 335

Pro Ser Asp Phe His Glu Asn Asn Ser Ile Gln Ser Ser Ser Ser Ile
                340                 345                 350

Glu Thr Lys Lys Leu Asp Thr Ser Leu Ser Ile Asn Leu Arg Pro Pro
            355                 360                 365

Pro Ala Asp Arg Ser Phe Asp Asp Glu Asp Ser Thr Arg Lys Pro
    370                 375                 380

Ile Val Val Lys Lys Ser Thr Val Ala Val Pro Ser Asn Val Arg Val
385                 390                 395                 400

Tyr Ser Val Ala Asp Leu Gln Ile Ala Thr Ala Ser Phe Ser Val Asp
                405                 410                 415

Asn Leu Gly Glu Gly Thr Phe Gly Arg Val Tyr Arg Ala Glu Phe
                420                 425                 430

Asn Asn Gly Lys Val Leu Ala Val Lys Lys Ile Asp Ser Ser Ala Leu
        435                 440                 445

Pro His Ser Met Thr Asp Asp Phe Thr Glu Ile Val Ser Lys Ile Ala
    450                 455                 460

Val Leu Asp His Pro Asn Val Thr Lys Leu Val Gly Tyr Cys Ala Glu
465                 470                 475                 480

His Gly Gln His Leu Leu Val Tyr Glu Phe His Ser Lys Gly Ser Leu
                485                 490                 495

His Asp Phe Leu His Leu Ser Glu Glu Ser Lys Ala Leu Val Trp
                500                 505                 510

Asn Ser Arg Val Lys Val Ala Leu Gly Thr Ala Arg Ala Ile Glu Tyr
        515                 520                 525

Leu His Glu Val Cys Ser Pro Ser Ile Val Asp Lys Asn Ile Lys Ser
    530                 535                 540

Ala Asn Ile Leu Leu Asp Ser Glu Met Asn Pro His Leu Ser Asp Thr
545                 550                 555                 560

Gly Leu Ala Ser Phe Leu Pro Thr Ala Asn Glu Leu Leu Asn Gln Thr
                565                 570                 575

Asp Glu Gly Tyr Ser Ala Pro Glu Val Ser Met Ser Gly Gln Tyr Ser
                580                 585                 590
```

```
Leu Lys Ser Asp Val Tyr Ser Phe Gly Val Val Met Leu Glu Leu Leu
        595                 600                 605
Thr Gly Arg Lys Pro Phe Asp Ser Thr Arg Ser Arg Ser Glu Gln Ser
    610                 615                 620
Leu Val Arg Trp Ala Thr Pro Gln Leu His Asp Ile Asp Ala Leu Gly
625                 630                 635                 640
Lys Met Val Asp Pro Ala Leu Glu Gly Leu Tyr Pro Val Lys Ser Leu
                645                 650                 655
Ser Arg Phe Ala Asp Val Ile Ala Leu Cys Val Gln Pro Glu Pro Glu
            660                 665                 670
Phe Arg Pro Pro Met Ser Glu Val Val Gln Ser Leu Val Val Leu Val
        675                 680                 685
Gln Arg Ala Asn Met Ser Lys Arg Thr Val Gly Val Asp Pro Ser Gln
    690                 695                 700
Arg Ser Gly Ser Ala Glu Pro Ser Asn Asp Tyr Met
705                 710                 715

<210> SEQ ID NO 21
<211> LENGTH: 1499
<212> TYPE: DNA
<213> ORGANISM: Glycine max

<400> SEQUENCE: 21
tttagagaga gaaagagtgt gagtgttgtg ttgagtgcag tttctttctc acatggcctc     60
tatgccgttg gggccgcagc aacagcttcc accgccgccg ccgcaacaac cgccgccagc    120
ggagaatgac gcgatgaaag tggactctcg cggcggctcc gacgccggca ccgaaaagga    180
aatgtcagct cctgtcgcag atggtaatga tgcactcact ggtcacataa tctcaaccac    240
aattgcaggc aaaaatggcg aacctaaaca aaccatcagt tacatggccg aacgtgttgt    300
tggcactgga tcatttggca ttgttttcca ggcgaagtgc ttggagactg gcgaggcagt    360
ggctataaag aaggtcttgc aggacaggcg atacaaaaat cgtgaactgc agttaatgcg    420
cgtgatggat cacccaaata taatttcctt gagtaactat ttcttctcta caacaagtag    480
agatgaactt tttctgaact tggtgatgga atatgtccct gagacgatct tccgtgttat    540
aaagcactac agtagcatga acagagaat gcccctaatc tatgtgaaat tatatacata    600
tcaaatcttt aggggactgg cgtatatcca tactgtacca ggaatctgcc atagggattt    660
gaagcctcaa aatctttttgg ttgatcgact cacacaccaa gtcaagctct gtgattttgg    720
gagtgcaaaa gttctggtgg agggtgaatc aaacatttca tacatatgtt cacggtacta    780
tcgtgcccca gagctaatat ttggtgcggc agaatacaca acttctgttg atatttggtc    840
cgctggttgt gtccttgcgg aacttcttct aggccagcct ttgttcccag agaaaatca    900
ggttgaccaa ctcgtggaaa ttatcaagat tcttggcact cctactcgag aagaaattcg    960
atgcatgaat cctaattata cagatttcag attcccccat atcaaagctc atccttggca   1020
taaggttttt cacaagcgaa tgcctcctga agcaattgac cttgcatcaa ggcttctcca   1080
atattcccca aaacttcgtt acagtgcagt ggaagcaatg gcacatcctt tctttgacga   1140
gcttcgcgag cccaatgccc ggctacctaa tggtcgtcca ctgcctccac ttttcaactt   1200
taaacaggaa ttagatggag cgcccccga actgcttcct aagctcatcc cagagcatgt   1260
caggcggcaa acccaaatgt aaagagatag taaaacatag agtgaactgt tctagtggat   1320
tagtgtgaaa tacatgagag cttgcttgtg gtcaatagaa caggggttag cccaaatat   1380
gcagtttttc tccccttgt gaagatgtat acatgtgctg gaaaactcag tgtaacccgg   1440
```
aaatgtagat tatgtctaat gtctaatatt tcattctagt taaaaaaaaa aaaaaaaaa    1499

<210> SEQ ID NO 22
<211> LENGTH: 409
<212> TYPE: PRT
<213> ORGANISM: Glycine max

<400> SEQUENCE: 22

```
Met Ala Ser Met Pro Leu Gly Pro Gln Gln Gln Leu Pro Pro Pro
 1               5                  10                  15

Pro Gln Gln Pro Pro Pro Ala Glu Asn Asp Ala Met Lys Val Asp Ser
                20                  25                  30

Arg Gly Gly Ser Asp Ala Gly Thr Glu Lys Glu Met Ser Ala Pro Val
            35                  40                  45

Ala Asp Gly Asn Asp Ala Leu Thr Gly His Ile Ile Ser Thr Thr Ile
        50                  55                  60

Ala Gly Lys Asn Gly Glu Pro Lys Gln Thr Ile Ser Tyr Met Ala Glu
 65                 70                  75                  80

Arg Val Val Gly Thr Gly Ser Phe Gly Ile Val Phe Gln Ala Lys Cys
                85                  90                  95

Leu Glu Thr Gly Glu Ala Val Ala Ile Lys Lys Val Leu Gln Asp Arg
               100                 105                 110

Arg Tyr Lys Asn Arg Glu Leu Gln Leu Met Arg Val Met Asp His Pro
           115                 120                 125

Asn Ile Ile Ser Leu Ser Asn Tyr Phe Phe Ser Thr Thr Ser Arg Asp
       130                 135                 140

Glu Leu Phe Leu Asn Leu Val Met Glu Tyr Val Pro Glu Thr Ile Phe
145                 150                 155                 160

Arg Val Ile Lys His Tyr Ser Ser Met Lys Gln Arg Met Pro Leu Ile
                165                 170                 175

Tyr Val Lys Leu Tyr Thr Tyr Gln Ile Phe Arg Gly Leu Ala Tyr Ile
            180                 185                 190

His Thr Val Pro Gly Ile Cys His Arg Asp Leu Lys Pro Gln Asn Leu
        195                 200                 205

Leu Val Asp Arg Leu Thr His Gln Val Lys Leu Cys Asp Phe Gly Ser
    210                 215                 220

Ala Lys Val Leu Val Glu Gly Glu Ser Asn Ile Ser Tyr Ile Cys Ser
225                 230                 235                 240

Arg Tyr Tyr Arg Ala Pro Glu Leu Ile Phe Gly Ala Ala Glu Tyr Thr
                245                 250                 255

Thr Ser Val Asp Ile Trp Ser Ala Gly Cys Val Leu Ala Glu Leu Leu
            260                 265                 270

Leu Gly Gln Pro Leu Phe Pro Gly Glu Asn Gln Val Asp Gln Leu Val
        275                 280                 285

Glu Ile Ile Lys Ile Leu Gly Thr Pro Thr Arg Glu Ile Arg Cys
    290                 295                 300

Met Asn Pro Asn Tyr Thr Asp Phe Arg Phe Pro His Ile Lys Ala His
305                 310                 315                 320

Pro Trp His Lys Val Phe His Lys Arg Met Pro Pro Glu Ala Ile Asp
                325                 330                 335

Leu Ala Ser Arg Leu Leu Gln Tyr Ser Pro Lys Leu Arg Tyr Ser Ala
            340                 345                 350

Val Glu Ala Met Ala His Pro Phe Phe Asp Glu Leu Arg Glu Pro Asn
        355                 360                 365
```

Ala Arg Leu Pro Asn Gly Arg Pro Leu Pro Pro Leu Phe Asn Phe Lys
    370                 375                 380

Gln Glu Leu Asp Gly Ala Pro Pro Glu Leu Leu Pro Lys Leu Ile Pro
385                 390                 395                 400

Glu His Val Arg Arg Gln Thr Gln Met
            405

<210> SEQ ID NO 23
<211> LENGTH: 1523
<212> TYPE: DNA
<213> ORGANISM: Glycine max

<400> SEQUENCE: 23

| | | | | | |
|---|---|---|---|---|---|
| agacaccaca | aagtgtaact | tgagtgatta | tatctgatga | gtgcagaaag | aagggaggat | 60 |
| tgttggtgat | cgatcatcga | tcatcgatca | tcgatcatcg | atggcgtctg | ctagccttgg | 120 |
| aagtggtggg | gtgggcagtt | ccaggtctgt | taatggtggc | ttcagggtt | cttccagttc | 180 |
| cgtcgattgg | cttggcagag | agatgcttga | gatgtctttg | agagaccacg | aggacgatag | 240 |
| agatagtgag | cctgacatca | ttgatggttt | gggtgctgag | actggtcacg | tgataagaac | 300 |
| cagcgttggt | ggccgaaatg | gtcaatctaa | gcagaatgtt | agttatattt | ctgagcatgt | 360 |
| tgtgggaaca | ggctcttttg | gtgttgtttt | tcaagccaaa | tgtagagaaa | cgggagaaat | 420 |
| tgtggccatc | aagaaagttc | tccaggacaa | gcgctacaag | aatagagagt | tacaaattat | 480 |
| gcaaatgctg | gatcatccaa | atattgttgc | ccttaggcat | tgtttctatt | caacgactga | 540 |
| caaagaagaa | gtttacttga | atcttgtact | tgaatatgtt | cctgaaactg | tgaatcgcat | 600 |
| cgccaggagc | tatagcagga | ttaaccagcg | aatgccttta | atatatgtaa | agctttatac | 660 |
| ctaccagatt | tgcagggccc | ttgcttatat | acataactgc | attggtatat | gtcatcgtga | 720 |
| catcaaacct | cagaacctac | ttgtgaaccc | gcacactcat | cagctgaaac | tatgtgatt | 780 |
| tgggagtgca | aaagtgttgg | tgaaaggaga | acctaatgtt | tcttacatct | gttcaagata | 840 |
| ctaccgtgct | ccggaactta | tatttggggc | cactgaatat | acaactgcca | tagatatatg | 900 |
| gtcaactggt | tgtgtaatgg | ctgaattact | tcttggacag | cccttgtttc | ctggagagag | 960 |
| tggagttgat | cagctagttg | aaatcatcaa | ggttttggga | actccaacca | gggaggagat | 1020 |
| aaagtgcatg | aacccaaatt | atactgaatt | taagtttcca | cagataaaac | ctcatccatg | 1080 |
| gcacaaggtt | tttcagaaac | gtttaccccc | agaagcagtg | gaccttgtct | gtaggttctt | 1140 |
| tcagtactct | cccaatttga | gatgcactgc | attggaagct | tgcattcatc | catttttga | 1200 |
| tgaattgagg | gacccaaaca | cccgccttcc | taatggtcga | ccacttcctc | cactgtttaa | 1260 |
| ttttaaacct | caggaacttt | ctggtgtacc | ccctgatgtc | atcaatcggc | ttattccaga | 1320 |
| gcatgcgcgt | aaacagaact | tatttatggc | tttgcacacc | tagcaattcc | cgtaccctcc | 1380 |
| taagttgtcg | tcacttacta | gcaggttgta | aattatccgg | tttatccgag | aaaaactcca | 1440 |
| cagaaagagt | tactaggatt | atattattat | tatataatat | gaaaagtttc | ttttttcttt | 1500 |
| tttggaaaaa | aaaaaaaaaa | aaa | | | | 1523 |

<210> SEQ ID NO 24
<211> LENGTH: 420
<212> TYPE: PRT
<213> ORGANISM: Glycine max

<400> SEQUENCE: 24

Met Ala Ser Ala Ser Leu Gly Ser Gly Gly Val Gly Ser Ser Arg Ser

-continued

```
  1               5              10              15
Val Asn Gly Gly Phe Arg Gly Ser Ser Ser Val Asp Trp Leu Gly
             20              25              30

Arg Glu Met Leu Glu Met Ser Leu Arg Asp His Glu Asp Arg Asp
             35              40              45

Ser Glu Pro Asp Ile Ile Asp Gly Leu Gly Ala Glu Thr Gly His Val
             50              55              60

Ile Arg Thr Ser Val Gly Gly Arg Asn Gly Gln Ser Lys Gln Asn Val
 65              70              75              80

Ser Tyr Ile Ser Glu His Val Val Gly Thr Gly Ser Phe Gly Val Val
                 85              90              95

Phe Gln Ala Lys Cys Arg Glu Thr Gly Glu Ile Val Ala Ile Lys Lys
             100             105             110

Val Leu Gln Asp Lys Arg Tyr Lys Asn Arg Glu Leu Gln Ile Met Gln
             115             120             125

Met Leu Asp His Pro Asn Ile Val Ala Leu Arg His Cys Phe Tyr Ser
             130             135             140

Thr Thr Asp Lys Glu Glu Val Tyr Leu Asn Leu Val Leu Glu Tyr Val
145             150             155             160

Pro Glu Thr Val Asn Arg Ile Ala Arg Ser Tyr Ser Arg Ile Asn Gln
                 165             170             175

Arg Met Pro Leu Ile Tyr Val Lys Leu Tyr Thr Tyr Gln Ile Cys Arg
                 180             185             190

Ala Leu Ala Tyr Ile His Asn Cys Ile Gly Ile Cys His Arg Asp Ile
             195             200             205

Lys Pro Gln Asn Leu Leu Val Asn Pro His Thr His Gln Leu Lys Leu
             210             215             220

Cys Asp Phe Gly Ser Ala Lys Val Leu Val Lys Gly Glu Pro Asn Val
225             230             235             240

Ser Tyr Ile Cys Ser Arg Tyr Tyr Arg Ala Pro Glu Leu Ile Phe Gly
                 245             250             255

Ala Thr Glu Tyr Thr Thr Ala Ile Asp Ile Trp Ser Thr Gly Cys Val
                 260             265             270

Met Ala Glu Leu Leu Leu Gly Gln Pro Leu Phe Pro Gly Glu Ser Gly
             275             280             285

Val Asp Gln Leu Val Glu Ile Ile Lys Val Leu Gly Thr Pro Thr Arg
             290             295             300

Glu Glu Ile Lys Cys Met Asn Pro Asn Tyr Thr Glu Phe Lys Phe Pro
305             310             315             320

Gln Ile Lys Pro His Pro Trp His Lys Val Phe Gln Lys Arg Leu Pro
                 325             330             335

Pro Glu Ala Val Asp Leu Val Cys Arg Phe Phe Gln Tyr Ser Pro Asn
                 340             345             350

Leu Arg Cys Thr Ala Leu Glu Ala Cys Ile His Pro Phe Phe Asp Glu
             355             360             365

Leu Arg Asp Pro Asn Thr Arg Leu Pro Asn Gly Arg Pro Leu Pro Pro
             370             375             380

Leu Phe Asn Phe Lys Pro Gln Glu Leu Ser Gly Val Pro Pro Asp Val
385             390             395             400

Ile Asn Arg Leu Ile Pro Glu His Ala Arg Lys Gln Asn Leu Phe Met
                 405             410             415

Ala Leu His Thr
             420
```

<210> SEQ ID NO 25
<211> LENGTH: 1744
<212> TYPE: DNA
<213> ORGANISM: Glycine max

<400> SEQUENCE: 25

| | | | | | |
|---|---|---|---|---|---|
| agagagagaa | acgaagaaga | agagtgtttc | tcacatcaca | tggcctcctt | gcccttgggg | 60 |
| caccaccacc | accaccacaa | accggcggcg | gcggctatac | atccgtcgca | accgccgcag | 120 |
| tctcagccgc | aacccgaagt | tcctcgccgg | agctccgatg | tggagaccga | taaggatatg | 180 |
| tcagctactg | tcattgaggg | gaatgatgct | gtcactggcc | acataatctc | caccacaatt | 240 |
| ggaggcaaaa | atggggaacc | taaagagacc | atcagttaca | tggcagaacg | tgttgttggc | 300 |
| actggatcat | ttggagttgt | ttttcaggca | aagtgcttgg | agactggaga | agcagtggct | 360 |
| attaaaaagg | tcttgcaaga | caggcggtac | aaaaatcgtg | aattgcagtt | aatgcgctta | 420 |
| atggatcacc | ctaatgtaat | ttccctgaag | cactgtttct | tctccacaac | aagcagagat | 480 |
| gaacttttc | taaacttggt | aatggaatat | gttcccgaat | caatgtaccg | agttataaag | 540 |
| cactacacta | ctatgaacca | gagaatgcct | ctcatctatg | tgaaactgta | tacatatcaa | 600 |
| atctttaggg | gattagcata | tatccatacc | gcactgggag | tttgccatag | ggatgtgaag | 660 |
| cctcaaaatc | ttttggttca | tcctcttact | caccaagtta | agctatgtga | ttttgggagt | 720 |
| gccaaagttc | tggtcaaggg | tgaatcaaac | atttcataca | tatgttcacg | ttactatcgg | 780 |
| gctccagaac | taatatttgg | tgcaacagaa | tacacagctt | ctattgatat | ctggtcagct | 840 |
| ggttgtgttc | ttgctgaact | tcttctagga | cagccattat | ttcctggaga | aaaccaagtg | 900 |
| gaccaacttg | tggaaattat | caaggttctt | ggtactccaa | cacgcgagga | aatccgttgt | 960 |
| atgaacccaa | attatacaga | gtttagattc | cctcagatta | aagctcatcc | ttggcacaag | 1020 |
| gttttccaca | agcgaatgcc | tcctgaagca | attgaccttg | catcaaggct | tctccaatat | 1080 |
| tcacctagtc | tccgctgcac | tgcgctggaa | gcatgtgcac | atcctttctt | tgatgagctt | 1140 |
| cgcgaaccaa | atgcccggct | acctaatggc | cgtccactgc | ccccactttt | caacttcaaa | 1200 |
| caggagttag | ctggagcatc | acctgaactg | atcaataggc | tcatcccaga | gcatattagg | 1260 |
| cggcagatgg | gtctcagctt | cccgcattct | gccggtacat | agatgtaaag | ggataatgaa | 1320 |
| acgatgagtc | aacctacata | gtgatcgatg | tgaatcaaca | gaagggctgt | tgaggccta | 1380 |
| tgtataactg | ggagtcccaa | cataatatgc | agtttttcct | ccccccttgtg | aagatgtata | 1440 |
| catgtgttgg | ttgctcggta | aagcttgaaa | gttggtgatt | ctgtgtagta | tttcattcaa | 1500 |
| gttaaagcat | acttatccct | gcatctgtat | attgttttgg | tcagatttca | gaaagctagg | 1560 |
| agtataaaat | gatagcaatc | atgtcttcat | aggtagaggg | gcccagctga | attgaggggc | 1620 |
| ccctatagta | gtttggcttg | cttttttatga | gattaaattc | aggatgtcgt | ttatattatg | 1680 |
| tttataacaa | tctcttgatt | caaaacaaga | aattttctcg | ttgttgaaaa | aaaaaaaaaa | 1740 |
| aaaa | | | | | | 1744 |

<210> SEQ ID NO 26
<211> LENGTH: 420
<212> TYPE: PRT
<213> ORGANISM: Glycine max

<400> SEQUENCE: 26

Met Ala Ser Leu Pro Leu Gly His His His His His Lys Pro Ala
1               5                   10                  15

-continued

```
Ala Ala Ala Ile His Pro Ser Gln Pro Pro Gln Ser Gln Pro Gln Pro
         20                  25                  30
Glu Val Pro Arg Arg Ser Ser Asp Val Glu Thr Asp Lys Asp Met Ser
         35                  40                  45
Ala Thr Val Ile Glu Gly Asn Asp Ala Val Thr Gly His Ile Ile Ser
         50                  55                  60
Thr Thr Ile Gly Gly Lys Asn Gly Glu Pro Lys Glu Thr Ile Ser Tyr
 65                  70                  75                  80
Met Ala Glu Arg Val Val Gly Thr Gly Ser Phe Gly Val Val Phe Gln
                 85                  90                  95
Ala Lys Cys Leu Glu Thr Gly Glu Ala Val Ala Ile Lys Lys Val Leu
                100                 105                 110
Gln Asp Arg Arg Tyr Lys Asn Arg Glu Leu Gln Leu Met Arg Leu Met
                115                 120                 125
Asp His Pro Asn Val Ile Ser Leu Lys His Cys Phe Phe Ser Thr Thr
            130                 135                 140
Ser Arg Asp Glu Leu Phe Leu Asn Leu Val Met Glu Tyr Val Pro Glu
145                 150                 155                 160
Ser Met Tyr Arg Val Ile Lys His Tyr Thr Thr Met Asn Gln Arg Met
                165                 170                 175
Pro Leu Ile Tyr Val Lys Leu Tyr Thr Tyr Gln Ile Phe Arg Gly Leu
                180                 185                 190
Ala Tyr Ile His Thr Ala Leu Gly Val Cys His Arg Asp Val Lys Pro
                195                 200                 205
Gln Asn Leu Leu Val His Pro Leu Thr His Gln Val Lys Leu Cys Asp
            210                 215                 220
Phe Gly Ser Ala Lys Val Leu Val Lys Gly Glu Ser Asn Ile Ser Tyr
225                 230                 235                 240
Ile Cys Ser Arg Tyr Tyr Arg Ala Pro Glu Leu Ile Phe Gly Ala Thr
                245                 250                 255
Glu Tyr Thr Ala Ser Ile Asp Ile Trp Ser Ala Gly Cys Val Leu Ala
                260                 265                 270
Glu Leu Leu Leu Gly Gln Pro Leu Phe Pro Gly Glu Asn Gln Val Asp
            275                 280                 285
Gln Leu Val Glu Ile Ile Lys Val Leu Gly Thr Pro Thr Arg Glu Glu
            290                 295                 300
Ile Arg Cys Met Asn Pro Asn Tyr Thr Glu Phe Arg Phe Pro Gln Ile
305                 310                 315                 320
Lys Ala His Pro Trp His Lys Val Phe His Lys Arg Met Pro Pro Glu
                325                 330                 335
Ala Ile Asp Leu Ala Ser Arg Leu Leu Gln Tyr Ser Pro Ser Leu Arg
            340                 345                 350
Cys Thr Ala Leu Glu Ala Cys Ala His Pro Phe Phe Asp Glu Leu Arg
            355                 360                 365
Glu Pro Asn Ala Arg Leu Pro Asn Gly Arg Pro Leu Pro Pro Leu Phe
        370                 375                 380
Asn Phe Lys Gln Glu Leu Ala Gly Ala Ser Pro Glu Leu Ile Asn Arg
385                 390                 395                 400
Leu Ile Pro Glu His Ile Arg Arg Gln Met Gly Leu Ser Phe Pro His
                405                 410                 415
Ser Ala Gly Thr
            420
```

-continued

```
<210> SEQ ID NO 27
<211> LENGTH: 2342
<212> TYPE: DNA
<213> ORGANISM: Glycine max

<400> SEQUENCE: 27
gagtttcaaa ggttgttggt gtgcatcacc acctgcattc tatgttggat gcccaatggt      60
gccactgccg ccacagatcc aaatgatgct gctgctgtga attttttgtt tcaaaatatg     120
aactcaccac cccagctagg ttggcctcct aatggtgatg atccatgtgg acaatcttgg     180
aaaggcatta cttgctctgg caatcgtgtt acagagatta agttatctaa tcttggacta     240
actggatcgt tgccttatgg attacaagtc ttgacatctt tgacctacgt agacatgagt     300
agcaacagtc ttggtggcag cataccgtac caacttcctc catatttgca gcacttaaat     360
cttgcttata caacatcac agggacagta ccttattcga tttctaactt gactgctctt     420
actgacctga atttagtca caatcagctc cagcaaggac tgggtgttga ctttcttaat     480
cttctactc tctccacatt ggatctctct ttcaatttc taacaggtga cctccctcag     540
actatgagct cactttcacg cataaccacc atgtatctgc aaaataacca gtttacaggc     600
actattgatg tccttgctaa tctgcctctg gataatctga atgtggaaaa taataatttt     660
actggatgga taccgaaaca gttgaagaac ataaacctac agaccggtgg taatgcatgg     720
agctcagggc ctgcaccccc acctcctcct gggacacctc cagcacctaa aagcaaccag     780
caccacaagt ctggtggtgg aagcaccacc ccctcagata ctgccactgg cagcagctca     840
attgacgagg gaaaaaaatc tggtacagga ggtggtgcca tagccggaat tgtgatctct     900
gtcatagttg tgggggcaat agtagcattc tttctggtga agagaaaatc caagaagtca     960
tcttctgatt tagaaaagca ggataatcag tcctttgctc cacttctttc aaatgaagtg    1020
catgaagaaa agtccatgca aacttcctct gtaacagact tgaagacgtt tgatacttct    1080
gcctcaataa atcttaaacc cccacctatt gaccgtcata aatcatttga tgatgaagaa    1140
ttctccaaga ggcccacaat tgtgaagaag actgtaacag ctcctgcaaa tgtgaaatca    1200
tattctattg ctgaactgca gattgctact ggcagcttca gtgtggatca ccttgttggc    1260
gagggatctt ttgggcgtgt ttaccgtgct caatttgatg atggacaggt tcttgcagtg    1320
aagaagatag attcatctat ccttcccaat gatttgacag atgatttat acaaataatt    1380
tcaaacatct ccaatttaca tcatccaaat gtgacagagc ttgtaggtta ttgctcagag    1440
tatggacaac acctcttggt ctatgagttt cataaaaatg gatcactgca tgacttcctt    1500
cacctatcag atgaatatag taaaccattg atatggaatt cccgtgtcaa gattgctttg    1560
gggactgcac gtgctctaga gtacctacat gaagttagtt cgccatcagt tgttcataag    1620
aatattaagt cagccaacat attacttgat acagaactta atcctcatct ttcagatagt    1680
ggattggcaa gttatattcc aaatgccgac cagatattga atcataatgt tggatctgga    1740
tatgatgcac ctgaagttgc cttgtctggt cagtatactt tgaaaagtga tgtctacagc    1800
tttggagtcg tcatgttgga acttctcagt ggacggaacc cttttgatag ctcaaggcca    1860
agatctgagc agtctttggt tcgatgggca acacctcaac tccatgatat tgatgcattg    1920
gctaaaatgg ttgatcctgc aatgaaaggg ttatatcctg ttaagtctct ttctcgattt    1980
gccgatgtta ttgctctttg cgttcagccg gagccagaat tccgaccacc gatgtcagaa    2040
gtggttcaag cactggtgcg actagtgcag cgagctaaca tgagcaagcg aacatttagt    2100
agtagtgatc atggaggatc ccaacgaggg agtgatgagc cagttctacg agacatctaa    2160
```

-continued

```
atcccaaagc aaatgtagtt atatttttct cccaagctag ttcggttatt tgtaatataa    2220
tttccaatag ttgcaaattt gaattgatgg gttccatatt ctgttgatac ctatgtaaac    2280
ctgtccaaat cagcttatta caatgacagt aacggttgca ctggcaaaaa aaaaaaaaa    2340 aa                                                                    2342
```

<210> SEQ ID NO 28
<211> LENGTH: 703
<212> TYPE: PRT
<213> ORGANISM: Glycine max

<400> SEQUENCE: 28

```
Met Pro Asn Gly Ala Thr Ala Ala Thr Asp Pro Asn Asp Ala Ala Ala
  1               5                  10                  15

Val Arg Phe Leu Phe Gln Asn Met Asn Ser Pro Gln Leu Gly Trp
                 20                  25                  30

Pro Pro Asn Gly Asp Asp Pro Cys Gly Gln Ser Trp Lys Gly Ile Thr
             35                  40                  45

Cys Ser Gly Asn Arg Val Thr Glu Ile Lys Leu Ser Asn Leu Gly Leu
         50                  55                  60

Thr Gly Ser Leu Pro Tyr Gly Leu Gln Val Leu Thr Ser Leu Thr Tyr
 65                  70                  75                  80

Val Asp Met Ser Ser Asn Ser Leu Gly Gly Ser Ile Pro Tyr Gln Leu
                 85                  90                  95

Pro Pro Tyr Leu Gln His Leu Asn Leu Ala Tyr Asn Asn Ile Thr Gly
            100                 105                 110

Thr Val Pro Tyr Ser Ile Ser Asn Leu Thr Ala Leu Thr Asp Leu Asn
        115                 120                 125

Phe Ser His Asn Gln Leu Gln Gln Gly Leu Gly Val Asp Phe Leu Asn
    130                 135                 140

Leu Ser Thr Leu Ser Thr Leu Asp Leu Ser Phe Asn Phe Leu Thr Gly
145                 150                 155                 160

Asp Leu Pro Gln Thr Met Ser Ser Leu Ser Arg Ile Thr Thr Met Tyr
                165                 170                 175

Leu Gln Asn Asn Gln Phe Thr Gly Thr Ile Asp Val Leu Ala Asn Leu
            180                 185                 190

Pro Leu Asp Asn Leu Asn Val Glu Asn Asn Asn Phe Thr Gly Trp Ile
        195                 200                 205

Pro Glu Gln Leu Lys Asn Ile Asn Leu Gln Thr Gly Gly Asn Ala Trp
    210                 215                 220

Ser Ser Gly Pro Ala Pro Pro Pro Pro Gly Thr Pro Ala Pro
225                 230                 235                 240

Lys Ser Asn Gln His His Lys Ser Gly Gly Ser Thr Thr Pro Ser
                245                 250                 255

Asp Thr Ala Thr Gly Ser Ser Ile Asp Glu Gly Lys Lys Ser Gly
            260                 265                 270

Thr Gly Gly Gly Ala Ile Ala Gly Ile Val Ile Ser Val Ile Val Val
        275                 280                 285

Gly Ala Ile Val Ala Phe Phe Leu Val Lys Arg Lys Ser Lys Lys Ser
    290                 295                 300

Ser Ser Asp Leu Glu Lys Gln Asp Asn Gln Ser Phe Ala Pro Leu Leu
305                 310                 315                 320

Ser Asn Glu Val His Glu Glu Lys Ser Met Gln Thr Ser Ser Val Thr
                325                 330                 335
```

-continued

```
Asp Leu Lys Thr Phe Asp Thr Ser Ala Ser Ile Asn Leu Lys Pro Pro
            340                 345                 350

Pro Ile Asp Arg His Lys Ser Phe Asp Asp Glu Glu Phe Ser Lys Arg
            355                 360             365

Pro Thr Ile Val Lys Lys Thr Val Thr Ala Pro Ala Asn Val Lys Ser
            370             375             380

Tyr Ser Ile Ala Glu Leu Gln Ile Ala Thr Gly Ser Phe Ser Val Asp
385                 390                 395                 400

His Leu Val Gly Glu Gly Ser Phe Gly Arg Val Tyr Arg Ala Gln Phe
                405                 410                 415

Asp Asp Gly Gln Val Leu Ala Val Lys Lys Ile Asp Ser Ser Ile Leu
            420                 425                 430

Pro Asn Asp Leu Thr Asp Phe Ile Gln Ile Ile Ser Asn Ile Ser
            435                 440                 445

Asn Leu His His Pro Asn Val Thr Glu Leu Val Gly Tyr Cys Ser Glu
450                 455                 460

Tyr Gly Gln His Leu Leu Val Tyr Glu Phe His Lys Asn Gly Ser Leu
465                 470                 475                 480

His Asp Phe Leu His Leu Ser Asp Glu Tyr Ser Lys Pro Leu Ile Trp
                485                 490                 495

Asn Ser Arg Val Lys Ile Ala Leu Gly Thr Ala Arg Ala Leu Glu Tyr
            500                 505                 510

Leu His Glu Val Ser Ser Pro Ser Val Val His Lys Asn Ile Lys Ser
            515                 520                 525

Ala Asn Ile Leu Leu Asp Thr Glu Leu Asn Pro His Leu Ser Asp Ser
530                 535                 540

Gly Leu Ala Ser Tyr Ile Pro Asn Ala Asp Gln Ile Leu Asn His Asn
545                 550                 555                 560

Val Gly Ser Gly Tyr Asp Ala Pro Glu Val Ala Leu Ser Gly Gln Tyr
                565                 570                 575

Thr Leu Lys Ser Asp Val Tyr Ser Phe Gly Val Val Met Leu Glu Leu
            580                 585                 590

Leu Ser Gly Arg Asn Pro Phe Asp Ser Ser Arg Pro Arg Ser Glu Gln
            595                 600                 605

Ser Leu Val Arg Trp Ala Thr Pro Gln Leu His Asp Ile Asp Ala Leu
            610                 615                 620

Ala Lys Met Val Asp Pro Ala Met Lys Gly Leu Tyr Pro Val Lys Ser
625                 630                 635                 640

Leu Ser Arg Phe Ala Asp Val Ile Ala Leu Cys Val Gln Pro Glu Pro
                645                 650                 655

Glu Phe Arg Pro Pro Met Ser Glu Val Val Gln Ala Leu Val Arg Leu
            660                 665                 670

Val Gln Arg Ala Asn Met Ser Lys Arg Thr Phe Ser Ser Ser Asp His
            675                 680                 685

Gly Gly Ser Gln Arg Gly Ser Asp Glu Pro Val Leu Arg Asp Ile
690                 695                 700
```

<210> SEQ ID NO 29
<211> LENGTH: 1610
<212> TYPE: DNA
<213> ORGANISM: Oryza sativa

<400> SEQUENCE: 29
accacacaaa aaagcaaaac agagagaaca actgttactc acacacgcca tgggtaaatg    60

-continued

```
aatggttttt gagcaacagc agttaaaaga gaaaagggat tcagcgaaga tgacatcggt      120
tggtgtggca ccaacttcgg gtttgagaga agccagtggg catggagcag cagctgcgga      180
tagattgcca gaggagatga acgatatgaa aattagggat gatagagaaa tggaagccac      240
agttgttgat ggcaacggaa cggagacagg acatatcatt gtgactacca ttgggggtag      300
aaatggtcag cccaagcaga ctataagcta catggcagag cgtgttgtag ggcatggatc      360
atttggagtt gtcttccagg ctaagtgctt ggaaaccggt gaaactgtgg ctatcaaaaa      420
ggttcttcaa gataagaggt acaagaaccg ggagctgcaa acaatgcgcc ttcttgacca      480
cccaaatgtt gtcgctttga agcactgttt cttttcaacc actgaaaagg atgaactata      540
cctcaatttg gtacttgaat atgttcctga acagttaat cgtgtgatca acattacaa        600
caagttaaac caaggatgc cgctgatata tgtgaaactc tatacatacc agatctttag       660
ggcgttatct tatattcatc gttgtattgg agtctgccat cgggatatca agcctcaaaa      720
tctattggtc aatccacaca ctcaccaggt taaattatgt gactttggaa gtgcaaaggt      780
tttggtaaaa ggcgaaccaa atatatcata catatgttct agatactata gagcacctga      840
gctcatattt ggcgcaactg aatatacttc agccattgac atctggtctg ttggatgtgt      900
tttagctgag ctgctgcttg acagcctct gttccctggt gagagtggag ttgatcaact       960
tgttgagatc atcaaggttc tgggcactcc aacaagggaa gagattaagt gcatgaaccc     1020
taattataca gaatttaaat tcccacagat taaagcacat ccatggcaca agatcttcca     1080
taagcgcatg cctccagagg ctgttgattt ggtatcaaga ctactacaat actcccctaa     1140
cttgcggtgc acagcttttg atgccttgac gcatcctttc ttcgacgagc ttcgtgatcc     1200
aaatactcgc ttgccaaatg ccgattcct tccaccacta tttaatttca atcccatga       1260
actgaaagga gtcccatctg agattttggt gaaattggtt ccagagcatg caaggaagca     1320
atgcccgttt ctaggctcgt gaagtgttgt ttccatatga gaatgctgcg cttccttttt     1380
ctatttaata tgatattttt gttggtatct ttattgtatt cggttgccct gtaaaagcag     1440
atttagagat acatgctact cattatcacc caaccccga tggttatgta gaataccctg       1500
tttcctgtat cacagcagat tgtaacatac aatagaggac aaaatgtctg caattatcta     1560
aatgttgcat caatatttgt atttgttgag gcaaaaaaaa aaaaaaaaa                  1610
```

<210> SEQ ID NO 30
<211> LENGTH: 426
<212> TYPE: PRT
<213> ORGANISM: Oryza sativa

<400> SEQUENCE: 30

```
Met Val Phe Glu Gln Gln Gln Leu Lys Glu Lys Arg Asp Ser Ala Lys
1               5                  10                  15

Met Thr Ser Val Gly Val Ala Pro Thr Ser Gly Leu Arg Glu Ala Ser
            20                  25                  30

Gly His Gly Ala Ala Ala Ala Asp Arg Leu Pro Glu Glu Met Asn Asp
        35                  40                  45

Met Lys Ile Arg Asp Asp Arg Glu Met Glu Ala Thr Val Val Asp Gly
    50                  55                  60

Asn Gly Thr Glu Thr Gly His Ile Ile Val Thr Thr Ile Gly Gly Arg
65                  70                  75                  80

Asn Gly Gln Pro Lys Gln Thr Ile Ser Tyr Met Ala Glu Arg Val Val
                85                  90                  95
```

Gly His Gly Ser Phe Gly Val Phe Gln Ala Lys Cys Leu Glu Thr
            100                 105                 110

Gly Glu Thr Val Ala Ile Lys Lys Val Leu Gln Asp Lys Arg Tyr Lys
        115                 120                 125

Asn Arg Glu Leu Gln Thr Met Arg Leu Leu Asp His Pro Asn Val Val
    130                 135                 140

Ala Leu Lys His Cys Phe Phe Ser Thr Thr Glu Lys Asp Glu Leu Tyr
145                 150                 155                 160

Leu Asn Leu Val Leu Glu Tyr Val Pro Glu Thr Val Asn Arg Val Ile
                165                 170                 175

Lys His Tyr Asn Lys Leu Asn Gln Arg Met Pro Leu Ile Tyr Val Lys
            180                 185                 190

Leu Tyr Thr Tyr Gln Ile Phe Arg Ala Leu Ser Tyr Ile His Arg Cys
        195                 200                 205

Ile Gly Val Cys His Arg Asp Ile Lys Pro Gln Asn Leu Leu Val Asn
    210                 215                 220

Pro His Thr His Gln Val Lys Leu Cys Asp Phe Gly Ser Ala Lys Val
225                 230                 235                 240

Leu Val Lys Gly Glu Pro Asn Ile Ser Tyr Ile Cys Ser Arg Tyr Tyr
                245                 250                 255

Arg Ala Pro Glu Leu Ile Phe Gly Ala Thr Glu Tyr Thr Ser Ala Ile
            260                 265                 270

Asp Ile Trp Ser Val Gly Cys Val Leu Ala Glu Leu Leu Gly Gln
        275                 280                 285

Pro Leu Phe Pro Gly Glu Ser Gly Val Asp Gln Leu Val Glu Ile Ile
    290                 295                 300

Lys Val Leu Gly Thr Pro Thr Arg Glu Glu Ile Lys Cys Met Asn Pro
305                 310                 315                 320

Asn Tyr Thr Glu Phe Lys Phe Pro Gln Ile Lys Ala His Pro Trp His
                325                 330                 335

Lys Ile Phe His Lys Arg Met Pro Pro Glu Ala Val Asp Leu Val Ser
            340                 345                 350

Arg Leu Leu Gln Tyr Ser Pro Asn Leu Arg Cys Thr Ala Phe Asp Ala
        355                 360                 365

Leu Thr His Pro Phe Phe Asp Glu Leu Arg Asp Pro Asn Thr Arg Leu
    370                 375                 380

Pro Asn Gly Arg Phe Leu Pro Pro Leu Phe Asn Phe Lys Ser His Glu
385                 390                 395                 400

Leu Lys Gly Val Pro Ser Glu Ile Leu Val Lys Leu Val Pro Glu His
                405                 410                 415

Ala Arg Lys Gln Cys Pro Phe Leu Gly Ser
            420                 425

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 31
caggaaacag ctatgacc                                              18

<210> SEQ ID NO 32
<211> LENGTH: 19
<212> TYPE: DNA

```
<213> ORGANISM: Artificial Sequence
<220> FEATURE:
<223> OTHER INFORMATION: Description of Artificial Sequence: Primer

<400> SEQUENCE: 32
ctaaagggaa caaaagctg                                                     19

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 33
tgtaaaacga cggccagt                                                      18

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 34
atcccgggcg agtcttctat ggcatctgcg act                                     33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 35
atgagctcaa tatcaggagt tgcacccttc aac                                     33

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 36
tgtgtctacg tgtcgcgggg tcgat                                              25

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 37
atcccgggag gcattgaact acctggagtg ag                                      32

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 38
gcgatatcgt tgaactagta atctgtgtta actt                                    34
```

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 39
ctgcgacgga aaactctctt gctgt                                           25

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 40
gcgagctcgt gcgaatcatg tactcccatc acac                                 34

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 41
gcaacgactt gccagaacct cgtgc                                           25

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 42
cggagctcga tgcagcggta tatccttgct cct                                  33

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 43
gcgatatcgt tgaactagta atctgtgtta actttatc                             38

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 44
gcagcggtat atccttgctc ctcatc                                          26

<210> SEQ ID NO 45
<211> LENGTH: 26
<212> TYPE: DNA
<213> ORGANISM: Artificial Sequence
<220> FEATURE:

-continued

<223> OTHER INFORMATION: Description of Artificial Sequence: Primer

<400> SEQUENCE: 45
cgatgtgaga cgcccttgct gtggca 26

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 46
atcccgggtg tcggaattcg gtcacaatga gct 33

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 47
atcccgggtt tctggaatag ctcagaagcg t 31

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 48
gcgctgcaga tttcatttgg agaggacacg 30

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 49
cgcggccggc ctcagaagaa ctcgtcaaga aggcg 35

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 50
cgagagctgc agatcatgcg actgttg 27

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 51
gctctgccat cacgcaaccc atcgac 26

PROTEIN KINASE STRESS-RELATED POLYPEPTIDES AND METHODS OF USE IN PLANTS

CROSS-REFERENCE TO RELATED APPLICATIONS

The present invention claims the priority benefit of U.S. Provisional Patent Application Ser. No. 60/346,096 filed Nov. 9, 2001, the entire contents of which are hereby incorporated by reference.

BACKGROUND OF THE INVENTION

1. Field of the Invention

This invention relates generally to nucleic acid sequences encoding polypeptides that are associated with abiotic stress responses and abiotic stress tolerance in plants. In particular, this invention relates to nucleic acid sequences encoding polypeptides that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Drought and cold stresses, as well as salt stresses, have a common theme important for plant growth, and that is water availability. Plants are exposed during their entire life cycle to conditions of reduced environmental water content, and most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Because high salt content in some soils results in less water being available for cell intake, high salt concentration has an effect on plants similar to the effect of drought on plants. Additionally, under freezing temperatures, plant cells lose water as a result of ice formation that starts in the apoplast and withdraws water from the symplast. A plant's molecular response mechanisms to each of these stress conditions are common, and protein kinases play an essential role in these molecular mechanisms.

Protein kinases represent a superfamily, and the members of this superfamily catalyze the reversible transfer of a phosphate group of ATP to serine, threonine, and tyrosine amino acid side chains on target polypeptides. Protein kinases are primary elements in signaling processes in plants and have been reported to play crucial roles in perception and transduction of signals that allow a cell (and the plant) to respond to environmental stimuli. In particular, receptor protein kinases (RPKs) represent one group of protein kinases that activate a complex array of intracellular signaling pathways in response to the extracellular environment (Van der Gear et al., 1994, Annu. Rev. Cell Biol. 10:251–337). RPKs are single-pass transmembrane polypeptides that contain an amino-terminal signal sequence, extracellular domains unique to each receptor, and a cytoplasmic kinase domain. Ligand binding induces homo- or hetero-dimerization of RPKs, and the resultant close proximity of the cytoplasmic domains results in kinase activation by transphosphorylation. Although plants have many polypeptides similar to RPKs, no ligand has been identified for these receptor-like kinases (RLKs). The majority of plant RLKs that have been identified belong to the family of Serine/Threonine (Ser/Thr) kinases, and most have extracellular Leucine-rich repeats (Becraft, P W., 1998, Trends Plant Sci. 3:384–388).

Another type of protein kinase is the Ca+-dependent protein kinase (CDPK). This type of kinase has a calmodulin-like domain at the COOH terminus which allows response to Ca+ signals directly without calmodulin being present. Currently, CDPKs are the most prevalent Ser/Thr polypeptide kinases found in higher plants. Although their physiological roles remain unclear, they are induced by cold, drought, and abscisic acid (ABA) (Knight et al., 1991, Nature 352:524; Schroeder, J. I. and Thuleau, P., 1991, Plant Cell 3:555; Bush, D. S., 1995, Annu. Rev. Plant Phys. Plant Mol. Biol. 46:95; Urao, T. et al., 1994, Mol. Gen. Genet. 244:331).

Another type of signaling mechanism involves members of the conserved SNF1 Serine/Threonine polypeptide kinase family. These kinases play essential roles in eukaryotic glucose and stress signaling. Plant SNF1-like kinases participate in the control of key metabolic enzymes, including HMGR, nitrate reductase, sucrose synthase, and sucrose phosphate synthase (SPS). Genetic and biochemical data indicate that sugar-dependent regulation of SNF1 kinases involves several other sensory and signaling components in yeast, plants, and animals.

Additionally, members of the Mitogen-Activated Protein Kinase (MAPK) family have been implicated in the actions of numerous environmental stresses in animals, yeasts and plants. It has been demonstrated that both MAPK-like kinase activity and mRNA levels of the components of MAPK cascades increase in response to environmental stress and plant hormone signal transduction. MAP kinases are components of sequential kinase cascades, which are activated by phosphorylation of threonine and tyrosine residues by intermediate upstream MAP kinase kinases (MAP-KKs). The MAPKKs are themselves activated by phosphorylation of serine and threonine residues by upstream kinases (MAPKKKs). A number of MAP Kinase genes have been reported in higher plants.

Another major type of environmental stress is lodging, which refers to the bending of shoots or stems in response to wind, rain, pests or disease. Two types of lodging occur in cereals: root-lodging and stem breakage. The most common type of lodging is root lodging, which occurs early in the season. Stem-breakage, by comparison, occurs later in the season as the stalk becomes more brittle due to crop maturation. Stem breakage has greater adverse consequences on crop yield, since the plants cannot recover as well as from the earlier root-lodging.

Lodging in cereal crops is influenced by morphological (structural) plant traits as well as environmental conditions. Lodging in cereals is often a result of the combined effects of inadequate standing power of the crop and adverse weather conditions, such as rain, wind, and/or hail. Lodging is also variety (cultivar) dependent. For example, a tall, weak-stemmed wheat cultivar has a greater tendency to lodge than a semi-dwarf cultivar with stiffer straw. In addition, the tendency of a crop to lodge depends on the resistance especially of the lower internodes. This is because the lower internodes have to resist the greatest movement of force. The weight of the higher internodes of the stems plus leaves and heads in relation to the stem (culm) will affect the resistance of a crop to lodging. The heavier the higher parts of the stem are and the greater the distance from their center of gravity to the base of the stem, the greater is the movement of the forces acting upon the lower internodes and the roots. Supporting this argument, it was found that the breaking strength of the lowest internode and shoot per root ratio were the most suitable indices of lodging. Furthermore, plant morphological (structural) characteristics such as plant height, wall thickness, and cell wall lignification can affect the ability of the plant to resist a lateral force.

Severe lodging is very costly due to its effects on grain formation and associated harvesting problems and losses. It takes about twice the time to harvest a lodged crop than a standing one. Secondary growth in combination with a flattened crop makes harvesting difficult and can subsequently lead to poor grain quality. Yield loss comes from poor grain filling, head loss, and bird damage. Yield losses are most severe when a crop lodges during the ten days following head emergence. Yield losses at this stage will range between 15% and 40%. Lodging that occurs after the plant matures will not affect the yield but it may reduce the amount of harvestable grain. For instance, when lodging occurs after the plant matures, neck breakage and the loss of the whole head can result; these often lead to severe harvest losses. In theses cases, farmers who straight combine their grain will likely incur higher losses than those who swath them. Accordingly, it is desirable to identify genes expressed in lodging resistant plants that have the capacity to confer lodging resistance to the host plant and to other plant species.

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress tolerance to its host plant and to other plant species. Newly generated stress tolerant plants will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

This invention fulfills in part the need to identify new, unique protein kinases capable of conferring stress tolerance to plants upon over-expression. The present invention describes a novel genus of Protein Kinase Stress-Related Polypeptides (PKSRPs) and PKSRP coding nucleic acids that are important for modulating a plant's response to an environmental stress. More particularly, over-expression of these PKSRP coding nucleic acids in a plant results in the plant's increased tolerance to an environmental stress.

The present invention includes an isolated plant cell comprising a PKSRP coding nucleic acid, wherein expression of the nucleic acid sequence in the plant cell results in increased tolerance to environmental stress as compared to a wild type variety of the plant cell. Namely, described herein are PK-3, PK-4, PK-10, and PK-11 from *Physcomitrella patens;* BnPK-1, BnPK-2, BnPK-3, and BnPK-4 from *Brassica napus;* GmPK-1, GmPK-2, GmPK-3, and GmPK-4, from *Glycine max;* and OsPK-1 from *Oryza sativa*.

The invention provides in some embodiments that the PKSRP and coding nucleic acid are those that are found in members of the genus *Physcomitrella Brassica, Glycine*, or *Oryza*. In another preferred embodiment, the nucleic acid and polypeptide are from a *Physcomitrella patens* plant, a *Brassica napus* plant, a *Glycine max* plant, or an *Oryza sativa* plant. The invention provides that the environmental stress can be increased salinity, drought, temperature, metal, chemical, pathogenic, and oxidative stresses, or combinations thereof. In preferred embodiments, the environmental stress can be drought or cold temperature.

The invention further provides a seed produced by a transgenic plant transformed by a PKSRP coding nucleic acid, wherein the plant is true breeding for increased tolerance to environmental stress as compared to a wild type variety of the plant. The invention further provides a seed produced by a transgenic plant expressing a PKSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated PKSRP as described below. The invention further provides an isolated PKSRP coding nucleic acid, wherein the PKSRP coding nucleic acid codes for a PKSRP as described below.

The invention further provides an isolated recombinant expression vector comprising a PKSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a PKSRP coding nucleic acid, wherein expression of the nucleic acid in the plant results in increased tolerance to environmental stress as compared to a wild type variety of the plant comprising: (a) transforming a plant cell with an expression vector comprising a PKSRP coding nucleic acid, and (b) generating from the plant cell a transgenic plant with an increased tolerance to environmental stress as compared to a wild type variety of the plant. In preferred embodiments, the PKSRP and PKSRP coding nucleic acid are as described below.

The present invention further provides a method of identifying a novel PKSRP, comprising (a) raising a specific antibody response to a PKSRP, or fragment thereof, as described below; (b) screening putative PKSRP material with the antibody, wherein specific binding of the antibody to the material indicates the presence of a potentially novel PKSRP; and (c) identifying from the bound material a novel PKSRP in comparison to known PKSRP. Alternatively, hybridization with nucleic acid probes as described below can be used to identify novel PKSRP nucleic acids.

The present invention also provides methods of modifying stress tolerance of a plant comprising, modifying the expression of a PKSRP nucleic acid in the plant, wherein the PKSRP is as described below. The invention provides that this method can be performed such that the stress tolerance is either increased or decreased. Preferably, stress tolerance is increased in a plant via increasing expression of a PKSRP nucleic acid.

In another aspect, the invention provides methods of increasing a plant's resistance to lodging comprising, transforming a plant cell with an expression cassette comprising a PKSRP nucleic acid and generating a plant from the plant cell.

DETAILED DESCRIPTION OF THE INVENTION

Figure 1:
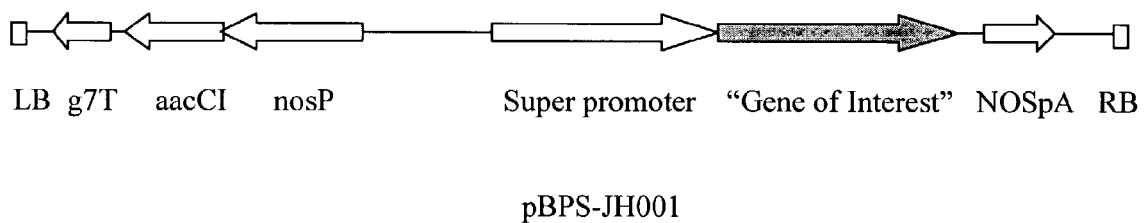
FIG. 1 shows a diagram of the plant expression vector pBPS-JH001 containing the super promoter driving the expression of the PKSRP coding nucleic acid ("Gene of Interest"). The components are: aacCI gentamycin resistance gene (Hajdukiewicz et al., 1994, Plant Molec. Biol. 25: 989–94), NOS promoter (Becker et al., 1992, Plant Molec. Biol. 20: 1195–97), g7T terminator (Becker et al., 1992), and NOSpA terminator (Jefferson et al., 1987, EMBO J. 6:3901–7).
Figure 2:
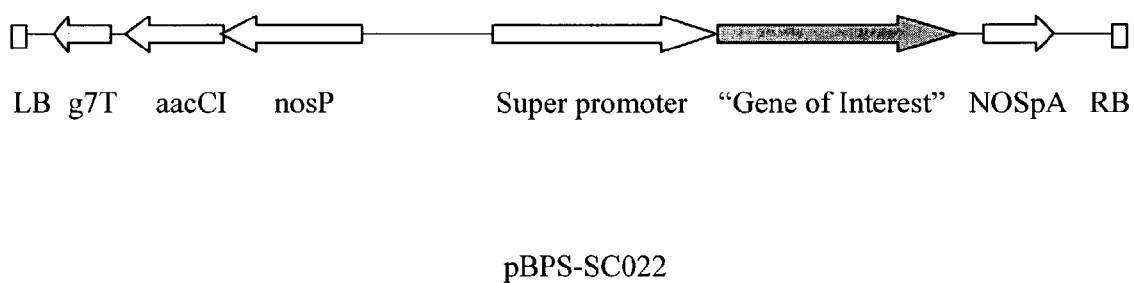
FIG. 2 shows a diagram of the plant expression vector pBPS-SC022 containing the super promoter driving the expression of the PKSRP coding nucleic acid (Gene of Interest"). The components are: NPTII kanamycin resistance gene (Hajdukiewicz et al., 1994, Plant Molec. Biol. 25: 989–98), AtAct2-1 promoter (An et al., 1996, Plant J. 10: 107–21), and OCS3 terminator (Weigel et al., 2000, Plant Physiol 122:1003–13).

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Protein Kinase Stress-Related Polypeptides" (PKSRPs), in no way limits the functionality of those sequences.

The present invention describes a novel genus of Protein Kinase Stress-Related Polypeptides (PKSRPs) and PKSRP coding nucleic acids that are important for modulating a plant's response to an environmental stress. More particularly, over-expression of these PKSRP coding nucleic acids in a plant results in the plant's increased tolerance to an environmental stress.

The present invention provides a transgenic plant cell transformed by a PKSRP coding nucleic acid, wherein expression of the nucleic acid sequence in the plant cell results in increased tolerance to environmental stress or increased resistance to lodging as compared to a wild type variety of the plant cell. The invention further provides transgenic plant parts and transgenic plants containing the plant cells described herein. In preferred embodiments, the transgenic plants and plant parts have increased tolerance to environmental stress or increased resistance to lodging as compared to a wild type variety of the plant. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by a PKSRP coding nucleic acid, wherein the seed contains the PKSRP coding nucleic acid, and wherein the plant is true breeding for increased tolerance to environmental stress as compared to a wild type variety of the plant. The invention further provides a seed produced by a transgenic plant expressing a PKSRP, wherein the seed contains the PKSRP, and wherein the plant is true breeding for increased tolerance to environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* PKSRPs, PK-3, PK-4, PK-10, and PK-11; the *Brassica napus* PKSRPs, BnPK-1, BnPK-2, BnPK-3, and BnPK-4; the *Glycine max* PKSRPs, GmPK-1, GmPK-2, GmPK-3, and GmPK-4; and the *Oryza sativa* PKSRP OsPK-1 are useful for increasing a plant's tolerance to environmental stress. As used herein, the term polypeptide refers to a chain of at least four amino acids joined by peptide bonds. The chain may be linear, branched, circular or combinations thereof. Accordingly, the present invention provides isolated PKSRPs selected from the group consisting of PK-3, PK-4, PK-10, PK-11, BnPK-1, BnPK-2, BnPK-3, BnPK-4, GmPK-1, GmPK-2, GmPK-3, GmPK-4, and OsPK-1, and homologs thereof. In preferred embodiments, the PKSRP is selected from: 1) *Physcomitrella patens* Protein Kinase-3 (PK-3) polypeptide as defined in SEQ ID NO:3; 2) *Physcomitrella patens* Protein Kinase-4 (PK-4) polypeptide as defined in SEQ ID NO:6; 3) *Physcomitrella patens* Protein Kinase-10 (PK-10) polypeptide as defined in SEQ ID NO:9; 4) *Physcomitrella patens* Protein Kinase-11 (PK-11) polypeptide as defined in SEQ ID NO:12; 5) *Brassica napus* Protein Kinase-1 (BnPK-1) polypeptide as defined in SEQ ID NO:14; 6) *Brassica napus* Protein Kinase-2 (BnPK-2) polypeptide as defined in SEQ ID NO:16; 7) *Brassica napus* Protein Kinase-3 (BnPK-3) polypeptide as defined in SEQ ID NO:18; 8) *Brassica napus* Protein Kinase-4 (BnPK-4) polypeptide as defined in SEQ ID NO:20; 9) *Glycine max* Protein Kinase-1 (GmPK-1) polypeptide as defined in SEQ ID NO:22; 10) *Glycine max* Protein Kinase-2 (GmPK-2) polypeptide as defined in SEQ ID NO:24; 11) *Glycine max* Protein Kinase-3 (GmPK-3) polypeptide as defined in SEQ ID NO:26; 12) *Glycine max* Protein Kinase-4 (GmPK-4) polypeptide as defined in SEQ ID NO:28; 13) *Oryza sativa* Protein Kinase-1 (OsPK-1) polypeptide as defined in SEQ ID NO:30; and homologs and orthologs thereof. Homologs and orthologs of the amino acid sequences are defined below.

The PKSRPs of the present invention are preferably produced by recombinant DNA techniques. For example, a nucleic acid molecule encoding the polypeptide is cloned into an expression vector (as described below), the expression vector is introduced into a host cell (as described below) and the PKSRP is expressed in the host cell. The PKSRP can then be isolated from the cells by an appropriate purification scheme using standard polypeptide purification techniques. For the purposes of the invention, the term "recombinant polynucleotide" refers to a polynucleotide that has been altered, rearranged or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, a PKSRP, or peptide can be synthesized chemically using standard peptide synthesis techniques. Moreover, native PKSRP can be isolated from cells (e.g., *Physcomitrella patens, Brassica napus, Glycine max,* or *Oryza sativa*), for example using an anti-PKSRP antibody, which can be produced by standard techniques utilizing a PKSRP or fragment thereof.

The invention further provides an isolated PKSRP coding nucleic acid. The present invention includes PKSRP coding nucleic acids that encode PKSRPs as described herein. In preferred embodiments, the PKSRP coding nucleic acid is selected from: 1) *Physcomitrella patens* Protein Kinase-3 (PK-3) nucleic acid as defined in SEQ ID NO:2; 2) *Physcomitrella patens* Protein Kinase-4 (PK-4) nucleic acid as defined in SEQ ID NO:5; 3) *Physcomitrella patens* Protein Kinase-10 (PK-10) nucleic acid as defined in SEQ ID NO:8; 4) *Physcomitrella patens* Protein Kinase-11 (PK-11) nucleic acid as defined in SEQ ID NO:11; 5) *Brassica napus* Protein Kinase-1 (BnPK-1) nucleic acid as defined in SEQ ID NO:13; 6) *Brassica napus* Protein Kinase-2 (BnPK-2) nucleic acid as defined in SEQ ID NO:15; 7) *Brassica napus* Protein Kinase-3 (BnPK-3) nucleic acid as defined in SEQ ID NO:17; 8) *Brassica napus* Protein Kinase-4 (BnPK-4) nucleic acid as defined in SEQ ID NO:19; 9) *Glycine max* Protein Kinase-1 (GmPK-1) nucleic acid as defined in SEQ ID NO:21; 10) *Glycine max* Protein Kinase-2 (GmPK-2) nucleic acid as defined in SEQ ID NO:23; 11) *Glycine max* Protein Kinase-3 (GmPK-3) nucleic acid as defined in SEQ ID NO:25; 12) *Glycine max* Protein Kinase-4 (GmPK-4) nucleic acid as defined in SEQ ID NO:27; 13) *Oryza sativa* Protein Kinase-1 (OsPK-1) nucleic acid as defined in SEQ ID NO:29; and homologs and orthologs thereof. Homologs and orthologs of the nucleotide sequences are defined below. In one preferred embodiment, the nucleic acid and polypeptide are isolated from the plant genus *Physcomitrella, Brassica, Glycine,* or *Oryza*. In another preferred embodiment, the nucleic acid and polypeptide are from a *Physcomitrella patens* (*P. patens*) plant, a *Brassica napus* plant, a *Glycine max* plant, or an *Oryza sativa* plant.

As used herein, the term "environmental stress" refers to any sub-optimal growing condition and includes, but is not limited to, sub-optimal conditions associated with salinity, drought, temperature, metal, chemical, pathogenic, and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. Also included within the definition of "environmental stress" is lodging, or the bending of shoots or stems in response to elements such as wind, rain, pests, or disease. Accordingly, the present invention provides compositions and methods of increasing lodging resistance in a plant. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. In various embodiments, the isolated PKSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens*, a *Brassica napus*, a *Glycine max*, or an *Oryza sativa* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or a portion thereof, can be isolated using standard molecular biology techniques and the sequence information provided herein. For example, a *P. patens* PKSRP cDNA can be isolated from a *P. patens* library using all or portion of one of the sequences of SEQ ID NO:1 and SEQ ID NO:4. Moreover, a nucleic acid molecule encompassing all or a portion of one of the sequences of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, and SEQ ID NO:29 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, and SEQ ID NO:29. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PKSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:1, SEQ ID NO:2, SEQ ID NO:4, SEQ ID NO:5, SEQ ID NO:7, SEQ ID NO:8, SEQ ID NO:10, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, and SEQ ID NO:29. These cDNAs may comprise sequences encoding the PKSRPs, (i.e., the "coding regions" of PK-3 and PK-4), as well as 5' untranslated sequences and 3' untranslated sequences. The coding region of PK-3 comprises nucleotides 138–1409 of SEQ ID NO:2 whereas the coding region of PK-4 comprises nucleotides 142–1395 of SEQ ID NO:5. It is to be understood that SEQ ID NO:2 and SEQ ID NO:5 comprise both coding regions and 5' and 3' untranslated regions. Alternatively, the nucleic acid molecules of the present invention can comprise only the coding region of any of the sequences in SEQ ID NO:2 and SEQ ID NO:5 or can contain whole genomic fragments isolated from genomic DNA. The present invention also includes PKSRP coding nucleic acids that encode PKSRPs as described herein. Preferred is a PKSRP coding nucleic acid that encodes a PKSRP selected from the group consisting of PK-3 as defined in SEQ ID NO:3, PK-4 as defined in SEQ ID NO:6, PK-10 as defined in SEQ ID NO:9, PK-11 as defined in SEQ ID NO:12, BnPK-1 as defined in SEQ ID NO:14, BnPK-2 as defined in SEQ ID NO:16, BnPK-3 as defined in SEQ ID NO:18, BnPK-4 as defined in SEQ ID NO:20, GmPK-1 as defined in SEQ ID NO:22, GmPK-2 as defined in SEQ ID NO:24, GmPK-3 as defined in SEQ ID NO:26, GmPK-4 as defined in SEQ ID NO:28, and OsPK-1 as defined in SEQ ID NO:30.

Moreover, the nucleic acid molecule of the invention can comprise a portion of the coding region of one of the sequences in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29, for example, a fragment which can be used as a probe or primer or a fragment encoding a biologically active portion of a PKSRP. The nucleotide sequences determined from the cloning of the PKSRP genes from *Physcomitrella patens, Brassica napus, Glycine max,* and *Oryza sativa* allow for the generation of probes and primers designed for use in identifying and/or cloning PKSRP homologs in other cell types and organisms, as well as PKSRP homologs from other related species. The portion of the coding region can also encode a biologically active fragment of a PKSRP.

As used herein, the term "biologically active portion of" a PKSRP is intended to include a portion, e.g., a domain/motif, of a PKSRP that participates in modulation of stress tolerance in a plant, and more preferably, drought tolerance or salt tolerance. For the purposes of the present invention, modulation of stress tolerance refers to at least a 10% increase or decrease in the stress tolerance of a transgenic plant comprising a PKSRP expression cassette (or expression vector) as compared to the stress tolerance of a non-transgenic control plant. Methods for quantitating stress tolerance are provided at least in Example 7 below. In a preferred embodiment, the biologically active portion of a PKSRP increases a plant's tolerance to an environmental stress.

Biologically active portions of a PKSRP include peptides comprising amino acid sequences derived from the amino acid sequence of a PKSRP, e.g., an amino acid sequence of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30 or the amino acid sequence of a polypeptide identical to a PKSRP, which include fewer amino acids than a full length PKSRP or the full length polypeptide which is identical to a PKSRP, and exhibit at least one activity of a PKSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PKSRP. Moreover, other biologically active portions in which other regions of the polypeptide are deleted, can be prepared by recombinant techniques and evaluated for one or more of the activities described herein. Preferably, the biologically active portions of a PKSRP include one or more selected domains/motifs or portions thereof having biological activity such as a kinase domain. For example, the kinase domain of PK-3 spans amino acid residues 87–360 of SEQ ID NO:3, and the kinase domain of PK-4 spans amino acid residues 81–281 of SEQ ID NO:6. Accordingly, the present invention includes PKSRPs comprising amino acid residues 87–360 of SEQ ID NO:3 and amino acid residues 81–281 of SEQ ID NO:6.

The invention also provides PKSRP chimeric or fusion polypeptides. As used herein, a PKSRP "chimeric polypeptide" or "fusion polypeptide" comprises a PKSRP operatively linked to a non-PKSRP. A PKSRP refers to a polypeptide having an amino acid sequence corresponding to a PKSRP, whereas a non-PKSRP refers to a polypeptide having an amino acid sequence corresponding to a polypeptide which is not substantially identical to the PKSRP, e.g., a polypeptide that is different from the PKSRP and is derived from the same or a different organism. As used herein with respect to the fusion polypeptide, the term "operatively linked" is intended to indicate that the PKSRP and the non-PKSRP are fused to each other so that both sequences fulfill the proposed function attributed to the sequence used. The non-PKSRP can be fused to the N-terminus or C-terminus of the PKSRP. For example, in one embodiment, the fusion polypeptide is a GST-PKSRP fusion polypeptide in which the PKSRP sequences are fused to the C-terminus of the GST sequences. Such fusion polypeptides can facilitate the purification of recombinant PKSRPs. In another embodiment, the fusion polypeptide is a PKSRP containing a heterologous signal sequence at its N-terminus. In certain host cells (e.g., mammalian host cells), expression and/or secretion of a PKSRP can be increased through use of a heterologous signal sequence.

Preferably, a PKSRP chimeric or fusion polypeptide of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (See, e.g., Current Protocols in Molecular Biology, eds. Ausubel et al. John Wiley & Sons: 1992). Moreover, many expression vectors are commercially available that already encode a fusion moiety (e.g., a GST polypeptide). A PKSRP encoding nucleic acid can be cloned into such an expression vector such that the fusion moiety is linked in-frame to the PKSRP.

In addition to fragments and fusion polypeptides of the PKSRPs described herein, the present invention includes homologs and analogs of naturally occurring PKSRPs and PKSRP encoding nucleic acids in a plant. "Homologs" are defined herein as two nucleic acids or polypeptides that have similar, or substantially identical, nucleotide or amino acid sequences, respectively. Homologs include allelic variants, orthologs, paralogs, agonists and antagonists of PKSRPs as defined hereafter. The term "homolog" further encompasses nucleic acid molecules that differ from one of the nucleotide sequences shown in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29 (and portions thereof) due to degeneracy of the genetic code and thus encode the same PKSRP as that encoded by the nucleotide sequences shown in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29. As used herein a "naturally occurring" PKSRP refers to a PKSRP amino acid sequence that occurs in nature. Preferably, a naturally occurring PKSRP comprises an amino acid sequence selected from the group consisting of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30.

An agonist of the PKSRP can retain substantially the same, or a subset, of the biological activities of the PKSRP. An antagonist of the PKSRP can inhibit one or more of the activities of the naturally occurring form of the PKSRP. For example, the PKSRP antagonist can competitively bind to a downstream or upstream member of the cell membrane component metabolic cascade that includes the PKSRP, or bind to a PKSRP that mediates transport of compounds across such membranes, thereby preventing translocation from taking place.

Nucleic acid molecules corresponding to natural allelic variants and analogs, orthologs and paralogs of a PKSRP cDNA can be isolated based on their identity to the *Physcomitrella patens, Brassica napus, Glycine max*, or *Oryza sativa* PKSRP nucleic acids described herein using PKSRP cDNAs, or a portion thereof, as a hybridization probe according to standard hybridization techniques under stringent hybridization conditions. In an alternative embodiment, homologs of the PKSRP can be identified by screening combinatorial libraries of mutants, e.g., truncation mutants, of the PKSRP for PKSRP agonist or antagonist activity. In one embodiment, a variegated library of PKSRP variants is generated by combinatorial mutagenesis at the nucleic acid level and is encoded by a variegated gene library. A variegated library of PKSRP variants can be produced by, for example, enzymatically ligating a mixture of synthetic oligonucleotides into gene sequences such that a degenerate set of potential PKSRP sequences is expressible as individual polypeptides, or alternatively, as a set of larger fusion polypeptides (e.g., for phage display) containing the set of PKSRP sequences therein. There are a variety of methods that can be used to produce libraries of potential PKSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PKSRP sequences. Methods for synthesizing degenerate oligonucleotides are known in the art. See, e.g., Narang, S. A., 1983, Tetrahedron 39:3; Itakura et al., 1984, Annu. Rev. Biochem. 53:323; Itakura et al., 1984, Science 198:1056; Ike et al., 1983, Nucleic Acid Res. 11:477.

In addition, libraries of fragments of the PKSRP coding regions can be used to generate a variegated population of PKSRP fragments for screening and subsequent selection of homologs of a PKSRP. In one embodiment, a library of coding sequence fragments can be generated by treating a double stranded PCR fragment of a PKSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the PKSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PKSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify PKSRP homologs (Arkin and Yourvan, 1992, PNAS 89:7811–7815; Delgrave et al., 1993, Polypeptide Engineering 6(3):327–331). In another embodiment, cell based assays can be exploited to analyze a variegated PKSRP library, using methods well known in the art. The present invention further provides a method of identifying a novel PKSRP, comprising (a) raising a specific antibody response to a PKSRP, or a fragment thereof, as described herein; (b) screening putative PKSRP material with the antibody, wherein specific binding of the antibody to the material indicates the presence of a potentially novel PKSRP; and (c) analyzing the bound material in comparison to known PKSRP, to determine its novelty.

As stated above, the present invention includes PKSRPs and homologs thereof. To determine the percent sequence identity of two amino acid sequences (e.g., one of the sequences of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., one of the sequences of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30) is occupied by the same amino acid residue as the corresponding position in the other sequence (e.g., a mutant form of the sequence selected from the polypeptide of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50–60%, preferably at least about 60–70%, and more preferably at least about 70–75%, 75–80%, 80–85%, 85–90% or 90–95%, and most preferably at least about 96%, 97%, 98%, 99% or more identical to an entire amino acid sequence shown in SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. In yet another embodiment, the isolated amino acid homologs included in the present invention are at least about 50–60%, preferably at least about 60–70%, and more preferably at least about 70–75%, 75–80%, 80–85%, 85–90% or 90–95%, and most preferably at least about 96%, 97%, 98%, 99% or more identical to an entire amino acid sequence encoded by a nucleic acid sequence shown in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29. In other embodiments, the PKSRP amino acid homologs have sequence identity over at least 15 contiguous amino acid residues, more preferably at least 25 contiguous amino acid residues, and most preferably at least 35 contiguous amino acid residues of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. In one embodiment of the present invention, the homolog has at least about 50–60%, preferably at least about 60–70%, more preferably at least about 70–75%, 75–80%, 80–85%, 85–90% or 90–95%, and even more preferably at least about 95%, 96%, 97%, 98%, 99% or more sequence identity with the kinase domain of PK-3 (amino acids 87–360 of SEQ ID NO:3) or PK-4 (amino acids 81–281 of SEQ ID NO:6).

In another preferred embodiment, an isolated nucleic acid homolog of the invention comprises a nucleotide sequence which is at least about 50–60%, preferably at least about 60–70%, more preferably at least about 70–75%, 75–80%, 80–85%, 85–90% or 90–95% and even more preferably at least about 95%, 96%, 97%, 98%, 99% or more identical to a nucleotide sequence shown in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29, or to a portion comprising at least 60 consecutive nucleotides thereof. The preferable length of sequence comparison for nucleic acids is at least 75 nucleotides, more preferably at least 100 nucleotides and most preferably the entire length of the coding region.

It is further preferred that the isolated nucleic acid homolog of the invention encodes a PKSRP, or portion thereof, that is at least 85% identical to an amino acid sequence of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30 and that functions as a modulator of an environmental stress response in a plant. In a more preferred embodiment, overexpression of the nucleic acid homolog in a plant increases the tolerance of the plant to an environmental stress. In a further preferred embodiment, the nucleic acid homolog encodes a PKSRP that functions as a protein kinase.

For the purposes of the invention, the percent sequence identity between two nucleic acid or polypeptide sequences may be determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29. In other embodiments, the nucleic acid is at least 30, 50, 100, 250 or more nucleotides in length. Preferably, an isolated nucleic acid homolog of the invention comprises a nucleotide sequence which hybridizes under highly stringent conditions to the nucleotide sequence shown in SEQ ID NO:2, SEQ ID NO:5 SEQ ID NO:8, SEQ ID NO:1, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29, and functions as a modulator of stress tolerance in a plant. In a further preferred embodiment, overexpression of the isolated nucleic acid homolog in a plant increases a plant's tolerance to an environmental stress. In an even further preferred embodiment, the isolated nucleic acid homolog encodes a PKSRP that functions as a protein kinase.

As used herein with regard to hybridization for DNA to DNA blot, the term "stringent conditions" refers to hybridization overnight at 60° C. in 10× Denharts solution, 6×SSC, 0.5% SDS and 100 µg/ml denatured salmon sperm DNA. Blots are washed sequentially at 62° C. for 30 minutes each time in 3×SSC/0.1% SDS, followed by 1×SSC/0.1% SDS and finally 0.1×SSC/0.1% SDS. As also used herein, "highly stringent conditions" refers to hybridization overnight at 65° C. in 10× Denharts solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS and finally 0.1×SSC/0.1% SDS. Methods for nucleic acid hybridizations are described in Meinkoth and Wahl, 1984, Anal. Biochem. 138:267–284; Ausubel et al. eds, 1995, Current Protocols in Molecular Biology, Chapter 2, Greene Publishing and Wiley-Interscience, New York; and Tijssen, 1993, Laboratory Techniques in Biochemistry and Molecular Biology: Hybridization with Nucleic Acid Probes, Part I, Chapter 2, Elsevier, N.Y. Preferably, an isolated nucleic acid molecule of the invention that hybridizes under stringent or highly stringent conditions to a sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens, Brassica napus, Glycine max,* or *Oryza sativa* PKSRP.

Using the above-described methods, and others known to those of skill in the art, one of ordinary skill in the art can isolate homologs of the PKSRPs comprising amino acid sequences shown in SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. One subset of these homologs are allelic variants. As used herein, the term "allelic variant" refers to a nucleotide sequence containing polymorphisms that lead to changes in the amino acid sequences of a PKSRP and that exist within a natural population (e.g., a plant species or variety). Such natural allelic variations can typically result in 1–5% variance in a PKSRP nucleic acid. Allelic variants can be identified by sequencing the nucleic acid sequence of interest in a number of different plants, which can be readily carried out by using hybridization probes to identify the same PKSRP genetic locus in those plants. Any and all such nucleic acid variations and resulting amino acid polymorphisms or variations in a PKSRP that are the result of natural allelic variation and that do not alter the functional activity of a PKSRP, are intended to be within the scope of the invention.

Moreover, nucleic acid molecules encoding PKSRPs from the same or other species such as PKSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338):631–637). Analogs, orthologs and paralogs of a naturally occurring PKSRP can differ from the naturally occurring PKSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80–85%, more preferably, 85–90% or 90–95%, and most preferably 95%, 96%, 97%, 98% or even 99% identity or sequence identity with all or part of a naturally occurring PKSRP amino acid sequence and will exhibit a function similar to a PKSRP. Preferably, a PKSRP ortholog of the present invention functions as a modulator of an environmental stress response in a plant and/or functions as a protein kinase. More preferably, a PKSRP ortholog increases the stress tolerance of a plant. In one embodiment, the PKSRP orthologs maintain the ability to participate in the metabolism of compounds necessary for the construction of cellular membranes in a plant, or in the transport of molecules across these membranes.

In addition to naturally-occurring variants of a PKSRP sequence that may exist in the population, the skilled artisan will further appreciate that changes can be introduced by mutation into a nucleotide sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29, thereby leading to changes in the amino acid sequence of the encoded PKSRP, without altering the functional activity of the PKSRP. For example, nucleotide substitutions leading to amino acid substitutions at "non-essential" amino acid residues can be made in a sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29. A "non-essential" amino acid residue is a residue that can be altered from the wild-type sequence of one of the PKSRPs without altering the activity of said PKSRP, whereas an "essential" amino acid residue is required for PKSRP activity. Other amino acid residues, however, (e.g., those that are not conserved or only semi-conserved in the domain having PKSRP activity) may not be essential for activity and thus are likely to be amenable to alteration without altering PKSRP activity.

Accordingly, another aspect of the invention pertains to nucleic acid molecules encoding PKSRPs that contain changes in amino acid residues that are not essential for PKSRP activity. Such PKSRPs differ in amino acid sequence from a sequence contained in SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, yet retain at least one of the PKSRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. Preferably, the polypeptide encoded by the nucleic acid molecule is at least about 50–60% identical to one of the sequences of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, more preferably at least about 60–70% identical to one of the sequences of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, even more preferably at least about 70–75%, 75–80%, 80–85%, 85–90%, 90–95% identical to one of the sequences of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30, and most preferably at least about 96%, 97%, 98%, or 99% identical to one of the sequences of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. The preferred PKSRP homologs of the present invention participate in the a stress tolerance response in a plant, or more particularly, participate in the transcription of a polypeptide involved in a stress tolerance response in a plant, and/or function as a protein kinase.

An isolated nucleic acid molecule encoding a PKSRP having sequence identity with a polypeptide sequence of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30 can be created by introducing one or more nucleotide substitutions, additions or deletions into a nucleotide sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29, respectively, such that one or more amino acid substitutions, additions, or deletions are introduced into the encoded polypeptide. Mutations can be introduced into one of the sequences of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PKSRP is preferably replaced with another amino acid residue from the same side chain family. Alternatively, in another embodiment, mutations can be introduced randomly along all or part of a PKSRP coding sequence, such as by saturation mutagenesis, and the resultant mutants can be screened for a PKSRP activity described herein to identify mutants that retain PKSRP activity. Following mutagenesis of one of the sequences of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29, the encoded polypeptide can be expressed recombinantly and the activity of the polypeptide can be determined by analyzing the stress tolerance of a plant expressing the polypeptide as described in Example 7.

Additionally, optimized PKSRP nucleic acids can be created. Preferably, an optimized PKSRP nucleic acid encodes a PKSRP that functions as a protein kinase and/or modulates a plant's tolerance to an environmental stress, and more preferably increases a plant's tolerance to an environmental stress upon its overexpression in the plant. As used herein, "optimized" refers to a nucleic acid that is genetically engineered to increase its expression in a given plant or animal. To provide plant optimized PKSRP nucleic acids, the DNA sequence of the gene can be modified to 1) comprise codons preferred by highly expressed plant genes; 2) comprise an A+T content in nucleotide base composition to that substantially found in plants; 3) form a plant initiation sequence; or 4) eliminate sequences that cause destabilization, inappropriate polyadenylation, degradation, and termination of RNA, or that form secondary structure hairpins or RNA splice sites. Increased expression of PKSRP nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. Nos. 5,380,831; 5,436,391; Perlack et al., 1991, Proc. Natl. Acad. Sci. USA 88:3324–3328; and Murray et al., 1989, Nucleic Acids Res. 17:477–498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1 \; Z \; X_n-Y_nX_n$ times 100 Z where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, and more preferably less than about 10%.

Hence, a PKSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized PKSRP nucleic acids of this invention also preferably have CG and TA doublet avoidance indices closely approximating those of the chosen host plant (i.e., *Physcomitrella patens, Brassica napus, Glycine max,* or *Oryza sativa*). More preferably these indices deviate from that of the host by no more than about 10–15%.

In addition to the nucleic acid molecules encoding the PKSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30.

The antisense nucleic acid can be complementary to an entire PKSRP coding strand, or to only a portion thereof. In one embodiment, an antisense nucleic acid molecule is antisense to a "coding region" of the coding strand of a nucleotide sequence encoding a PKSRP. The term "coding region" refers to the region of the nucleotide sequence comprising codons that are translated into amino acid residues (e.g., the entire coding region of PK-3 comprises nucleotides 138–1409 of SEQ ID NO:2, and the entire coding region of PK-4 comprises nucleotides 142–1395 of SEQ ID NO:5). In another embodiment, the antisense nucleic acid molecule is antisense to a "noncoding region" of the coding strand of a nucleotide sequence encoding a PKSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of PKSRP mRNA, but more preferably is an oligonucleotide which is antisense to only a portion of the coding or noncoding region of PKSRP mRNA. For example, the antisense oligonucleotide can be complementary to the region surrounding the translation start site of PKSRP mRNA. An antisense oligonucleotide can be, for example, about 5, 10, 15, 20, 25, 30, 35, 40, 45 or 50 nucleotides in length. Typically, the antisense molecules of the present invention comprise an RNA having 60–100% sequence identity with at least 14 consecutive nucleotides of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29 or a polynucleotide encoding SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. Preferably, the sequence identity will be at least 70%, more preferably at least 75%, 80%, 85%, 90%, 95%, 98% and most preferably 99%.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, Nucleic Acids. Res. 15:6625–6641). The antisense nucleic acid molecule can also comprise a 2'-o-methylribonucleotide (Inoue et al., 1987, Nucleic Acids Res. 15:6131–6148) or a chimeric RNA-DNA analogue (Inoue et al., 1987, FEBS Lett. 215: 327–330).

The antisense nucleic acid molecules of the invention are typically administered to a cell or generated in situ such that they hybridize with or bind to cellular mRNA and/or genomic DNA encoding a PKSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of a PKSRP polypeptide. By "ribozyme" is meant a catalytic RNA-based enzyme with ribonuclease activity which is capable of cleaving a single-stranded nucleic acid, such as an mRNA, to which it has a complementary region. Ribozymes (e.g., hammerhead ribozymes described in Haselhoff and Gerlach, 1988, Nature 334:585–591) can be used to catalytically cleave PKSRP mRNA transcripts to thereby inhibit translation of PKSRP mRNA. A ribozyme having specificity for a PKSRP-encoding nucleic acid can be designed based upon the nucleotide sequence of a PKSRP cDNA, as disclosed herein (i.e., SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a PKSRP-encoding mRNA. See, e.g., U.S. Pat. Nos. 4,987,071 and 5,116,742 to Cech et al. Alternatively, PKSRP mRNA can be used to select a catalytic RNA having a specific ribonuclease activity from a pool of RNA molecules. See, e.g., Bartel, D. and Szostak, J. W., 1993, Science 261:1411–1418. In preferred embodiments, the ribozyme will contain a portion having at least 7, 8, 9, 10, 12, 14, 16, 18 or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30 or a polypeptide having at least 70% sequence identity with SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30. The hybridizing RNAs may be substantially or completely complementary. By "substantially complementary," is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides or ribonucleotide analogs, such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238:645–650 and Cooney et al., 1988, Science 241:456–459) and cosuppression (Napoli et al., 1990, The Plant Cell 2:279–289) are known in the art. Partial and full-length cDNAs have been used for the cosuppression of endogenous plant genes. See, e.g., U.S. Pat. Nos. 4,801,340, 5,034,323, 5,231,020, and 5,283,184; Van der Kroll et al., 1990, The Plant Cell 2:291–299; Smith et al., 1990, Mol. Gen. Genetics 224:477–481 and Napoli et al., 1990, The Plant Cell 2:279–289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95% or more. The introduced sense polynucleotide need not be full length relative to the target gene or transcript. Preferably, the sense polynucleotide will have at least 65% sequence identity with at least 100 consecutive nucleotides of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29. The regions of identity can comprise introns and and/or exons and untranslated regions. The introduced sense polynucleotide may be present in the plant cell transiently, or may be stably integrated into a plant chromosome or extrachromosomal replicon.

Alternatively, PKSRP gene expression can be inhibited by targeting nucleotide sequences complementary to the regulatory region of a PKSRP nucleotide sequence (e.g., a PKSRP promoter and/or enhancer) to form triple helical structures that prevent transcription of a PKSRP gene in target cells. See generally, Helene, C., 1991, Anticancer Drug Des. 6(6):569–84; Helene, C. et al., 1992, Ann. N.Y. Acad. Sci. 660:27–36; and Maher, L. J., 1992, Bioassays 14(12):807–15.

In addition to the PKSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29; an anti-sense sequence of one of the sequences set forth in SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29; or naturally occurring mutants thereof. Primers based on a nucleotide sequence of SEQ ID NO:2, SEQ ID NO:5 SEQ ID NO:8, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID NO:29 can be used in PCR reactions to clone PKSRP homologs. Probes based on the PKSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PKSRP, such as by measuring a level of a PKSRP-encoding nucleic acid, in a sample of cells, e.g., detecting PKSRP mRNA levels or determining whether a genomic PKSRP gene has been mutated or deleted.

In particular, a useful method to ascertain the level of transcription of the gene (an indicator of the amount of mRNA available for translation to the gene product) is to perform a Northern blot. For reference, see, for example, Ausubel et al., 1988, Current Protocols in Molecular Biology, Wiley: N.Y. The information from a Northern blot at least partially demonstrates the degree of transcription of the transformed gene. Total cellular RNA can be prepared from cells, tissues or organs by several methods, all well-known in the art, such as that described in Bormann, E. R. et al., 1992, Mol. Microbiol. 6:317–326. To assess the presence or relative quantity of polypeptide translated from this mRNA, standard techniques, such as a Western blot, may be employed. These techniques are well known to one of ordinary skill in the art. See, for example, Ausubel et al., 1988, Current Protocols in Molecular Biology, Wiley: N.Y.

The invention further provides an isolated recombinant expression vector comprising a PKSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., PKSRPs, mutant forms of PKSRPs, fusion polypeptides, etc.).

The recombinant expression vectors of the invention can be designed for expression of PKSRPs in prokaryotic or eukaryotic cells. For example, PKSRP genes can be expressed in bacterial cells such as *C. glutamicum*, insect cells (using baculovirus expression vectors), yeast and other fungal cells (See Romanos, M. A. et al., 1992, Foreign gene expression in yeast: a review, Yeast 8:423–488; van den Hondel, C.A.M.J.J. et al., 1991, Heterologous gene expression in filamentous fungi, in: More Gene Manipulations in Fungi, J. W. Bennet & L. L. Lasure, eds., p. 396–428: Academic Press: San Diego; and van den Hondel, C.A.M.J.J. & Punt, P. J., 1991, Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999, Marine Biotechnology 1(3):239–251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus *Stylonychia lemnae* with vectors following a transformation method as described in PCT Application No. WO 98/01572, and multicellular plant cells (See Schmidt, R. and Willmitzer, L., 1988, High efficiency *Agrobacterium tumefaciens*-mediated transformation of *Arabidopsis thaliana* leaf and cotyledon explants, Plant Cell Rep. 583–586; Plant Molecular Biology and Biotechnology, C Press, Boca Raton, Fla., chapter 6/7, S.71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991, Annu. Rev. Plant Physiol. Plant Molec. Biol. 42:205–225 and references cited therein) or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31–40), pMAL (New England Biolabs, Beverly, Mass.) and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the PKSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant PKSRP unfused to GST can be recovered by cleavage of the fusion polypeptide with thrombin.

Examples of suitable inducible non-fusion *E. coli* expression vectors include pTrc (Amann et al., 1988, Gene 69:301–315) and pET lid (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a co-expressed viral RNA polymerase (T7 gn1). This viral polymerase is supplied by host strains BL21(DE3) or HMS 174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology: Methods in Enzymology 185, Academic Press, San Diego, Calif. (1990) 119–128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111–2118). Such alteration of nucleic acid sequences of the invention can be carried out by standard DNA synthesis techniques.

In another embodiment, the PKSRP expression vector is a yeast expression vector. Examples of vectors for expression in yeast *S. cerevisiae* include pYepSec1 (Baldari, et al., 1987, EMBO J. 6:229–234), pMFa (Ku jan and Herskowitz, 1982, Cell 30:933–943), pJRY88 (Schultz et al., 1987, Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C.A.M.J.J. & Punt, P. J., 1991, "Gene transfer systems and vector development for filamentous fungi," in: Applied Molecular Genetics of Fungi, J. F. Peberdy, et al., eds., p. 1–28, Cambridge University Press: Cambridge.

Alternatively, the PKSRPs of the invention can be expressed in insect cells using baculovirus expression vectors. Baculovirus vectors available for expression of polypeptides in cultured insect cells (e.g., Sf 9 cells) include the pAc series (Smith et al., 1983, Mol. Cell Biol. 3:2156–2165) and the pVL series (Lucklow and Summers, 1989, Virology 170:31–39).

In yet another embodiment, a PKSRP nucleic acid of the invention is expressed in mammalian cells using a mammalian expression vector. Examples of mammalian expression vectors include pCDM8 (Seed, B., 1987, Nature 329:840) and pMT2PC (Kaufman et al., 1987, EMBO J. 6:187–195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual. $2^{nd}$, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268–277), lymphoid-specific promoters (Calame and Eaton, 1988, Adv. Immunol. 43:235–275), in particular promoters of T cell receptors (Winoto and Baltimore, 1989, EMBO J. 8:729–733) and immunoglobulins (Banerji et al., 1983, Cell 33:729–740; Queen and Baltimore, 1983, Cell 33:741–748), neuron-specific promoters (e.g., the neurofilament promoter; Byrne and Ruddle, 1989, PNAS 86:5473–5477), pancreas-specific promoters (Edlund et al., 1985, Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, Science 249:374–379) and the fetopolypeptide promoter (Campes and Tilghman, 1989, Genes Dev. 3:537–546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, and methotrexate, or in plants that confer resistance towards a herbicide such as glyphosate or glufosinate. Nucleic acid molecules encoding a selectable marker can be introduced into a host cell on the same vector as that encoding a PKSRP or can be introduced on a separate vector. Cells stably transfected with the introduced nucleic acid molecule can be identified by, for example, drug selection (e.g., cells that have incorporated the selectable marker gene will survive, while the other cells die).

In a preferred embodiment of the present invention, the PKSRPs are expressed in plants and plants cells such as unicellular plant cells (e.g. algae) (See Falciatore et al., 1999, Marine Biotechnology 1(3):239–251 and references therein) and plant cells from higher plants (e.g., the spermatophytes, such as crop plants). A PKSRP may be "introduced" into a plant cell by any means, including transfection, transformation or transduction, electroporation, particle bombardment, agroinfection, and the like. One transformation method known to those of skill in the art is the dipping of a flowering plant into an *Agrobacteria* solution, wherein the *Agrobacteria* contains the PKSRP nucleic acid, followed by breeding of the transformed gametes.

Other suitable methods for transforming or transfecting host cells including plant cells can be found in Sambrook, et al., Molecular Cloning: A Laboratory Manual. $2^{nd}$, ed., Cold Spring Harbor Laboratory, Cold Spring Harbor Laboratory Press, Cold Spring Harbor, N.Y., 1989, and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of a PKSRP into a plant is achieved by *Agrobacterium* mediated gene transfer. *Agrobacterium* mediated plant transformation can be performed using for example the GV3101 (pMP90) (Koncz and Schell, 1986, Mol. Gen. Genet. 204: 383–396) or LBA4404 (Clontech) *Agrobacterium tumefaciens* strain. Transformation can be performed by standard transformation and regeneration techniques (Deblaere et al., 1994, Nucl. Acids Res. 13:4777–4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT 11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989, Plant cell Report 8:238–242; De Block et al., 1989, Plant Physiol. 91:694–701). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994, Plant Cell Report 13:282–285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced PKSRP may be maintained in the plant cell stably if it is incorporated into a non-chromosomal autonomous replicon or integrated into the plant chromosomes. Alternatively, the introduced PKSRP may be present on an extra-chromosomal non-replicating vector and be transiently expressed or transiently active.

In one embodiment, a homologous recombinant microorganism can be created wherein the PKSRP is integrated into a chromosome, a vector is prepared which contains at least a portion of a PKSRP gene into which a deletion, addition, or substitution has been introduced to thereby alter, e.g., functionally disrupt, the PKSRP gene. Preferably, the PKSRP gene is a *Physcomitrella patens, Brassica napus, Glycine max,* or *Oryza sativa* PKSRP gene, but it can be a homolog from a related plant or even from a mammalian, yeast, or insect source. In one embodiment, the vector is designed such that, upon homologous recombination, the endogenous PKSRP gene is functionally disrupted (i.e., no longer encodes a functional polypeptide; also referred to as a knock-out vector). Alternatively, the vector can be designed such that, upon homologous recombination, the endogenous PKSRP gene is mutated or otherwise altered but still encodes a functional polypeptide (e.g., the upstream regulatory region can be altered to thereby alter the expression of the endogenous PKSRP). To create a point mutation via homologous recombination, DNA-RNA hybrids can be used in a technique known as chimeraplasty (Cole-Strauss et al., 1999, Nucleic Acids Research 27(5):1323–1330 and Kmiec, 1999 Gene therapy American Scientist. 87(3):240–247). Homologous recombination procedures in *Physcomitrella patens* are also well known in the art and are contemplated for use herein.

Whereas in the homologous recombination vector, the altered portion of the PKSRP gene is flanked at its 5' and 3' ends by an additional nucleic acid molecule of the PKSRP gene to allow for homologous recombination to occur between the exogenous PKSRP gene carried by the vector and an endogenous PKSRP gene, in a microorganism or plant. The additional flanking PKSRP nucleic acid molecule is of sufficient length for successful homologous recombination with the endogenous gene. Typically, several hundreds of base pairs up to kilobases of flanking DNA (both at the 5' and 3' ends) are included in the vector. See, e.g., Thomas, K. R., and Capecchi, M. R., 1987, Cell 51:503 for a description of homologous recombination vectors or Strepp et al., 1998, PNAS, 95 (8):4368–4373 for cDNA based recombination in *Physcomitrella patens*). The vector is introduced into a microorganism or plant cell (e.g., via polyethylene glycol mediated DNA), and cells in which the introduced PKSRP gene has homologously recombined with the endogenous PKSRP gene are selected using art-known techniques.

In another embodiment, recombinant microorganisms can be produced that contain selected systems which allow for regulated expression of the introduced gene. For example, inclusion of a PKSRP gene on a vector placing it under control of the lac operon permits expression of the PKSRP gene only in the presence of IPTG. Such regulatory systems are well known in the art.

Whether present in an extra-chromosomal non-replicating vector or a vector that is integrated into a chromosome, the PKSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693–8711). Examples of plant expression vectors include those detailed in: Becker, D. et al., 1992, New plant binary vectors with selectable markers located proximal to the left border, Plant Mol. Biol. 20: 1195–1197; and Bevan, M. W., 1984, Binary *Agrobacterium* vectors for plant transformation, Nucl. Acid. Res. 12:8711–8721; and Vectors for Gene Transfer in Higher Plants; in: Transgenic Plants, Vol. 1, Engineering and Utilization, eds.: Kung and R. Wu, Academic Press, 1993, S. 15–38.

Plant gene expression should be operatively linked to an appropriate promoter conferring gene expression in a timely, cell or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters (Odell et al., 1985, Nature 313:810–812), the sX CaMV 35S promoter (Kay et al., 1987, Science 236:1299–1302) the Sep1 promoter, the rice actin promoter (McElroy et al., 1990, Plant Cell 2:163–171), the *Arabidopsis* actin promoter, the ubiquitan promoter (Christensen et al., 1989, Plant Molec Biol 18:675–689);

pEmu (Last et al., 1991, Theor Appl Genet 81:581–588), the figwort mosaic virus 35S promoter, the Smas promoter (Velten et al., 1984, EMBO J. 3:2723–2730), the GRP1-8 promoter, the cinnamyl alcohol dehydrogenase promoter (U.S. Pat. No. 5,683,439), promoters from the T-DNA of Agrobacterium, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoter from tobacco, *Arabidopsis*, and maize are inducible by infection with a pathogen; and the Adhl promoter is induced by hypoxia and cold stress. Plant gene expression can also be facilitated via an inducible promoter (For a review, see Gatz, 1997, Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397–404), and an ethanol inducible promoter (PCT Application No. WO 93/21334).

In one preferred embodiment of the present invention, the inducible promoter is a stress-inducible promoter. Stress inducible promoters include, but are not limited to, Cor78 (Chak et al., 2000, Planta 210:875–883; Hovath et al., 1993, Plant Physiol. 103:1047–1053), Cor15a (Artus et al., 1996, PNAS 93(23):13404–09), Rci2A (Medina et al., 2001, Plant Physiol. 125:1655–66; Nylander et al., 2001, Plant Mol. Biol. 45:341–52; Navarre and Goffeau, 2000, EMBO J. 19:2515–24; Capel et al., 1997, Plant Physiol. 115:569–76), Rd22 (Xiong et al., 2001, Plant Cell 13:2063–83; Abe et al., 1997, Plant Cell 9:1859–68; Iwasaki et al., 1995, Mol. Gen. Genet. 247:391–8), cDet6 (Lang and Palve, 1992, Plant Mol. Biol. 20:951–62), ADH1 (Hoeren et al., 1998, Genetics 149:479–90), KAT1 (Nakamura et al., 1995, Plant Physiol. 109:371–4), KST1 (Müller-Röber et al., 1995, EMBO 14:2409–16), Rhal (Terryn et al., 1993, Plant Cell 5:1761–9; Terryn et al., 1992, FEBS Lett. 299(3):287–90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8:1477–90), GH3 (Liu et al., 1994, Plant Cell 6:645–57), the pathogen inducible PRP1-gene promoter (Ward et al., 1993, Plant. Mol. Biol. 22:361–366), the heat inducible hsp80-promoter from tomato (U.S. Pat. No. 5,187,267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331–340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., 1989, BioEssays 10:108. Examples of seed preferred promoters include, but are not limited to, cellulose synthase (ce1A), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from Vicia faba (Baeumlein et al., 1991, Mol Gen Genet. 225(3):459–67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233–9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729–736).

The invention further provides a recombinant expression vector comprising a PKSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PKSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a PKSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

A host cell of the invention, such as a prokaryotic or eukaryotic host cell in culture, can be used to produce (i.e., express) a PKSRP. Accordingly, the invention further provides methods for producing PKSRPs using the host cells of the invention. In one embodiment, the method comprises culturing the host cell of invention (into which a recombinant expression vector encoding a PKSRP has been introduced, or into which genome has been introduced a gene encoding a wild-type or altered PKSRP) in a suitable medium until PKSRP is produced. In another embodiment, the method further comprises isolating PKSRPs from the medium or the host cell.

Another aspect of the invention pertains to isolated PKSRPs, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of PKSRP in which the polypeptide is separated from some of the cellular components of the cells in which it is naturally or recombinantly produced. In one embodiment, the language "substantially free of cellular material" includes preparations of a PKSRP having less than about 30% (by dry weight) of non-PKSRP material (also referred to herein as a "contaminating polypeptide"), more preferably less than about 20% of non-PKSRP material, still more preferably less than about 10% of non-PKSRP material, and most preferably less than about 5% non-PKSRP material.

When the PKSRP or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of PKSRP in which the polypeptide is separated from chemical precursors or other chemicals that are involved in the synthesis of the polypeptide. In one embodiment, the language "substantially free of chemical precursors or other chemicals" includes preparations of a PKSRP having less than about 30% (by dry weight) of chemical precursors or non-PKSRP chemicals, more preferably less than about 20% chemical precursors or non-PKSRP chemicals, still more preferably less than about 10% chemical precursors or non-PKSRP chemicals, and most preferably less than about 5% chemical precursors or non-PKSRP chemicals. In preferred embodiments, isolated polypeptides, or biologically active portions thereof, lack contaminating polypeptides from the same organism from which the PKSRP is derived. Typically, such polypeptides are produced by recombinant expression of, for example, a *Physcomitrella patens, Brassica napus, Glycine max,* or *Oryza sativa* PKSRP in plants other than *Physcomitrella patens, Brassica napus, Glycine max,* or *Oryza sativa*, or microorganisms such as *C. glutamicum*, ciliates, algae or fungi.

The nucleic acid molecules, polypeptides, polypeptide homologs, fusion polypeptides, primers, vectors, and host cells described herein can be used in one or more of the following methods: identification of *Physcomitrella patens, Brassica napus, Glycine max,* or *Oryza sativa* and related organisms; mapping of genomes of organisms related to *Physcomitrella patens, Brassica napus, Glycine max,* or *Oryza sativa*; identification and localization of *Physcomitrella patens, Brassica napus, Glycine max,* or *Oryza sativa* sequences of interest; evolutionary studies; determination of PKSRP regions required for function; modulation of a PKSRP activity; modulation of the metabolism of one or more cell functions; modulation of the transmembrane transport of one or more compounds; modulation of stress resistance; and modulation of expression of PKSRP nucleic acids.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PKSRP nucleic acid molecules of the invention have a variety of uses. Most importantly, the nucleic acid and amino acid sequences of the present invention can be used to transform plants, thereby inducing tolerance to stresses such as drought, high salinity and cold or lodging. The present invention therefore provides a transgenic plant transformed by a PKSRP nucleic acid, wherein expression of the nucleic acid sequence in the plant results in increased tolerance to environmental stress or increased resistance to lodging as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass, and forage crops, for example.

In particular, the present invention describes using the expression of PK-3, PK-4, PK-10, and PK-11 of *Physcomitrella patens;* the BnPK-1, BnPK-2, BnPK-3, and BnPK-4 of *Brassica napus;* the GmPK-1, GmPK-2, GmPK-3, and GmPK-4 of *Glycine max*; and the OsPK-1 of *Oryza sativa* to engineer drought-tolerant, salt-tolerant, cold-tolerant, and/or lodging-resistant plants. This strategy has herein been demonstrated for *Arabidopsis thaliana*, Rapeseed/Canola, soybeans, corn, and wheat, but its application is not restricted to these plants. Accordingly, the invention provides a transgenic plant containing a PKSRP such as PK-3 as defined in SEQ ID NO:3, PK-4 as defined in SEQ ID NO:6, PK-10 as defined in SEQ ID NO:9, PK-11 as defined in SEQ ID NO:12, BnPK-1 as defined in SEQ ID NO:14, BnPK-2 as defined in SEQ ID NO:16, BnPK-3 as defined in SEQ ID NO:18, BnPK-4 as defined in SEQ ID NO:20, GmPK-1 as defined in SEQ ID NO:22, GmPK-2 as defined in SEQ ID NO:24, GmPK-3 as defined in SEQ ID NO:26, GmPK-4 as defined in SEQ ID NO:28, and OsPK-1 as defined in SEQ ID NO:30, wherein the plant has an increased tolerance to an environmental stress selected from drought, increased salt, decreased or increased temperature, or lodging. In preferred embodiments, the environmental stress is drought or decreased temperature.

Accordingly, the invention provides a method of producing a transgenic plant with a PKSRP coding nucleic acid, wherein expression of the nucleic acid in the plant results in increased tolerance to environmental stress as compared to a wild type variety of the plant comprising: (a) introducing into a plant cell an expression vector comprising a PKSRP nucleic acid, and (b) generating from the plant cell a transgenic plant with an increased tolerance to environmental stress as compared to a wild type variety of the plant. Also included within the present invention are methods of increasing a plant's resistance to lodging, comprising transforming a plant cell with an expression cassette comprising a nucleic acid encoding a PKSRP and generating a transgenic plant from the transformed plant cell. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the PKSRP nucleic acid encodes a protein comprising SEQ ID NO:3, SEQ ID NO:6, SEQ ID NO:9, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, or SEQ ID NO:30.

The present invention also provides a method of modulating a plant's tolerance to an environmental stress comprising, modifying the expression of a PKSRP coding nucleic acid in the plant. The plant's tolerance to the environmental stress can be increased or decreased as achieved by increasing or decreasing the expression of a PKSRP, respectively. Preferably, the plant's tolerance to the environmental stress is increased by increasing expression of a PKSRP. Expression of a PKSRP can be modified by any method known to those of skill in the art. The methods of increasing expression of PKSRPs can be used wherein the plant is either transgenic or not transgenic. In cases when the plant is transgenic, the plant can be transformed with a vector containing any of the above described PKSRP coding nucleic acids, or the plant can be transformed with a promoter that directs expression of native PKSRP in the plant, for example. The invention provides that such a promoter can be tissue specific, developmentally regulated, or stress-inducible. Alternatively, non-transgenic plants can have native PKSRP expression modified by inducing a native promoter. The expression of PK-3 as defined in SEQ ID NO:2, PK-4 as defined in SEQ ID NO:5, PK-10 as defined in SEQ ID NO:8, PK-11 as defined in SEQ ID NO:11, BnPK-1 as defined in SEQ ID NO:13, BnPK-2 as defined in SEQ ID NO:15, BnPK-3 as defined in SEQ ID NO:17, BnPK-4 as defined in SEQ ID NO:19, GmPK-1 as defined in SEQ ID NO:21, GmPK-2 as defined in SEQ ID NO:23, GmPK-3 as defined in SEQ ID NO:25, GmPK-4 as defined in SEQ ID NO:27, and OsPK-1 as defined in SEQ ID NO:29 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275:657).

In a preferred embodiment, transcription of the PKSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as a PKSRP nucleic acid. Therefore, activating and repressing ZFPs can be created that specifically recognize the PKSRP promoters described above and used to increase or decrease PKSRP expression in a plant, thereby modulating the stress tolerance of the plant. The present invention also includes identification of the homologs of SEQ ID NO:2, PK-4 as defined in SEQ ID NO:5, PK-10 as defined in SEQ ID NO:8, PK-11 as defined in SEQ ID NO:11, BnPK-1 as defined in SEQ ID NO:13, BnPK-2 as defined in SEQ ID NO:15, BnPK-3 as defined in SEQ ID NO:17, BnPK-4 as defined in SEQ ID NO:19, GmPK-1 as defined in SEQ ID NO:21, GmPK-2 as defined in SEQ ID NO:23, GmPK-3 as defined in SEQ ID NO:25, GmPK-4 as defined in SEQ ID NO:27, and OsPK-1 as defined in SEQ ID NO:29 in a target plant as well as the homolog's promoter. The invention also provides a method of increasing expression of a gene of interest within a host cell as compared to a wild type variety of the host cell, wherein the gene of interest is transcribed in response to a PKSRP, comprising: (a) transforming the host cell with an expression vector comprising a PKSRP coding nucleic acid, and (b) expressing the PKSRP within the host cell, thereby increasing the expression of the gene transcribed in response to the PKSRP, as compared to a wild type variety of the host cell.

In addition to introducing the PKSRP nucleic acid sequences into transgenic plants, these sequences can also be used to identify an organism as being *Physcomitrella patens, Brassica napus, Glycine max, Oryza sativa*, or a close relative thereof. Also, they may be used to identify the presence of *Physcomitrella patens, Brassica napus, Glycine max, Oryza sativa*, or a relative thereof in a mixed population of microorganisms. The invention provides the nucleic acid sequences of a number of *Physcomitrella patens, Brassica napus, Glycine max*, and *Oryza sativa* genes; by probing the extracted genomic DNA of a culture of a unique or mixed population of microorganisms under stringent conditions with a probe spanning a region of a *Physcomitrella patens, Brassica napus, Glycine max*, or *Oryza sativa* gene which is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens, Brassica napus, Glycine max*, and *Oryza sativa* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The PKSRP nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

Manipulation of the PKSRP nucleic acid molecules of the invention may result in the production of PKSRPs having functional differences from the wild-type PKSRPs. These polypeptides may be improved in efficiency or activity, may be present in greater numbers in the cell than is usual, or may be decreased in efficiency or activity.

There are a number of mechanisms by which the alteration of a PKSRP of the invention may directly affect stress response and/or stress tolerance. In the case of plants expressing PKSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, P. A. et al., 1988, Bioseparations: downstream processing for biotechnology, John Wiley and Sons; Kennedy, J. F. and Cabral, J. M. S., 1992, Recovery processes for biological materials, John Wiley and Sons; Shaeiwitz, J. A. and Henry, J. D., 1988, Biochemical separations, in: Ulmann's Encyclopedia of Industrial Chemistry, vol. B3, Chapter 11, page 1–27, VCH: Weinheim; and Dechow, F. J., 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived therefrom can then be assayed for fail or alteration of their tolerance to drought, salt, temperature stress, and lodging.

The engineering of one or more PKSRP genes of the invention may also result in PKSRPs having altered activities which indirectly impact the stress response and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species) which may actively interfere with these same metabolic processes. For example, peroxynitrite is known to nitrate tyrosine side chains, thereby inactivating some enzymes having tyrosine in the active site (Groves, J. T., 1999, Curr. Opin. Chem. Biol. 3(2):226–235). While these products are typically excreted, cells can be genetically altered to transport more products than is typical for a wild-type cell. By optimizing the activity of one or more PKSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 "Non-Chimeric Mutational Vectors" and Puttaraju et al., 1999, Spliceosome-mediated RNA trans-splicing as a tool for gene therapy, Nature Biotechnology 17:246–252.

The aforementioned mutagenesis strategies for PKSRPs resulting in increased stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated PKSRP nucleic acid and polypeptide molecules such that the stress tolerance is improved.

The present invention also provides antibodies that specifically bind to a PKSRP, or a portion thereof, as encoded by a nucleic acid described herein. Antibodies can be made by many well-known methods (See, e.g. Harlow and Lane, "Antibodies; A Laboratory Manual," Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., 1992, Bio/Technology 10:163–167; Bebbington et al., 1992, Bio/Technology 10:169–175.

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual," Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane, "Antibodies, A Laboratory Manual," Cold Spring Harbor Publications, New York, (1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella Patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonema developed from the haploid spore as a chloroplast-rich chlorenema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-}$m$^{-2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000×g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H$_2$O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and CODA Library Construction from *Physcomitrella Patens*

For the investigation of transcripts, both total RNA and poly-(A)+ RNA were isolated. The total RNA was obtained from wild-type 9 day old protonemata following the GTC-method (Reski et al., 1994, Mol. Gen. Genet., 244:352–359). The Poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella Patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

| | |
|---|---|
| 5'-CAGGAAACAGCTATGACC-3' | SEQ ID NO:31 |
| 5'-CTAAAGGGAACAAAAGCTG-3' | SEQ ID NO:32 |
| 5'-TGTAAAACGACGGCCAGT-3' | SEQ ID NO:33 |

Sequences were processed and annotated using the software package EST-MAX commercially provided by BioMax (Munich, Germany). The program incorporates practically all bioinformatics methods important for functional and structural characterization of polypeptide sequences. The most important algorithms incorporated in EST-MAX are: FASTA (Very sensitive sequence database searches with estimates of statistical significance; Pearson W. R., 1990, Rapid and sensitive sequence comparison with FASTP and FASTA, Methods Enzymol. 183:63–98); BLAST (Very sensitive sequence database searches with estimates of statistical significance; Altschul S. F. et al., Basic local alignment search tool, Journal of Molecular Biology 215:403–10); PREDATOR (High-accuracy secondary structure prediction from single and multiple sequences, Frishman, D. and Argos, P., 1997, 75% accuracy in polypeptide secondary structure prediction, Polypeptides, 27:329–335); CLUSTAL W (Multiple sequence alignment; Thompson, J. D. et al., 1994, CLUSTAL W: improving the sensitivity of progressive multiple sequence alignment through sequence weighting, positions-specific gap penalties and weight matrix choice. Nucleic Acids Research, 22:4673–4680); TMAP (Transmembrane region prediction from multiply aligned sequences; Persson, B. and Argos, P., 1994, Prediction of transmembrane segments in polypeptides utilizing multiple sequence alignments, J. Mol. Biol. 237:182–192); ALOM2 (Transmembrane region prediction from single sequences; Klein, P. et al., Prediction of polypeptide function from sequence properties: A discriminate analysis of a database. Biochim. Biophys. Acta 787:221–226 (1984). Version 2 by Dr. K. Nakai); PROSEARCH (Detection of PROSITE polypeptide sequence patterns; Kolakowski L. F. Jr. et al., 1992, ProSearch: fast searching of polypeptide sequences with regular expression patterns related to polypeptide structure and function, Biotechniques 13:919–921); BLIMPS (Similarity searches against a database of ungapped blocks; J. C. Wallace and Henikoff S., 1992); and PATMAT (A searching and extraction program for sequence, pattern and block queries and databases, CABIOS 8:249–254. Written by Bill Alford.).

Example 5

Identification of *Physcomitrella Patens* ORFs Corresponding to PK-3, PK-4, PK-10, and PK-11

The *Physcomitrella patens* partial cDNAs (ESTs) for partial PK-3 (SEQ ID NO:1), partial PK-4 (SEQ ID NO:4), partial PK-10 (SEQ ID NO:7), and partial PK-11 (SEQ ID NO:10) were identified in the *Physcomitrella patens* EST sequencing program using the program EST-MAX through BLAST analysis. These particular clones, which were found to encode Protein Kinases, were chosen for further analyses.

TABLE 1

Degree of Amino Acid Identity and Similarity of PK-3 and Other Kinases
(Pairwise Comparison was used: gap penalty: 10; gap extension
penalty: 0.1; score matrix: blosum62)

| Swiss-Prot # | P51139 | Q40518 | P43288 | P43289 | Q9LYJ6 |
|---|---|---|---|---|---|
| Protein name | Glycogen Synthase Kinase-3 Homolog MSK-3 | Shaggy-Related Protein Kinase NTK-1 | Shaggy-Related Protein Kinase Alpha | Shaggy-Related Protein Kinase Gamma | Protein Kinase MSK-3-Like |

TABLE 1-continued

Degree of Amino Acid Identity and Similarity of PK-3 and Other Kinases (Pairwise Comparison was used: gap penalty: 10; gap extension penalty: 0.1; score matrix: blosum62)

| Swiss-Prot # | P51139 | Q40518 | P43288 | P43289 | Q9LYJ6 |
|---|---|---|---|---|---|
| Species | *Medicago sativa* (Alfalfa) | *Nicotiana tabacum* (Common tobacco) | *Arabidopsis thaliana* (Mouse-ear cress) | *Arabidopsis thaliana* (Mouse-ear cress) | *Arabidopsis thaliana* (Mouse-ear cress) |
| Identity % | 78% | 79% | 79% | 80% | 79% |
| Similarity % | 86% | 86% | 86% | 87% | 87% |

TABLE 2

Degree of Amino Acid Identity and Similarity of PK-4 and Other Kinases (Pairwise Comparison was used: gap penalty: 10; gap extension penalty: 0.1; score matrix: blosum62)

| Swiss-Prot # | Q9SZI1 | Q9ZUP4 | P42158 | Q39050 | Q9LW62 |
|---|---|---|---|---|---|
| Polypeptide name | COL-0 Casein Kinase I-Like Protein | Putative Casein Kinase I | Casein Kinase I, Delta Isoform Like | Casein Kinase I | Casein Kinase |
| Species | *Arabidopsis thaliana* (Mouse-ear cress) | *Arabidopsis thaliana* (Mouse-ear cress) | *Arabidopsis thaliana* (Mouse-ear cress) | *Arabidopsis thaliana* (Mouse-ear cress) | *Arabidopsis thaliana* (Mouse-ear cress) |
| Identity % | 35% | 35% | 37% | 35% | 35% |
| Similarity % | 46% | 44% | 47% | 45% | 44% |

TABLE 3

Degree of Amino Acid Identity and Similarity of PK-10 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| PK-10 | AAG51974 | Putative Leucine-Rich Repeat Transmembrane Protein Kinase 1 | *Arabidopsis thaliana* | 45% | 57% |

TABLE 4

Degree of Amino Acid Identity and Similarity of PK-11 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| PK-11 | AAK72257.1 | CBL-Interacting Protein Kinase 24 | *Arabidopsis thaliana* | 64% | 76% |

Example 6

Cloning of the Full-Length *Physcomitrella Patens* cDNA Encoding for PK-3, PK-4, PK-10, and PK-11

To isolate the clone encoding full-length PK-3 (SEQ ID NO:2), PCR was performed (as described below in Full-Length Amplification) using the original ESTs described in Example 5 as template. The primers used for amplification are listed below in Table 5.

To isolate the clones encoding PK-4 (SEQ ID NO:5), PK-10 (SEQ ID NO:8), and PK-11 (SEQ ID NO:11) from *Physcomitrella patens*, cDNA libraries were created with SMART RACE cDNA Amplification kit (Clontech Laboratories) following the manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol

The EST sequences of PK-4 (SEQ ID NO:4), PK-10 (SEQ ID NO:7), and PK-11 (SEQ ID NO:10) identified from the database search as described in Example 5 were used to design oligos for RACE (See Table 5). The extended sequence for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding region of PK-4, PK-10, and PK-11 and were used to design oligos for full-length cloning of the respective gene (See below Full-Length Amplification).

Full-Length Amplification

A full-length clone corresponding to PK-3 (SEQ ID NO:2) was obtained by performing polymerase chain reaction (PCR) with gene-specific primers (See Table 5) and the original EST as the template. The conditions for the reaction were standard conditions with PWO DNA polymerase (Roche). PCR was performed according to standard conditions and to manufacturer's protocols (Sambrook et al., 1989, Molecular Cloning, A Laboratory Manual, 2nd Edition, Cold Spring Harbor Laboratory Press, Cold Spring Harbor, N.Y., Biometra T3 Thermocycler). The parameters for the reaction were: five minutes at 94° C. followed by five cycles of one minute at 94° C., one minute at 50° C., and 1.5 minutes at 72° C. This was followed by twenty five cycles of one minute at 94° C., one minute at 65° C., and 1.5 minutes at 72° C.

Full-length clones for PK-4 (SEQ ID NO:5), PK-10 (SEQ ID NO:8), and PK-11 (SEQ ID NO:11) were isolated by repeating the RACE method but using the gene-specific primers as given in Table 5.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989, Molecular Cloning, A Laboratory Manual. 2nd Edition, Cold Spring Harbor Laboratory Press, Cold Spring Harbor, N.Y.). Transformed cells were selected for on LB agar containing 100 µg/ml carbenicillin, 0.8 mg X-gal (5-bromo-4-chloro-3-indolyl-β-D-galactoside), and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

TABLE 5

Scheme and Primers Used for Cloning of Full-Length Clones

| Gene | Sites in the final product | Isolation Method | Primers Race | | Primers RT-PCR | |
|---|---|---|---|---|---|---|
| PK-3 | XmaI/SacI | PCR of original EST clone | | | RC021: 5'ATCCCGGGCGA GTCTTCTATGGC ATCTGCGACT3' | (SEQ ID NO:34) |
| | | | | | RC022: 5'ATGAGCTCAAT ATCAGGAGTTGC ACCCTTCAAC3' | (SEQ ID NO:35) |
| PK-4 | XmaI/EcoRV | 5' RACE and RT-PCR for FL clone | RC072: 5'TGTGTCTACGT GTCGCGGGGTC GAT3' | (SEQ ID NO:36) | RC133N: 5'ATCCCGGGAGG CATTGAACTACC TGGAGTGAG3' | (SEQ ID NO:37) |
| | | | | | RC134N: 5'GCGATATCGTT GAACTAGTAATC TGTGTTAACTT3' | (SEQ ID NO:38) |
| PK-10 | XmaI/SacI | 5' RACE and RT-PCR for FL clone | NVT: 5'CTGCGACGGA AAACTCTCTTGC TGT3' | (SEQ ID NO:39) | RC580: 5'ATCCCGGGTGT CGGAATTCGTC ACAATGAGCT3' | (SEQ ID NO:46) |
| | | | | | RC834:5'GCGAGC TCGTGCGAATCA TGTACTCCCATC ACAC3' | (SEQ ID NO:40) |
| PK-11 | XmaI/SacI | 5' RACE and RT-PCR for FL clone | RC253: 5'GCAGCGGTAT ATCCTTGCTCCT CATC3' | (SEQ ID NO:44) | RC1158: 5'ATCCCGGGTTT CTGGAATAGCTC AGAAGCGT3' | (SEQ ID NO:47) |
| | | | RC520:5'CGATGT GAGACGCCCTT GCTGTGGCA3' | (SEQ ID NO:45) | RC1159:5'CGGAG CTCGATGCAGCG GTATATCCTTGC TCCT3' | (SEQ ID NO:42) |
| | | | RC721:5'GCAAC GACTTGCCAGA ACCTCGTGC3' | (SEQ ID NO:41) | | |

Tissue Harvest, RNA Isolation, and cDNA Library Construction

Canola, soybean, and rice plants were grown under a variety of conditions and treatments, and different tissues were harvested at various developmental stages. Plant growth and harvesting were done in a strategic manner such that the probability of harvesting all expressable genes in at least one or more of the resulting libraries is maximized. The mRNA was isolated as described in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into E. coli were randomly picked and placed into microtiter plates.

Probe Hybridization

Plasmid DNA was isolated from the E. coli colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred via LIMS to a computer. Absolute identity was maintained by barcoding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

Gene Isolation

The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequence of the *Physcomitrella patens* PK-3 (SEQ ID NO:8) or PK-10 (SEQ ID NO:11) was blasted against proprietary contig databases of canola, rice, and soybean at E value of E-10. (Altschul, Stephen et al. Gapped BLAST and PSI_BLAST: a new generation of protein database search program. Nucleic Acids Res. 25: 3389–3402). All the contig hits were analyzed for the putative full length sequences, and the longest clones representing the putative full length contigs were fully sequenced. Nine such contigs isolated from the proprietary contig databases are BnPK-1, BnPK-2, BnPK-3, BnPK-4, GmPK-1, GmPK-2, GmPK-3, GmPK-4, and OsPK-1. The homology of the BnPK-1, BnPK-2, BnPK-3, BnPK-4, GmPK-1, GmPK-2, GmPK-3, GmPK-4, and OsPK-1 amino acid sequences to the closest prior art is indicated in Tables 6–14.

TABLE 6

Degree of Amino Acid Identity and Similarity of BnPK-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnPK-1 | CAA55866 | Shaggy/ Glycogen Synthase Kinase-3 Homologue | Arabidopsis thaliana | 93% | 95% |

TABLE 7

Degree of Amino Acid Identity and Similarity of BnPK-2 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnPK-2 | CAB78873 | Shaggy-Like Protein Kinase Etha | Arabidopsis thaliana | 98% | 99% |

TABLE 8

Degree of Amino Acid Identity and Similarity of BnPK-3 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnPK-3 | CAA11903 | Shaggy-Like Kinase Beta | Arabidopsis thaliana | 92% | 94% |

TABLE 9

Degree of Amino Acid Identity and Similarity of BnPK-4 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| BnPK-4 | AAG51974 | Putative Leucine-Rich Repeat Transmembrane Protein Kinase 1 | Arabidopsis thaliana | 87% | 92% |

TABLE 10

Degree of Amino Acid Identity and Similarity of GmPK-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| GmPK-1 | AAL36376 | Putative Shaggy Protein Kinase dzeta | Arabidopsis thaliana | 80% | 87% |

TABLE 11

Degree of Amino Acid Identity and Similarity of GmPK-2 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| GmPK-2 | AAG50665 | Putative Glycogen Synthase Kinase | Arabidopsis thaliana | 85% | 92% |

TABLE 12

Degree of Amino Acid Identity and Similarity of GmPK-3 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| GmPK-3 | AAK93730 | Putative Shaggy Kinase | Arabidopsis thaliana | 85% | 89% |

TABLE 13

Degree of Amino Acid Identity and Similarity of GmPK-4 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| GmPK-4 | AAL59961 | Putative Leucine-Rich Repeat Transmembrane Protein Kinase | Arabidopsis thaliana | 58% | 68% |

TABLE 14

Degree of Amino Acid Identity and Similarity of OsPK-1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
|---|---|---|---|---|---|
| OsPK-1 | CAA48474 | Protein Kinase | Medicago sativa | 89% | 90% |

Example 7

Engineering Stress-tolerant Arabidopsis Plants by Over-Expressing the Genes PK-3 and PK-4

Binary Vector Construction: pBPS-JH001

The plasmid construct pLMNC53 (Mankin, 2000, Ph.D. thesis, University of North Carolina) was digested with HindIII (Roche) and blunt-end filled with Klenow enzyme and 0.1 mM dNTPs according to manufacturer's instructions. This fragment was purified by agarose gel and extracted via the QIAquick Gel Extraction kit (Qiagen) according to manufacturer's instructions. The purified fragment was then digested with EcoRI (Roche), purified by agarose gel, and extracted via the QIAquick Gel Extraction kit (Qiagen) according to manufacturer's instructions. The resulting 1.4 kilobase fragment, the gentamycin cassette, included the nos promoter, aacCI gene, and the g7 terminator.

The vector pBlueScript was digested with EcoRI and SmaI (Roche) according to manufacturer's instructions, and the resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 μg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al., 1989, Molecular Cloning, A Laboratory Manual. 2nd Edition, Cold Spring Harbor Laboratory Press, Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pBPS-JH001) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping were performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

Binary Vector Construction: pBPS-SC022

The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator.

Primers for PCR amplification of the NPTII gene were designed [5'NPT-Pst: GCG-CTG-CAG-ATT-TCA-TTT-GGA-GAG-GAC-ACG (SEQ ID NO:39); 3'NPT-Fse: CGC-GGC-CGG-CCT-CAG-AAG-AAC-TCG-TCA-AGA-AGG-CG (SEQ ID NO:40)]. The 0.9 kilobase NPTII gene was amplified via PCR from pCambia 2301 plasmid DNA using the following parameters: 94° C. 60 sec, {94° C. 60 sec, 61° C. (−0.1° C. per cycle) 60 sec, 72° C. 2 min}×25 cycles, 72° C. 10 min on Biometra T-Gradient machine. The amplified product was purified via the Qiaquick PCR Extraction kit (Qiagen) following manufacturer's instructions. The PCR DNA was then subcloned into the pCR-BluntII TOPO vector (Invitrogen) following manufacturer's instructions (NPT-Topo construct). These ligations were transformed into Top10 cells (Invitrogen) and grown on LB plates with 50 µg/ml kanamycin sulfate overnight at 37° C. Colonies were then used to inoculate 2 ml LB media with 50 µg/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using VectorNTI software revealed that there were not any PCR errors introduced in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation reaction was then transformed into Top10 cells (Invitrogen) under standard conditions, creating pBPS-sc019 construct. Colonies were selected on LB plates with 50 µg/ml kanamycin sulfate and grown overnight at 37° C. These colonies were then used to inoculate 2 ml LB media with 50 µg/ml kanamycin sulfate and grown overnight at 37° C. Plasmid DNA was recovered using the Qiaprep Spin Miniprep kit (Qiagen) following the manufacturer's instructions.

The pBPS-SC019 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the *Arabidopsis* Actin2 promoter with internal intron, the NPTII gene, and the OCS3 terminator.

The pBPS-JH001 vector was digested with SpeI and ApaI (Roche) and blunt-end filled with Klenow enzyme and 0.1 mM dNTPs (Roche) according to manufacturer's instructions. This produced a 10.1 kilobase vector fragment minus the Gentamycin cassette, which was recircularized by self-ligating with T4 DNA Ligase (Roche), and transformed into Top10 cells (Invitrogen) via standard conditions. Transformed cells were selected for on LB agar containing 50 µg/ml kanmycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. The recircularized plasmid was then digested with KpnI (Roche) and extracted from agarose gel via the Qiaex II DNA Extraction kit (Qiagen) according to manufacturers' instructions.

The Act-NPT Kpn-cut insert and the Kpn-cut pBPS-JH001 recircularized vector were then ligated together using T4 DNA Ligase (Roche) and transformed into Top10 cells (Invitrogen) according to manufacturers' instructions. The resulting construct, pBPS-SC022, now contained the Super Promoter, the GUS gene, the NOS terminator, and the Act-NPT cassette. Transformed cells were selected for on LB agar containing 50 µg/ml kanmycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPS-sc022 plasmid DNA was further propagated and recovered using the Plasmid Midiprep Kit (Qiagen) following the manufacturer's instructions.

Analyses of clones by restriction mapping was performed according to standard molecular biology techniques (Sambrook et al., 1989, Molecular Cloning, A Laboratory Manual, 2nd Edition, Cold Spring Harbor Laboratory).

Subcloning of PK-3, PK-4, PK-10, and PK-11 into the Binary Vectors

The fragments containing the different *Physcomitrella patens* polypeptide kinases were subcloned from the recombinant PCR2.1 TOPO vectors by double digestion with restriction enzymes (See Table 15) according to manufacturer's instructions. The subsequent fragment was excised from agarose gel with a QIAquick Gel Extraction Kit (Qiagen) according to manufacturer's instructions and ligated into the binary vector pBPS-JH001 or pBPS-SC022 which was cleaved with appropriate enzymes (See Table 15) and dephosphorylated prior to ligation. The resulting recombinant vectors (See Table 15) contained the corresponding Polypeptide Kinase in the sense orientation under the constitutive super promoter.

TABLE 15

Listed are the names of the various constructs of the Physcomitrella patens Polypeptide Kinases used for plant transformation

| Gene | Binary Vector | Enzymes Used to Generate Gene Fragment | Enzymes Used to Restrict the Binary Vector | Binary Vector Construct |
| --- | --- | --- | --- | --- |
| PK-3 | pBPS-JH001 | XmaI/SacI | XmaI/SacI | pBPS-LVM071 |
| PK-4 | pBPS-JH001 | XmaI/EcoRV | XmaI/Ecl136 | pBPS-LVM015 |
| PK-10 | pBPS-SC022 | XmaI/SacI | XmaI/SacI | pBPS-ERG015 |
| PK-11 | pBPS-SC022 | XmaI/SacI | XmaI/SacI | pBPS-LVM230 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold, 1993, Acad. Sci. Paris. 316:1194–1199; Bent et al., 1994, Science 265:1856–1860).

Screening of Transformed Plants

T1 seeds were sterilized according to standard protocols (Xiong et al., 1999, Plant Molecular Biology Reporter 17: 159–170). Seeds were plated on ½ Murashige and Skoog media (MS) pH 5.7 with KOH (Sigma-Aldrich), 0.6% agar and supplemented with 1% sucrose, 2 µg/ml benomyl (Sigma-Aldrich), and 150 µg/ml gentamycin (Sigma-Aldrich)(pBPS-JH001 transformants) or 50 µg/ml kanamycin (pBPS-SC022 transformants). Seeds on plates were vernalized for four days at 4° C. The seeds were germinated in a climatic chamber at an air temperature of 22° C. and light intensity of 40 micromol $s^-m^{-2}$ (white light; Philips TL 65W/25 fluorescent tube) and 16 hours light and 8 hours dark day length cycle. Transformed seedlings were selected after 14 days and transferred to ½ MS media pH 5.7 with KOH 0.6% agar plates supplemented with 1% sucrose, 0.5 g/L MES (Sigma-Aldrich), and 2 µg/ml benomyl (Sigma-Aldrich) and allowed to recover for five to seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromol $s^-m^{-2}$ (white light; Philips TL 65W/25 fluorescent tube). The RH was then decreased to 60%, and the seedlings were desiccated further for eight hours. Seedlings were then removed and placed on ½ MS 0.6% agar plates supplemented with 2 µg/ml benomyl (Sigma-Aldrich) and 0.5 g/L MES (Sigma-Aldrich) and scored after five days.

Under drought stress conditions, PK-3 over-expressing *Arabidopsis thaliana* plants showed a 54% survival rate (7 survivors from 13 stressed plants) to the stress screening, whereas the untransformed control only showed a 6% survival rate (1 survivor from 18 stressed plants). It is noteworthy that the analyses of these transgenic lines were performed with T1 plants, and therefore, the results will be better when a homozygous, strong expresser is found.

Transgenic plants overexpressing the PKSRP are screened for their improved drought tolerance, demonstrating that transgene expression confers drought tolerance.

TABLE 16

Summary of the drought stress tests

Drought Stress Test

| Gene Name | Number of survivors | Total number of plants | Percentage of survivors |
| --- | --- | --- | --- |
| PK-3 | 7 | 13 | 54% |
| Control | 1 | 18 | 6% |

"In-Soil" Drought Tolerance Screening

T1 seeds were sterilized in 100% bleach, 0.01% TritonX for five minutes two times and rinsed five times with sterile ddH2O. The sterile seeds were plated onto selection plates (½ MS, 0.6% phytagar, 0.5 g/L MES, 1% sucrose, 2 µg/ml benamyl, 50 µg/ml kanamycin, 0.6% agar). Plates were incubated at 4° C. for 4 days in the dark.

Plates were then moved for to 22° C. under continuous light for 10 days for germination and concomitant selection for transgenic plants. Seedlings were transplanted at the 4–5-leaf stage into 5.5 cm diameter pots filled with loosely packed soil (Metromix 360, Scotts) wetted with 1 g/L 20-20-20 fertilizer (Peters Professional, Scotts). Pots were placed randomly on trays with 5 control plants (transformed lines with empty vector) in each tray. Trays were placed randomly in the growth chamber.

Plants were grown (22° C., continuous light) for approximately seven days, watering as needed. Watering was stopped at the time when the majority of the plants was about to bolt, and this point was denoted day "0" of the assay. After this day, trays were turned 1800 every other day to minimize local drying patterns. The assay was stopped approximately at day 12–19, depending on the speed of drying of the pots containing the controls. Pots were then watered and survival rates were determined after 5 days.

PK-10 overexpressing *Arabidopsis thaliana* plants showed a 60% survival rate (6 survivors from 10 stressed plants) to the stress screening. PK-11 over-expressing *Arabidopsis thaliana* plants showed a 65% survival rate (11 survivors from 17 stressed plants) to the stress screening. This survival rate is significantly higher, 99% confidence interval, than that of the control. It is noteworthy that these analyses were performed with T1 plants. The results should be better when a homozygous, strong expresser is found.

TABLE 17

Summary of the drought stress tests

Drought Test Summary

| Gene Name | Number of survivors | Total number of plants | Percentage of survivors |
| --- | --- | --- | --- |
| PpPK-10 | 6 | 10 | 60% |
| PpPK-11 | 11 | 17 | 65% |

HS = significant difference with 99% confidence interval on a z-test

Freezing Tolerance Screening

Seedlings are moved to petri dishes containing ½ MS 0.6% agar supplemented with 2% sucrose and 2 µg/ml benomyl. After four days, the seedlings are incubated at 4° C. for 1 hour and then covered with shaved ice. The seedlings are then placed in an Environmental Specialist ES2000 Environmental Chamber and incubated for 3.5 hours beginning at −1.0° C., decreasing 1° C. each hour. The seedlings are then incubated at −5.0° C. for 24 hours and then allowed to thaw at 5° C. for 12 hours. The water is poured off and the seedlings are scored after 5 days. Transgenic plants over-expressing PK-3 and PK-4 are screened for their improved freezing tolerance demonstrating that transgene expression confers freezing tolerance.

Salt Tolerance Screening

Seedlings are transferred to filter paper soaked in ½ MS and placed on ½ MS 0.6% agar supplemented with 2 µg/ml benomyl the night before the salt tolerance screening. For the salt tolerance screening, the filter paper with the seedlings is moved to stacks of sterile filter paper, soaked in 50 mM NaCl, in a petri dish. After two hours, the filter paper with the seedlings is moved to stacks of sterile filter paper, soaked with 200 mM NaCl, in a petri dish. After two hours, the filter paper with the seedlings is moved to stacks of sterile filter paper, soaked in 600 mM NaCl, in a petri dish. After 10 hours, the seedlings are moved to petri dishes containing ½ MS 0.6% agar supplemented with 2 µg/ml benomyl. The seedlings are scored after 5 days. The transgenic plants are screened for their improved salt tolerance demonstrating that transgene expression confers salt tolerance.

Example 8

Detection of the PK-3 and PK-4 Transgenes in the Transgenic *Arabidopsis* Lines

To check for the presence of the PK-3 and PK-4 transgenes in transgenic *Arabidopsis* lines, PCR was performed on genomic DNA which contaminates the RNA samples taken as described in Example 9 below. Two and one half microliters of the RNA sample was used in a 50 µl PCR reaction using Taq DNA polymerase (Roche Molecular Biochemicals) according to the manufacturer's instructions.

Binary vector plasmid with each gene cloned in was used as positive control, and the wild-type C24 genomic DNA was used as negative control in the PCR reactions. Ten µl of the PCR reaction was analyzed on 0.8% agarose-ethidium bromide gel.

PK-3: The primers used in the reactions were:

5'CGAGAGCTGCAGATCATGCGACTGTTG3'  (SEQ ID NO:50)

5'GCTCTGCCATCACGCAACCCATCGAC 3'  (SEQ ID NO:51)

The PCR program was as following: 35 cycles of 1 minute at 94° C., 30 seconds at 62° C., and 1 minute at 72° C., followed by 5 minutes at 72° C. A 0.45 kilobase fragment was produced from the positive control and the transgenic plants.

PK-4: The primers used in the reactions were:

(SEQ ID NO:37)
5'ATCCCGGGAGGCATTGAACTACCTGGAGTGAG3'

(SEQ ID NO:43)
5'GCGATATCGTTGAACTAGTAATCTGTGTTAACTTTATC3'

The PCR program was as following: 30 cycles of 1 minute at 94° C., 1 minute at 62° C., and 4 minutes at 72° C., followed by 10 minutes at 72° C. A 1.7 kilobase fragment was produced from the positive control and the transgenic plants.

The transgenes were successfully amplified from the T1 transgenic lines, but not from the wild type C24. This result indicates that the T 1 transgenic plants contain at least one copy of the transgenes. There was no indication of existence of either identical or very similar genes in the untransformed *Arabidopsis thaliana* control which could be amplified by this method from the wild-type plants.

Example 9

Detection of the PK-3 and PK-4 Transgene mRNA in Transgenic *Arabidopsis* Lines

Transgene expression was detected using RT-PCR. Total RNA was isolated from stress-treated plants using a procedure adapted from Verwoerd et al., 1989, NAR 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH 8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3 M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the Superscript First-Strand Synthesis System for RT-PCR (Gibco-BRL) following manufacturer's recommendations.

PCR amplification of a gene-specific fragment from the synthesized cDNA was performed using Taq DNA polymerase (Roche) and gene-specific primers described in Example 8 in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. This result indicated that the transgenes are expressed in the transgenic lines and suggested that their gene product improved plant stress tolerance in the transgenic line. In agreement with the previous statement, no expression of identical or very similar endogenous genes could be detected by this method. These results are in agreement with the data from Example 8.

Example 10

Engineering Stress-tolerant Soybean Plants by Over-Expressing the PK-3, PK-4, PK-10, and PK-11 Genes The constructs pBPS-LVM071, pBPS-LVM015, pBPS-ERG015, and pBPS-LVM230 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 μM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and transferred to Petri dishes containing solid MS medium supplemented with 2% sucrose and incubated for 2 days, in the dark at room temperature.

Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 μmol m$^{-2}$sec$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 μmol m$^{-2}$ sec$^{-1}$ light intensity and 12 hours photoperiod for about 80 days.

The transgenic plants are then screened for their improved drought, salt, and/or cold tolerance according to the screening method described in Example 7, demonstrating that transgene expression confers stress tolerance.

Example 11

Engineering Stress-tolerant Rapeseed/Canola Plants by Over-Expressing the PK-3, PK-4, PK-10 and PK-11 Genes The constructs pBPS-LVM071, pBPS-LVM015, pBPS-ERG015, and pBPS-LVM230 are used to transform rapeseed/canola as described below.

The method of plant transformation described herein is applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed, and the seeds are air dried overnight in a half-open sterile Petri dish. During this period, the seeds lose approximately 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7, demonstrating that transgene expression confers stress tolerance.

Example 12

Engineering Stress-tolerant Corn Plants by Over-Expressing the PK-3, PK-4, PK-10, and PK-11 Genes The constructs pBPS-LVM071, pBPS-LVM015, pBPS-ERG015, and pBPS-LVM230 are used to transform corn as described below.

Transformation of maize (*Zea Mays* L.) is performed with the method described by Ishida et al., 1996, Nature Biotech. 14745–50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt, and/or cold tolerance according to the screening method described in Example 7, demonstrating that transgene expression confers stress tolerance.

Example 13

Engineering Stress-tolerant Wheat Plants by Over-Expressing the PK-3, PK-4, PK-10, and PK-11 Genes The constructs pBPS-LVM071, pBPS-LVM015, pBPS-ERG015, and pBPS-LVM230 are used to transform wheat as described below.

Transformation of wheat is performed with the method described by Ishida et al., 1996, Nature Biotech. 14745–50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7, demonstrating that transgene expression confers stress tolerance.

Example 14

Identification of Identical and Heterologous Genes

Gene sequences can be used to identify identical or heterologous genes from cDNA or genomic libraries. Identical genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution, hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially identical or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only in a distinct domain of (for example 10–20 amino acids) can be carried out by using synthetic radio labeled oligonucleotide probes. Radiolabeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:

6×SSC 0.01 M sodium phosphate 1 mM EDTA (pH 8)

0.5% SDS

100 µg/ml denatured salmon sperm DNA 0.1% nonfat dried milk

During hybridization, temperature is lowered stepwise to 5–10° C. below the estimated oligonucleotide $T_m$ or down to room temperature followed by washing steps and autoradiography. Washing is performed with low stringency such as 3 washing steps using 4×SSC. Further details are described by Sambrook, J. et al., 1989, "Molecular Cloning: A Laboratory Manual," Cold Spring Harbor Laboratory Press or Ausubel, F. M. et al., 1994, "Current Protocols in Molecular Biology," John Wiley & Sons.

Example 15

Identification of Identical Genes by Screening Expression Libraries with Antibodies c-DNA clones can be used to produce recombinant polypeptide for example in *E. coli* (e.g. Qiagen QIAexpress pQE system). Recombinant polypeptides are then normally affinity purified via Ni-NTA affinity chromatography (Qiagen). Recombinant polypeptides are then used to produce specific antibodies for example by using standard techniques for rabbit immunization. Antibodies are affinity purified using a Ni-NTA column saturated with the recombinant antigen as described by Gu et al., 1994, BioTechniques 17:257–262. The antibody can than be used to screen expression cDNA libraries to identify identical or heterologous genes via an immunological screening (Sambrook, J. et al., 1989, "Molecular Cloning: A Laboratory Manual," Cold Spring Harbor Laboratory Press or Ausubel, F. M. et al., 1994, "Current Protocols in Molecular Biology", John Wiley & Sons).

Example 16

In vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D., 1996, DNA repair mechanisms, in: *Escherichia coli* and *Salmonella*, p. 2277–2294, ASM: Washington.) Such strains are well known to those skilled in the art. The use of such strains is illustrated, for example, in Greener, A. and Callahan, M., 1994, Strategies 7: 32–34. Transfer of mutated DNA molecules into plants is preferably done after selection and testing in microorganisms. Transgenic plants are generated according to various examples within the exemplification of this document.

Example 17

In vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., 1979, Enzymes. Longmans: London; Fersht, 1985, Enzyme Structure and Mechanism. Freeman: New York; Walsh, 1979, Enzymatic Reaction Mechanisms. Freeman: San Francisco; Price, N. C., Stevens, L., 1982, Fundamentals of Enzymology. Oxford Univ. Press: Oxford; Boyer, P. D., ed., 1983, The Enzymes, $3^{rd}$ ed. Academic Press: New York; Bisswanger, H., 1994, Enzymkinetik, $2^{nd}$ ed. VCH: Weinheim (ISBN 3527300325); Bergmeyer, H. U., Bergmeyer, J., Graβl, M., eds., 1983–1986, Methods of Enzymatic Analysis, $3^{rd}$ ed., vol. I-XII, Verlag Chemie: Weinheim; and Ullmann's Encyclopedia of Industrial Chemistry, 1987, vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al., 1995, EMBO J. 14: 3895–3904 and references cited therein). Reporter gene test systems are well known and established for applications in both prokaryotic and eukaryotic cells, using enzymes such as β-galactosidase, green fluorescent protein, and several others.

The determination of activity of membrane-transport proteins can be performed according to techniques such as those described in Gennis, R. B., 1989, Pores, Channels and Transporters, in Biomembranes, Molecular Structure and Function, pp. 85–137, 199–234 and 270–322, Springer: Heidelberg.

Example 18

Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, the cells can be harvested from the culture by low-speed centrifugation, and the cells can be lysed by standard techniques, such as mechanical force or sonification. Organs of plants can be separated mechanically from other tissue or organs. Following homogenization, cellular debris is removed by centrifugation, and the supernatant fraction containing the soluble proteins is retained for further purification of the desired compound. If the product is secreted from desired cells, then the cells are removed from the culture by low-speed centrifugation, and the supernatant fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F., 1986, Biochemical Engineering Fundamentals, McGraw-Hill: New York. Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994, Appl. Environ. Microbiol. 60:133–140; Malakhova et al., 1996, Biotekhnologiya 11:27–32; Schmidt et al., 1998, Bioprocess Engineer 19:67–70; Ulmann's Encyclopedia of Industrial Chemistry, 1996, vol. A27, VCH: Weinheim, p. 89–90, p. 521–540, p. 540–547, p. 559–566, 575–581, and p. 581–587; Michal, G., 1999, Biochemical Pathways: An Atlas of Biochemistry and Molecular Biology, John Wiley and Sons; Fallon, A. et al., 1987, Applications of HPLC in Biochemistry in: Laboratory Techniques in Biochemistry and Molecular Biology, vol. 17.

We claim:

1. An isolated nucleic acid, wherein the nucleic acid comprises a polynucleotide selected from the group consisting of:
   a) a polynucleotide as defined in SEQ ID NO:5; and
   b) a polynucleotide encoding a polypeptide as defined in SEQ ID NO:6.

2. The isolated nucleic acid of claim 1, wherein the nucleic acid comprises the polynucleotide as defined in of SEQ ID NO:5.

3. The isolated nucleic acid of claim 1, wherein the nucleic acid comprises the polynucleotide encoding the polypeptide of SEQ ID NO:6.

4. A vector comprising a polynucleotide selected from the group consisting of:
   a) a polynucleotide as defined in SEQ ID NO:5; and
   b) a polynucleotide encoding a polypeptide as defined in SEQ ID NO:6.

5. A transgenic plant cell transformed with a nucleic acid comprising a polynucleotide selected from the group consisting of:
   a) a polynucleotide as defined in SEQ ID NO:5; and
   b) a polynucleotide encoding a polypeptide as defined in SEQ ID NO:6.

6. The transgenic plant cell of claim 5, wherein the nucleic acid comprises the polynucleotide as defined in SEQ ID NO:5.

7. The transgenic plant cell of claim 5, wherein the nucleic acid comprises the polynucleotide encoding the polypeptide as defined in SEQ ID NO:6.

8. A transgenic plant transformed with a nucleic acid comprising a polynucleotide selected from the group consisting of:
   a) a polynucleotide as defined in SEQ ID NO:5; and
   a polynucleotide encoding a polypeptide as defined in SEQ ID NO:6.

9. The plant of claim 8, wherein the plant is a monocot.

10. The plant of claim 8, wherein the plant is a dicot.

11. The plant of claim 8, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

12. A plant seed comprising a transgene, wherein the transgene is selected from the group consisting of:
   a) a polynucleotide as defined in SEQ ID NO:5; and
   b) a polynucleotide encoding a polypeptide as defined in SEQ ID NO:6; wherein the seed is true breeding for an increased tolerance to an environmental stress as compared to a wild type variety of the seed, and wherein the environmental stress is selected from the group consisting of drought, high salinity and low temperature.

13. A method of producing a transgenic plant containing a nucleic acid, wherein the plant has an increased tolerance to an environmental stress as compared to a wild type variety of the plant, the method comprising the steps of:
   a) transforming a plant cell with an expression vector comprising the nucleic acid; and
   b) generating from the plant cell the transgenic plant, wherein the environmental stress is selected from the group consisting of drought, high salinity and low temperature, and the nucleic acid is selected from the group consisting of:
      i) a polynucleotide as defined in SEQ ID NO:5; and
      ii) a polynucleotide encoding a polypeptide as defined in SEQ ID NO:6.

14. The method of claim 13, wherein the plant is a monocot.

15. The method of claim 13, wherein the plant is a dicot.

16. The method of claim 13, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and a forage crop plant.

17. The method of claim 13, wherein the nucleic acid comprises the polynucleotide encoding the polypeptide of SEQ ID NO:6.

18. The method of claim 13, wherein the plant's stress tolerance is increased by increasing expression of the nucleic acid in the plant.

19. The method of claim 13, wherein the nucleic acid is operably associated with a promoter.

20. The method of claim 19, wherein the promoter is tissue specific.

21. The method of claim 19, wherein the promoter is developmentally regulated.

22. The method of claim 19, wherein the promoter is stress-inducible.

23. The plant of claim 11, wherein the plant is corn.

24. The plant of claim 11, wherein the plant is soybean.

25. The plant of claim 11, wherein the plant is rapeseed or canola.

26. The plant of claim 11, wherein the plant is cotton.

* * * * *